US009867795B2

(12) United States Patent
Freeman et al.

(10) Patent No.: US 9,867,795 B2
(45) Date of Patent: *Jan. 16, 2018

(54) NITRATED LIPIDS AND METHODS OF MAKING AND USING THEREOF

(71) Applicants: The UAB Research Foundation, Birmingham, AL (US); State of Oregon Acting By and Through the Board of Education on Behalf of the University of Oregon, Eugene, OR (US); University College Cardiff Consultants Limited, Cardiff (GB); Morehouse School of Medicine, Inc., Atlanta, GA (US)

(72) Inventors: Bruce A. Freeman, Pittsburgh, PA (US); Francisco Schopfer, Pittsburgh, PA (US); Valerie O'Donnell, Penarth (GB); Paul Baker, Pittsburgh, PA (US); Yuqing E. Chen, Ann Arbor, MI (US); Bruce Branchaud, Eugene, OR (US)

(73) Assignees: The UAB Research Foundation, Birmingham, AL (US); The State of Oregon Acting by and through the State Board of Higher Education on Behalf of the University of Oregon, Eugene, OR (US); University College Cardiff Consultants Limited, Cardiff (GB); Morehouse School of Medicine, Inc., Atlanta, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/357,731

(22) Filed: Nov. 21, 2016

(65) Prior Publication Data
US 2017/0119717 A1   May 4, 2017

Related U.S. Application Data

(60) Continuation of application No. 15/040,376, filed on Feb. 10, 2016, now Pat. No. 9,522,156, which is a
(Continued)

(51) Int. Cl.
  *A61K 31/70*   (2006.01)
  *A61K 31/201*  (2006.01)
  *A61K 45/06*   (2006.01)

(52) U.S. Cl.
  CPC ............ *A61K 31/201* (2013.01); *A61K 45/06* (2013.01)

(58) Field of Classification Search
  CPC .............................. A61K 31/201; A61K 45/06
  (Continued)

(56) References Cited

U.S. PATENT DOCUMENTS

| 3,578,687 A | 5/1971 | Larkin et al. |
| 3,819,561 A | 6/1974 | Bruenner |

(Continued)

FOREIGN PATENT DOCUMENTS

| GB | 587992 A | 5/1947 |
| GB | 1407932 A | 10/1975 |

(Continued)

OTHER PUBLICATIONS

Lundberg, et. al., "Nitrate and Nitrite in Biology, Nutrition and Therapeutics," Nat. Chem. Bio. 2009, 5, pp. 865-869.
(Continued)

*Primary Examiner* — Deborah D Carr
(74) *Attorney, Agent, or Firm* — Kilpatrick Townsend & Stockton LLP

(57) ABSTRACT

Described herein are nitrated lipids and methods of making and using the nitrated lipids.

18 Claims, 34 Drawing Sheets

Related U.S. Application Data continuation of application No. 14/638,370, filed on Mar. 4, 2015, now Pat. No. 9,295,678, which is a continuation of application No. 13/646,985, filed on Oct. 8, 2012, now Pat. No. 9,006,473, which is a continuation of application No. 12/797,460, filed on Jun. 9, 2010, now Pat. No. 8,309,526, which is a division of application No. 11/568,377, filed as application No. PCT/US2005/014305 on Apr. 26, 2005, now Pat. No. 7,776,916.

(60) Provisional application No. 60/566,005, filed on Apr. 28, 2004.

(58) Field of Classification Search
USPC .......................................................... 514/25
See application file for complete search history.

(56) References Cited

U.S. PATENT DOCUMENTS

| | | | |
|---|---|---|---|
| 3,917,660 A | 11/1975 | Sasaki et al. | |
| 6,924,309 B2 | 8/2005 | Ferrante et al. | |
| 7,312,191 B2 | 12/2007 | Rose et al. | |
| 7,776,916 B2 * | 8/2010 | Freeman | A61K 31/21 514/178 |
| 7,977,315 B2 | 7/2011 | Rose et al. | |
| 9,006,473 B2 | 4/2015 | Freeman et al. | |
| 9,295,678 B2 * | 3/2016 | Freeman | A61K 31/21 |
| 9,522,156 B2 * | 12/2016 | Freeman | A61K 31/21 |
| 2001/0037598 A1 | 11/2001 | Suppes et al. | |
| 2004/0006248 A1 | 1/2004 | Paiocchi et al. | |
| 2004/0254240 A1 | 12/2004 | Ferrante et al. | |
| 2006/0063953 A1 | 3/2006 | Paiocchi et al. | |
| 2007/0232579 A1 | 10/2007 | Freeman et al. | |
| 2010/0286257 A1 | 11/2010 | Perricone | |
| 2010/0286271 A1 | 11/2010 | Perricone | |
| 2010/0286272 A1 | 11/2010 | Perricone | |
| 2013/0210917 A1 | 8/2013 | Freeman et al. | |
| 2015/0246059 A1 | 9/2015 | Freeman et al. | |

FOREIGN PATENT DOCUMENTS

| | | | | |
|---|---|---|---|---|
| WO | 2001021575 A1 | 3/2001 | | |
| WO | WO 0121757 A1 * | 3/2001 | | C11D 1/37 |
| WO | 2001078654 A2 | 10/2001 | | |
| WO | 2001078719 A1 | 10/2001 | | |
| WO | 2001079156 A1 | 10/2001 | | |
| WO | 2002022559 A2 | 3/2002 | | |
| WO | 2005110396 A2 | 11/2005 | | |
| WO | 2009017802 A1 | 2/2009 | | |

OTHER PUBLICATIONS

Ma, et al., "Hydrohalogenation Reaction of Substituted 1, 2-Allenic Carboxylic Acids, Esters, Amides, Nitriles and Diphenyl Phosphine Oxides", Synthesis, 2001, 5, pp. 713-730.

Marnett, et al., "Regulation of Prostaglandin Biosynthesis by Nitric Oxide is Revealed by Targeted Deletion of Inducible Nitric-Oxide Synthese," J. Biol. Chem. 2000, vol. 275(18), pp. 13427-13430.

Marshall, et al., "Nitrosation and Oxidation in the Regulation of Gene Expression" FASEB 2000, vol. 14. pp. 1889-1900.

Marx, et al., "Peroxisome Proliferator-Activated Receptors and Atherogenesis, Regulators of Gene Expression in Vascular Cells," Circ. Res. 2004, vol. 94, pp. 1168-1178.

McIntyre, et al., "Identification of an Intracellular Receptor for Lysophosphatidic Acid (LPA): LPA is a Transcellular PPARgamma Agonist" Proc. Natl. Acad. Sci. 2003, vol. 100(1), pp. 131-136.

Miranda, et al., "The Chemical Biology of Nitric Oxide" Nitric Oxide: Biology and Pathobiology, Academic Press, San Diego 2000, pp. 41-55.

Montuschi, et al., "Isoprostanes: Markers and Mediators of Oxidative Stress" FASEB 2004, vol. 18, pp. 1791-1800.

Mukherjee, et al., "A Selective Peroxisome Proliferator-Activated Receptor-gamma(PPARgamma) Modulatory Blocks Adipocyte Differentiation but Stimulates Glucose Uptake in 3T3-L1 Adipocytes", Mol. Endocrinol. 2000, vol. 14, pp. 1425-1433.

Nadtochiy, et al., "Mitochondrial Nitroalkene Formation and Mild Uncoupling in Ischaemic Preconditioning: Implications for Cardioprotection", Cardiovasc Res. May 1, 2009;82(2):333-40.

Nadtochiy, et al., "Nitroalkenes Confer Acute Cardioprotection Via Adenine Nucleotide Translocase 1" J. Biol. Chem. 2012, 287, pp. 3573-3580.

Nagy, et al., "Oxidized LDL Regulates Macrophage Gene Expression Through Ligand Activation of PPARgamma" Cell 1998, vol. 93, pp. 229-240.

Napolitano, et al., "Acid-Promoted Reactions of Ethyl Linoleate with Nitrite Ions: Formation and Structural Characterization of Isomeric Nitroalkene, Nitrohydroxy, and Novel 3-Nitro-1, 5-Hexadiene and 1,5-Dinitro-1, 3-Pentadiene Products" J. Org. Chem. 2000, vol. 65, pp. 4853-4860.

Napolitano, et al., "The Acid-Promoted Reaction of Ethyl Linoleate with Nitrite. New Insights from 15N-Labelling and Peculiar Reactivity of a Model Skipped Diene" Tetrahedron 2004, vol. 58, pp. 5061-5067.

Napolitano, et al., "Acid-Induced Structural Modifications of Unsaturated Fatty Acids and Phenolic Olive Oil Constituents by Nitrite-Ions: A Chemical Assessment," Chemical Research in Toxicology, 2004, 17, pp. 1329-1337.

Nathan, "Nitric Oxide as a Secretory Product of Mammalian Cells" Federation of Amer. Soc. for Experimental Biol. J. 1992, vol. 6, pp. 3051-3064.

O'Donnell & Freeman, "Interactions Between Nitric Oxide and Lipid Oxidation Pathways, Implications for Vascular Disease", Circ. Res. 2001, vol. 88. pp. 12-21.

O'Donnell, et al., "15-Lipoxygenase Catalytically Consumes Nitric Oxide and Impairs Activation of Guanylate Cyclase" J. Biol. Chem. 1999, vol. 274, pp. 20083-20091.

O'Donnell, et al., "Catalytic Consumption of Nitric Oxide by Prostagladin H Synthase-1 Regulates Platelet Function" J. Biol. Chem. 2000, vol. 275(49), pp. 38239-38244.

O'Donnell, et al., "Nitration of Unsaturated Fatty Acids by Nitric Oxide-Derived Reactive Nitrogen Species Perosynitrite, Nitrous Acid, Nitrogen Dioxide, and Nitronium Ion" Chem. Res. Toxicol. 1999, vol. 12, pp. 83-92.

O'Donnell, et al., "Nitric Oxide Inhibition of Lipid Peroxidation: Kinetics of Reaction with Lipid Peroxyl Radicals and Comparison with Alpha-Tocopherol," Biochem. 1997, vol. 36, pp. 15216-15223.

Ono, et al., "A convenient procedure for the conversion of (E)-nitroalkenes to (Z)-nitroalkenes via erythro-β- nitroselenides," J. Chem. Soc. Chem. Commun. 1987, p. 1550-1551.

Padmaja and Huie, "The Reaction of Nitric Oxide with Organic Peroxyl Radicals" Biochem. Biophys. Res. Commun. 1993, vol. 195(2), pp. 539-544.

Pawliczak, et al., "85-kDa Cytosolic Phospholipase A2 Mediates Peroxisome Proliferator-Activated Receptor Gamma Activation in Human Lung Epithelial Cells," J. Biol. Chem. 2002, vol. 277, pp. 33153-33163.

Pryor, et al., "Reaction of Nitrogen Dixiode with Alkenes and Polyunsaturated Fatty Acids: Addition and Hydrogen Abstraction Mechanism," J. Amer. Chem. Soc. 2004, vol. 104, pp. 6685-6692.

Quijano, et al., "Reaction of Peroxynitrite with Mn-Superoxide Dismutase: Role of the Metal Center in Decomposition Kinetics and Nitration" J. Biol. Chem. 2001, vol. 276, n. 15, pp. 11631-11638.

Radi, et al., "Peroxynitrite Oxidation of Sulfhydryls: The Cytotoxic Potential of Superoxide and Nitric Oxide," J. Biol. 1991, vol. 266, No. 7, pp. 4244-4250.

Radi, et al., "Peroxynitrite Reactions with Carbon Dioxide-Bicarbonate," Methods Enzymol., 1991, vol. 301, pp. 353-367.

Ranu & Chakraborty, "Highly Selective Reduction of Conjugated Nitroalkenes with Zinc Borohydride in DME" Tetrahedron Letters 1991, vol. 32, pp. 3579-3582.

(56) References Cited

OTHER PUBLICATIONS

Rassaf, et al., "Concomitant Presence of N-Nitroso and S-Nitroso Proteins in Human Plasma", Free Radic. Biol. Med. 2002, vol. 33, Nat. Med. 2003, vol. 33(11), pp. 1590-1596.

Rassaf, et al., "NO Adducts in Mammalian Red Blood Cells: Too Much or Too Little?" Nat. Med. 2003, vol. 9(5), pp. 481-482.

Rosen & Spiegelman, "PPARgamma: A Nuclear Regulator of Metabolism, Differentiation, and Cell Growth" J. Bio. Chem. 2001, vol. 276, pp. 37731-37734.

Rubbo, et al., "Form on Nitric Oxide: Chemical Events in Toxicity, Nitric Oxide Regulation of Tissue Free Radical Injury," Chem. Res. Toxicol. 1996, vol. 9, pp. 809-820.

Rubbo, et al., "Nitric Oxide Inhibition of Lipoxygenase-Dependent Liposome and Low-Density Lipoprotein Oxidation: Termination of Radical Chain Propagation Reactions and Formation of Nitrogen-Containing Oxidized Lipid Derivatives" Arch. Biochem. Biophys. 1995, vol. 324(1), pp. 15-25.

Rubbo, et al., "Nitric Oxide Reaction with Lipid Peroxyl Radicals Spares Alpha-Tocopherol During Lipid Peroxidation" J. Biol. Chem. 2000, vol. 275(25), pp. 10812-10818.

Rudolph, et al., "Cardiovascular Consequences When Nitric Oxide and Lipid Signaling Converge," Cir. Res. 2009, vol. 105, pp. 511-522.

Rudolph, et al., "Endogenous Generation and Protective Effects of Nitro-Fatty Acids in Murine Model of Focal Cardiac Ischaemia and Reperfusion", Cardiov. Research Advance Access 2009, pp. 1-12.

Rudolph, et al., "Nitro-Fatty Acid Metabolism: Saturation, Desaturation, b-Oxidation and Protein Adduction" J. Biol. Chem. 2009, vol. 284, No. 3, pp. 1461-1473.

Rudolph, et al., "Nitro-Fatty Acids Reduce Atheroscelerosis in Apolipoprotein E-Deficient Mice", Ather. Thromb. Vasc. Bio. 2010, 30, pp. 938-945.

Rudolph, et al., "Transduction of Redox Signaling by Electrophile-Protein Reactions", Science Signaling 2009, vol. 2, Issue 90 re7, pp. 1-13.

Saulnier-Blache, et al., "A Simple and Highly Sensitive Radioenzymatic Assay for Lysophosphatidic Acid Quantification" J. Lipid Res. 2000, vol. 41, pp. 1947-1951.

Schopfer, et al., "Fatty Acid Transduction of Nitric Oxide Signaling, Nitrolinoleic Acid is a Hydrophobically Stabilized Nitric Oxide Donor" J. Bio.. Chem. 2005, vol. 19, pp. 19289-19297.

Schopfer, et al., "Nitrolinoleic Acid: An Endogenous Peroxisome Proliferators-Activated Receptor Gamma Ligand" Proc. Natl. Acad. Sci. 2005, vol. 102(7), pp. 2340-2345.

Schopfer, et al., "Covalent Peroxisome Proliferator-Activated Receptor γ adduction by Nitro-Fatty Acids: Selective Ligand Activity and Anti-Diabetic Signaling Actions," J. Biol. Chem. 2010, 285, pp. 12321-12333.

Schopfer, et al., "Detection and Quantification of Protein Adduction by Electrophilic Fatty Acids: Mitochondrial Generation of Fatty Acid Nitroalkene Derivatives" Free Radic. Biol. Med. 2009, vol. 46, pp. 1250-1259.

Sculptoreanu, et al., "Nitro-Oleic Acid Inhibits Firing and Activates TRPV-1, and TRPA-1 Mediated Inward Currents in Dorsal Root Ganglion Neurons from Adult Male Rats" J. Pharm. Expt. Therap. (2010), 333, pp. 883-895.

Sharpless, et al., "Mild Procedure for the Conversion of Epoxides to Allylic Alcohols. First Organoselenium Reagent", J. Am. Chem. Soc. 1973, 95, pp. 2697-2699.

Smith, "Prostanoid Biosynthesis and Mechanisms of Action" Am. J. Physiol. 1992, vol. 263, pp. F181-F191.

Snider, et al., "Oxidative and Dehydrative Cyclizations of Nitroacetate Esters with MN(OAc)3", Tetrahedon, Sep. 23, 2002, 58(39), pp. 7821-7827.

Subczynski, et al., "Permeability of Nitric Oxide Through Lipid Bilayer Membranes" Free Radic. Res. 1996, vol. 24, pp. 343-349.

Szoka & Paphadjopolous, "Comparative Properties and Methods of Preparation of Lipid Vesicles (Liposomes)" Annu. Reg. Biophys. Bioeng. 1990, vol. 9, pp. 467-508.

Tang, et al., "Nitroalkenes Induce Rat Aortic Smooth Muscle Cell Apoptosis Via Activation of Caspase-Dependent Pathways," Biochem. Biophys. Res. Commun. 2010, 397, pp. 239-244.

Thatcher, et al., "Nitrates and No Release: Contemporary Aspects in Biological and Medicinal Chemistry" Free Radic. Biol. Med. 2004, vol. 37(8), pp. 1122-1143.

Thomas, et al., "The Biological Lifetime of Nitric Oxide: Implications for the Perivascular Dynamics of NO and O2" Proc. Natl. Acad. Sci. 2001, vol. 98, pp. 355-360.

Tontonoz, et al., "mPPARgamma2: Tissue-Specific Regulator of an Adipocyte Enhancer" Genes Dev. 1994, vol. 8 (10), pp. 1224-1234.

Tontonoz, et al., "Stimulation of Adipogenesis in Fibroblasts by PPARgamma2, a Lipid-Activated Transcription Factor", Cell 1994, vol. 79, pp. 1147-1156.

Tzameli, et al., "Regulated Production of A Peroxisome Proliferatory-Activated Receptor-gamma Ligand During an Early Phase of Adipocyte Differentiation in 3T3-L1 Adipocytes", J. Biol. Chem. 2004, vol. 279(34), pp. 36093-36102.

Vasil'ev et al., "The Action of Nitrogen Dioxide Upon Eurcic Acid" Lomonosova 1995, vol. 5, pp. 50-58.

Vidwans, et al., "Differential Modulation of Prostaglandin H Synthase-2 by Nitric Oxide-Related Species in Intact Cells" Biochem. 2001, vol. 40, pp. 11533-11542.

Villacorta, et al., "Nitro-Linoleic Acid Inhibits Vascular Smooth Muscle Cell Proliferation Via the Keapl/Nrf2 Signaling Pathway" Am. J. Physiol. Heart Cir. Physiol. Apr. 27, 2007, 293:H770-H770-6.

Villacorta, et al., "PPARy and its Ligands: Therapeutic Implications in Cardiovascalur Disease" Clin. Sci. 2009, n. 116, pp. 205-218.

Von Knethen & Brune, "Activation of Peroxisome Proliferator-Activated Receptor Gamma by Nitric Oxide in Monocytes/Macrophages Down-Regulates p47phox and Attenuates the Respiratory Burst," J. Immunol. 2002, vol. 169, pp. 2619-2626.

Wang, et al., "Constitutive Activation of Peroxisome Proliferator-Activated Receptor-Gamma Suppresses Pro-Inflammatory Adhesion Molecules in Human Vascular Endothelial Cells" J. Biol. Chem. 2002, vol. 277(13), pp. 34176-34181.

Wang, et al., "Nitro-Oleic Acid Protects Against Endotoxin-Induced Endotoxemia and Multiorgan Injury in Mice," Am. J. Physiol. Renal Physiol., 2010, 298, pp. F754-762.

Wang, et al., "Effects of Endogenous PPAR Agonist Nitro-Oleic Acid on Metabolic Syndrome in Obese Zucker Rats." PPAR Res. 2010, 601562.

Wright, et al., "Fatty Acid Transduction of Nitric Oxide Signaling: Nitrolinoleic Acid Potently Activates Endothelial Heme Oxygenase 1 Expression," PNAS, vol. 103(11), pp. 4299-4304.

Wright, et al., "Human Heme Oxxygenase-1 Induction by Nitro-Linoleic Acid is Mediated by Cyclic AMP, AP-1, and E-Box Response Element Interactions" Biochem. J. 2009, m. BJ20090339, pp. 1-31.

Xu, et al., "Lysophosphatidic Acid as a Potential biomaker for Ovarian and Other Gynecologic Cancers" JAMA 1998, vol. 280, pp. 719-723.

Zhang, et al., "Lysophosphatidic Acid Induces Neointima Formation Through PPARgamma Activation" J. Exp. Med. 2004, vol. 199(6), pp. 763-774.

Zhang, et al., "Selective Disruption of PPARgamma2 Impairs the Development of Adipose Tissue and Insulin Sensitivity" Proc. Natl. Avad. Sci. 2004, vol. 101(29), pp. 10703-10708.

Zhang, et al., "Nitro-Oleic Acid Inhibits Angiotensin II-Induced Hypertension", Cir. Res. (2010), 107, pp. 540-548.

Rubbo, et al., "Nitric Oxide Regulation of Superoxide and Peroxynitrite-Dependent Lipid Peroxidation," J. Biol. Chem. 1994, vol. 269(42), pp. 26066-26075.

Schopfer, et al., "No-Dependent Protein Nitration: A Cell Signaling Event or an Oxidative Inflammatory Response," Trends Biochem. Sci. 2003, vol. 28, pp. 646-654.

U.S. Appl. No. 11/568,377, Non-Final Office Action dated Sep. 4, 2009, 5 pages.

U.S. Appl. No. 11/568,377, Notice of Allowance dated Jul. 8, 2010, 2 pages.

International Preliminary Report on Patentability in related PCT/US2005/014305 dated Nov. 14, 2006, 5 pages.

(56) References Cited

OTHER PUBLICATIONS

U.S. Appl. No. 12/797,460, Non-Final Office Action dated Dec. 22, 2011, 6 pages.
U.S. Appl. No. 12/797,460, Notice of Allowance dated Jul. 6, 2012, 21 pages.
U.S. Appl. No. 11/568,377, Notice of Allowance dated Jun. 9, 2010, 2 pages.
U.S. Appl. No. 11/568,377, Notice of Allowance dated Mar. 5, 2010, 4 pages.
U.S. Appl. No. 13/646,985, Non Final Office Action dated Jun. 12, 2014, 9 pages.
U.S. Appl. No. 13/646,985, Non-Final Office Action dated May 1, 2014, 9 pages.
U.S. Appl. No. 13/646,985, Notice of Allowance, dated Dec. 5, 2014, 5 pages.
International Search Report and Written Opinion in related PCT/US2005-014305, dated Oct. 12, 2006.
U.S. Appl. No. 14/638,370, Non-Final Office Action, dated Jul. 8, 2015, 6 pages.
U.S. Appl. No. 14/638,370, Notice of Allowance, dated Nov. 18, 2015, 5 pages.
U.S. Appl. No. 15/040,376, Non-Final Office Action, dated Mar. 11, 2016, 5 pages.
U.S. Appl. No. 15/040,376, Notice of Allowance, dated Aug. 15, 2016, 5 pages.
Adjei, et al., "A Phase I Trial of the Farnesyl Transferase Inhibitor SCH66336: Evidence for Biological and Clinical Activity", Cancer Research, 2000, 60, pp. 1871-1877.
Akaike, et al., "Antagonistic Action of Imidazolineoxyl N-Oxides against Endothelium-Derived Relaxing Factor/*NO through a Radical Reaction", Biochem. 1993, vol. 32, pp. 827-832.
Arnold, et al., "Nitric Oxide Activates Guanylate Cyclase and Increases Guanosine 3':5'-cyclic Monophosphate Levels in Various Tissue Preparations", Proc. Natl. Acad. Sci. 1977, vol. 74, pp. 3203-3207.
Artim, et al., "Nitro-oleic Acid Targets Transient Receptor Potential (TRP) Channels in Capsaicin Sensitive Afferent Nerves of Rat Urinary Bladder", Expt. Neurol. 2011, 232, pp. 90-99.
Baker, et al., "Fatty Acid Transduction of Nitric Oxide Signaling", J. Biol. Chem. 2005, vol. 280(51), pp. 42464-42475.
Baker, et al., "Red Cell Membrane and Plasma Linoleic Acid Nitration Products: Synthesis, Clinical Identification, and Quantitation", Proc. Natl. Acad. Sci. 2004, vol. 101(32), pp. 11577-11582.
Baker, et al., "Convergence of Nitric Oxide and Lipid Signaling: Anti-Inflammatory Nitro-Fatty Acids", Free Radic. Biol. Med. 2009, vol. 46, pp. 989-1003.
Baker, et al., "Nitro-Fatty Acid Reaction with Glutathione and Cysteine Kinetic Analysis of Thiol Alkylation by a Michael Addition Reaction", J. Biol. Chem. 2007, vol. 282, No. 2, pp. 31085-31093.
Balazy, "Isomerization and Nitration of Arachidonic Acid by Nitrogen Dioxide", Advances in Mass Spectrometry 2001, vol. 15, pp. 375-376.
Balazy, et al., "Vicinal Nitrohydroxyeicosatrienoic Acids: Vasodilatory Lipids Formed by Reaction of Nitrogen Dioxide with Arachidoonic Acid", J. Pharmacol. Exp. Ther. 2001, vol. 299(2), pp. 611-619.
Baldus, et al., "Endothelial Transcytosis of Myeloperoxidase Confers Specificity to Vascular ECM Proteins as Targets of Tyrosine Nitration", J. Clin. Invest. 2001, vol. 108(12), pp. 1759-1770.
Baldus, et al., "Is NO News Bad News in Acute Respiratory Distress Syndrome", Am. J. Respir. Crit. Care Med. 2001, vol. 163, pp. 308-310.
Ballini, et al., "(Z)-7-Nitro-3-Heptene as Central Intermediate for the Synthesis of Jasmine, Methyl Jasmonate and Gamma-Jasmolactone", Synthetic Communications, 1989, 16(3-4): pp. 575-583.
Bates, et al., "Nitroalkene Fatty Acids Mediate Activation of Nrf2/ARE-dependent and PPARgamma-dependent Transcription by Distinct Signaling Pathways and with Significantly Different Potencies", Biochem. 2011, 50, pp. 7765-7773.
Bates, et al., "Noncatalytic Interactions Between Glutathione S-Transferases and Nitroalkene Fatty Acids Modulate Nitroalkene-Mediated Activation of Peroxisomal Proliferator-Activated Receptor Gamma", Biochem. 2009, 48. pp. 4159-4169.
Batthyany, et al., "Reversible Post-Translational Modification of Proteins by Nitrated Fatty Acids In Vivo", J. Biol. Chem. 2006, vol. 281(29), pp. 20450-20463.
Beckman, et al., "Apparent Hydroxyl Radical Production by Peroxynitrite: Implications for Endothelial Injury from Nitric Oxide and Superoxide", Proc. Natl. Acad. Sci. 1990, vol. 87, pp. 1620-1624.
Bell-Parikh, et al., "Biosynthesis of 15-deoxy-delta12, 14-PGJ2 and the Ligation of PPARgamma", J. Clin. Invest. 2003, vol. 112(6), pp. 945-955.
Bjorn, "Clues Emerge About Benefits of Briefly Blocking Blood Flow", Nature 2009, vol. 15, No. 2, p. 132.
Blanco, et al., "6-Methylnitroarachidonate: A Novel Esterified Nitroalkene that Potently Inhibits Platelet Aggregation and Exerts cGMP-Mediated Vascular Relaxation", Free Radic. Biol. Med., 2011, 50, pp. 411-418.
Bligh & Dyer, "A Rapid Method of Total Lipid Extraction and Purification", J. Biochem. Physiol. 1959, vol. 37(8), pp. 911-917.
Bloodsworth, et al., "Nitric Oxide Regulation of Free Radical—and Enzyme-Mediated Lipid and Lipoprotein Oxidation," Arterioscler Thromb. Vasc. Biol. 2000, pp. 1707-1715.
Bonacci, et al."Gas-Phase Fragmentation Analysis of Nitro-Fatty Acids," J. Am. Soc. Mass, 2011, Spec. 22, pp. 1534-1551.
Borniquel, et al., "Nitrated Oleic Acid Up-Regulates PPARγ and Attenuates Experimental Inflammatory Bowel Disease," Free Radic. Bio. Med. 2010, 49, pp. 499-505.
Castro, et al., "Cytochrome c: a Catalyst and Target of Nitrate-Hydrogen Peroxide-Dependent Protein Nitration," Arch. Biochem. Biophys. 2004, vol. 421, pp. 99-107.
Chawla, et al., "PPAR-gamma Dependent and Independent Effects on Macrophage-Gene Expression in Lipid Metabolism and Inflammation," Nat. Med. 2001, vol. 7(1), pp. 48-52.
Chen, "Troglitazone Inhibits Atherosclerosis in Apolipoprotein E-Knockout Mice, Pleiotropic Effects on CD36 Expression and HDL", Arterioscler. Thromb. Vasc. Biol. 2001, vol. 21, pp. 372-377.
Chen, et al., "Peroxisome Proliferator-Activated Receptors and the Cardiovascular System" Vitam. Horm. 2003, vol. 66, pp. 157-188.
Claudel, et al., "Reduction of Atherosclerosis in Apolipoprotein E Knockout Mice by Activation of the Retinoid X Receptor" Proc. Natl. Acad. Sci. 2001, vol. 98(5), pp. 2610-2615.
Coffey, et al., "Catalytic Consumption of Nitric Oxide by 12/15-Lipoxygenase: Inhibition of Monocyte Soluble Guanylate Cyclase Activation" Proc. Natl. Acad. Sci. 2001, vol. 98(14), pp. 8006-8011.
Cole, et al., "Nitro-Fatty Acid Inhibition of Neointima Formation After Endoluminal Vessel Injury", Circ. Res. 2009, 105 (10), pp. 965-972.
Coles, et al., "Nitrolinoleate Inhibits Platelet Activation by Attenuating Calcium Mobilization and Inducing Phosphorylation of Vasodilator-Stimuted Phosphoprotein Through Elevation of cAMP" J. Biol. Chem. 2002, vol. 8(22), pp. 5832-5840.
Coles, et al., "Nitrolinoleate Inhibits Superoxide Generation, Degranulation and Integrin Expression by Human Neutrophils, Novel Antiinflammatory Properties of Nitric Oxide-Derived Reactive Species in Vascular Cels" Circ. Res. 2002, vol. 91, pp. 375-381.
Collins, et al., "Troglitazone Inhibits Formation of Early Atherosclerotic Lesions in Diabetic and Nondiabetic Low Density Lipoprotein Receptor-Deficient Mice," Arterioscler. Thromb. Vase. Biol. 2001, vol. 21, pp. 365-371.
Cosby, et al., "Nitrite Reduction to Nitric Oxide by Deoxyhemoglobin Vasodilates the Human Circulation," Nat. Med. 2003, vol. 9(12), pp. 1498-1505.
Cui, et al., "Nitrated Fatty Acids: Endogenous Anti-Inflammatory Signaling Mediators", J. Biol. Chem. 2006, vol. 281 (47), pp. 35686-35698.

(56) References Cited

OTHER PUBLICATIONS

Davies, et al., "Oxidized Alkyl Phospholipids are Specific, High Affinity Peroxisome Proliferator-Activated Receptor Gamma Ligands and Agonists", J. Biol. Chem. 2001, vol. 276, pp. 16015-16023.
Delerive, et al., "Oxidized Phospholipids Activated PPARα in a Phospholipase A2-Dependent Manner," FEBS Lett. 2000, vol. 471, pp. 34-38.
Denicola, et al., "Diffusion of Nitric Oxide in Low Density Lipoprotein," J. Biol. Chem. 2002, vol. 277(2), pp. 932-936.
Denicola, et al., "Diffusion of Perosynitrite Across Erythrocyte Membranes," Proc. Natl. Acad. Sci. 1998, vol. 95, pp. 3566-3571.
d'Ischia, "Oxygen-Dependent Nitration of Ethyl Linoleate with Nitric Oxide", Tetrahedron Lett. 1996, vol. 37, pp. 5773-5574.
d'Ishcia, et al., "Medium-Dependent Competitive Pathways in the Reactions of Polyunsaturated Fatty Acids with Nitric Oxide in the Presence of Oxygen. Structural Characterisation of Nitration Products and a Theoretical Insight" Tetrahedron 1999, vol. 55, pp. 9297-9308.
Dodge & Phillips, "Composition of Phospholipids and of Phospholipids Fatty Acids and Aldehydes in Human Red Cells" J. Lipid Res. 1967, vol. 8, pp. 667-675.
Easton, et al., "Polyunsaturated Nitroalkanes and Nitro-Substituted Fatty Acids" Synthesis 2001, vol. 3, pp. 451-457.
Eiserich, et al., "Myeloperoxidase, A Leukocyte-Derived Vascular NO Oxidase" Sci. 2002. vol. 296, pp. 2391-2394.
Eiserich, et al., "Pathophysiology of Nitric Oxide and Related Species: Free Radical Reactions and Modification of Biomolecules,", Molec. Aspects, Med., 1998, vol. 19, pp. 221-357.
Evans, et al., "PPARS and the Complex Journey to Obesity," Nat. Med. 2004, vol. 10(4), pp. 1-7.
Feelisch, et al., "Concomitant S-, N-, and heme-nitros(yl)ation in Biological Tissues and Fluids: Implications for the fate of NO In Vivo," 2002, FASEB J. 16, pp. 1775-1785.
Ferreira, et al., "Macrophage Activation Induces Formation of the Anti-Inflammatory Lipid Cholesteryl-Nitrolinoleate" Biochem. J. 2009, vol. 417, pp. 223-234.
Ferry, et al., "Binding of Prostaglandins to Human PPARgamma: Tool Assessment and New Natural Ligands" Eur. J. Pharmacol. 2001, vol. 417, pp. 77-89.
Finlayson-Pitts, et al., "A Fourier Transform Infrared Spectrometry Study of the Reactions of Phosphatidylcholines with Gaseous N2O5 and NO2" Toxicol. Appl. Pharmacol. 1987, vol. 89., pp. 438-448.
Forman, et al., "15-Deoxy-Delta12,14-Prostglandin J2 is a Ligand for the Adipocyte Determination Factory PPARgamma", Cell 1995, vol. 83, pp. 803-812.
Freeman, et al., "Nitro-Fatty Acid Formation and Signaling" J. Biol. Chem. 2008, vol. 283, n. 23, pp. 15515-15519.
Gallon & Pryor, "The Identification of the Allylic Nitrite and Nitro Derivatives of Methyl Linoleate and Methyl Linolenate by Negative Chemical Ionization Mass Spectroscopy," Lipids 1994, vol. 28(2), pp. 125-133.
Gallon & Pryor, "The Reaction of Low Levels of Nitrogen Dioxide with Methyl Linoleate in the Presence and Absence of Oxygen" Lipids 1994, vol. 29, pp. 171-176.
Gladwin, et al., "The Emerging Biology of the Nitrite Anion" Nature 2005, vol. 1, No. 6, pp. 308-314.
Gladwin, et al., "Role of Circulating Nitrite and S-Nitrosohemoglobin in the Regulation of Regional Blood Flow in Humans" Proc. Natl. Acad. Sci. 2000, vol. 97(21), pp. 11482-11487.
Gladwin, et al., "S-Nitrosohemoglobin IS Unstable in the Reductive Erythrocyte Environment and Lacks O2//NO-Linked Allosteric Function" J. Biol. Chem. 2002, vol. 277, pp. 27818-27828.
Goodman & Gilman's, "The Pharmacological Basis of Therapeutics," Ninth Edition, 1996, Appendix II, pp. 1707-1711.
Gorczynski, et al., "Regio-And Stereospecific Synthesis and Nitric Oxide Donor Properties of (E)-9-and (E)-10-Nitroctadec-9-Enoic Acids," Organic Letters 2006, vol. 8, No. 11, pp. 2305-2308.

Grisham, "Myoglobin-Catalyzed Hydrogen Peroxide Dependent Arachidonic Acid Peroxidation" Free Radic. Biol. Med. 1985, vol. 1, pp. 227-232.
Groeger & Freeman, "Signaling Actions of Electrophiles: Anti-Inflammatory Therapeutic Candidates," Molec. Interven., 2010, 10, pp. 39-50.
Guo, et al., "Atypical PKCzeta Transduces Electrophilic Fatty Acid Signaling in Pulmonary Epithelial Cells," Nitric Oxide, 2011, 25, pp. 366-372.
Gutierrez, et al., "Nitric Oxide Regulation of Superoxide-Dependent Lung Injury: Oxidant-Protection Actions of Endogenously Produced and Exogenously Administered Nitric Oxide" Free Radic. Biol. Med. 1996, vol. 21, No. 1, pp. 43-52.
Hogg, "The Biochemistry and Physiology of S-Nitrosothiols" Annu. Rev. Pharmacol. Toxicol. 2002, 42, pp. 585-600.
Hogg, et al., "Reactions of Nitric Oxide with Nitronyl Nitroxides and Oxygen: Prediction of Nitrate Formation by Kinetic Simulation" Free Radic. Res. 1995, vol. 22(1), pp. 47-56.
Hogg, et al., "Inhibition of Low-Density Lipoprotein Oxidation by Nitric Oxide Potential Role in Atherogenesis" FEBS Lett. 1993, vol. 334(2). pp. 170-174.
Ichikawa, et al., "Nitroalkenes Suppress Lipopolysacaharide-Induced Signal Transducer and Activator of Transcription Signaling in Macrophages" A Critical Role of Mitogen-Activated Protein Kinase Phophatase 1 Endocrinology 2008, 149(8), pp. 4086-4094.
Ignarro, et al., "Pharmacological Evidence that Endothelium-Derived Relaxing Factor is Nitric Oxide: Use of Pyrogallol and Superoxide Dismutase to Study Endothelium-Dependent and Nitric Oxide-Elicted Vascular Smooth Muscle Relaxation," J. Pharmacol. Exp. Ther. 1988, vol. 244(1), pp. 181-189.
Ignarro, et al., "Endothelium-Derived Relaxing Factor From Pulmonary Artery and Vein Possesses Pharmacologic and Chemical Properties Identical to Those of Nitric Oxide Radical" Circ. Res. 1987, vol. 61(6), pp. 866-879.
Iles, et al., "Fatty Acid Trasnduction of Nitric Oxide Signaling: Nitrolinoleic Acid Mediates Protective Effects through Regulation of the ERK Pathway" Free Radic. Biol. Med. 2009, vol. 46, pp. 866-875.
Janero, et al., "Differential Nitros(yl)ation of Blood and Tissue Constituents During Glyceral Trinitrate Biotransformation In Vivo," Proc. Natl. Acad. Sci. 2004, vol. 101(48), pp. 16958-16963.
Jourd'Heuil, et al., "The Oxidative and Nitrosative Chemistry of the Nitric Oxide/Superoxide Reaction in the Presence of Biocarbonate" Arch. Biochem. Biophys. 1999, vol. 365(1), pp. 92-100.
Kansanen, et al., "Nrf2-Dependent and -Independent Responses to Nitro-Fatty Acids in Human Endothelial Cells: Identification of Heat Shock Response as the Major Pathway Activated by Nitro-oleic Acid" J. Biol. Chem. 2009, pp. 1-34.
Karp, et al., "Clinical and Biologic Activity of the Farnesyltransferase Inhibitor R115777 in Adults with Refractory and Relapsed Acute Leukemias: A Phase 1 Clinical-Laboratory Correlative Trial," Blood, 2001, 97(11), pp. 3361-3369.
Kelley, et al., "Nitro-oleic Acid, A Novel and Irreversible Inhibitor of Xanthine Oxidoreductase" J. Biol. Chem. 2008, 283, pp. 36176-36184.
Khoo & Freeman, "Activation of Vascular Endothelial Nitric Oxide Synthase and Heme Oxygenase-1 Expression by Electrophilic Nitro-Fatty Acids," Free Radic. Bio. Med. 2010, 48, pp. 230-239.
Khoo & Freeman, "Electrophilic Nitro-Fatty Acids: Anti-Inflammatory Mediators in the Vascular Compartment", Curr. Opn. Pharml. 2010, 10, pp. 179-184.
Kissner, et al., "Formation and Properties of Peroxynitrite as Studied by Laser Flash Photolysis, High-Pressure Stopped-Flow Technique, and Pulse Radiolysis" Chem. Res. Toxicol. 1997, vol. 10, pp. 1285-1292.
Kliewer, et al., "A Prostaglandin J2 Metabolite Binds Peroxisome Proliferatory-Activated Receptor Gamma and Promotes Adipocyte Differentiation," Cell 1995, vol. 83, pp. 813-819.
Kliewer, et al., "Fatty Acids and Eicosanoids Regulate Gene Expression Through Direct Interactions and Peroxisome Proliferators-Activated Receptors Alpha and Gamma," Proc. Natl. Acad. Sci. 1997, vol. 94. pp. 4318-4323.

(56) References Cited

OTHER PUBLICATIONS

Kobayshi, "The Reaction of Nitrogen Dioxide with Lung Surface Components: The Reaction with cis-9-Octadecenoic Acid" Chemosphere 1983, vol. 12(9/10), pp. 1317-1325.

Koenitzer, et al., "Redox Signaling in Inflammation: Interactions of Endogenous Electrophiles and Mitochondria in Cardiovascular Disease", 2010, Ed. Laskin, et al., 1203, pp. 45-52.

Lai, et al., "Reactions of Dinitrogen Pentoxide and Nitrogen Dioxide" Lipids 1991, vol. 26(4). pp. 306-314, Abstract.

Larfars, et al., "Activation of Nitric Oxide Release and Oxidative Metabolism by Leukotrienes B4, C4, and D4 in Human Polymorphonuclear Leukocytes," Blood 1999, vol. 93(4), pp. 1399-1405.

Lee & Evans, "Peroxisome Proliferators-Activated Receptor-Gamma in Macrophage Lipid Homeostasis," Trends Endocrinol. Metab. 2002, vol. 13(8), pp. 331-335.

Levy, et al., "Lipid Mediator Class Switching During Acute Inflammation; Signals in Resolution", Nat. Immunol. 2001, vol. 2 pp. 612-619.

Li, et al., "Differential Inhibition of Macrophage Foam-Cell Formation and Atherosclerosis in Mice by PPARalpha, beta/delta, and gamma", J. Clin. Invest. 2004, vol. 114(11), pp. 1564-1576.

Li, et al., "Molecular Recognition of Nitrated Fatty Acids by PPARγ", Nat. Struct. Mol. Biol. 15, pp. 865-873.

Lim, et al., "Nitrolinoleate, A Nitric Oxide-Derived Mediator of Cell Function: Synthesis, Characterization, and Vasomotor Activity," Proc. Natl. Acad. Sci. 2002, vol. 99, pp. 15941-15946.

Lima, et al., "Characterizaation of Linoleic Acid Nitration in Human Blood Plasma by Mass Spectrometry," Biochem. 2002, vol. 41, pp. 10717-10722.

Liu, et al., "Accelerated Reaction of Nitric Oxide with O2 Within the Hydrophic Interior of Biological Membranes," Proc. Natl. Acad. Sci. 1998, vol. 95, pp. 2175-2179.

\* cited by examiner

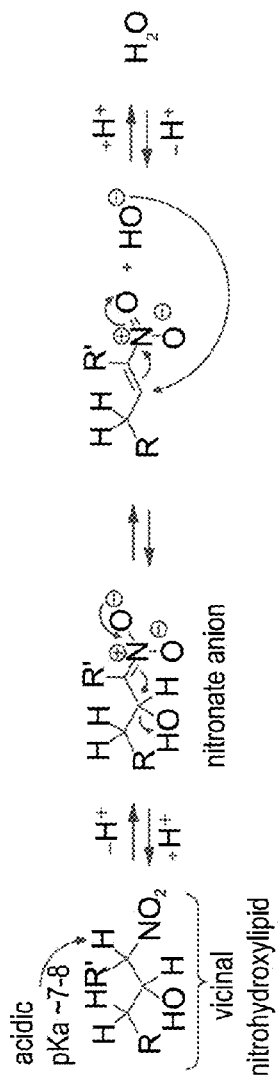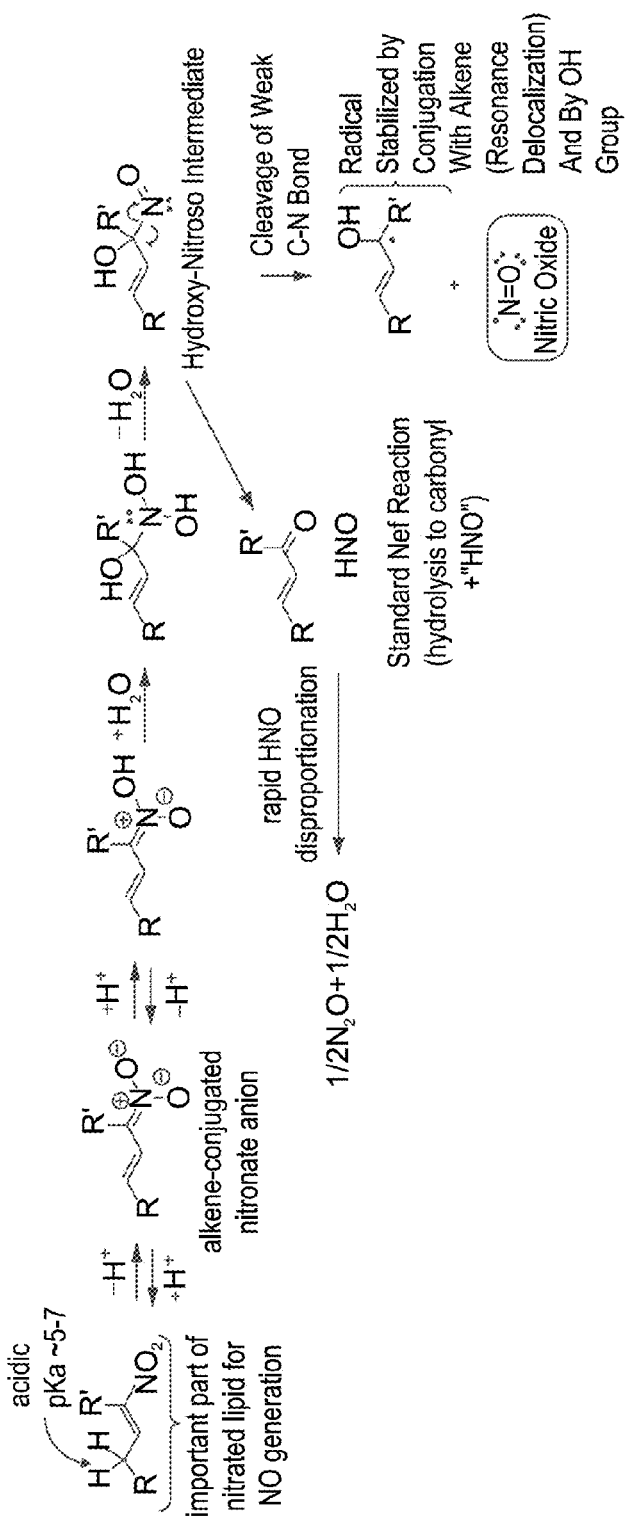
FIG. 29

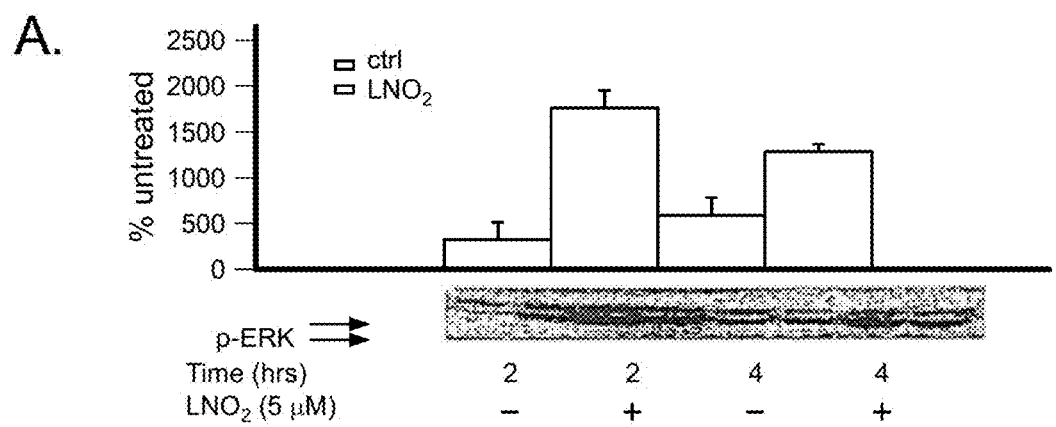
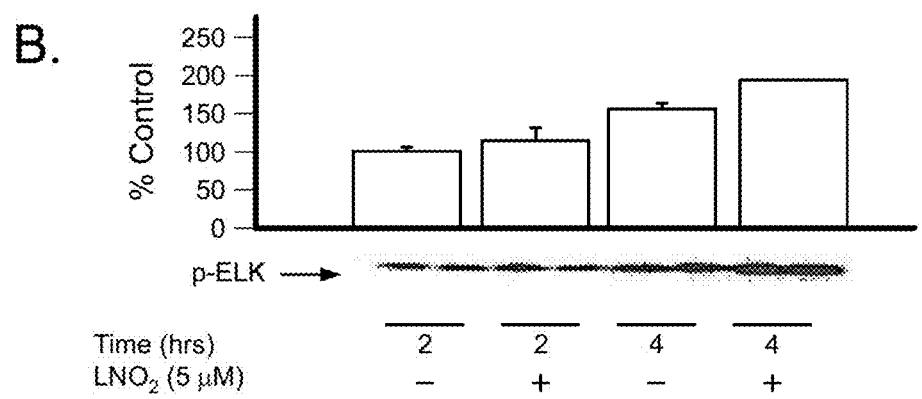
Figure 31

NITRATED LIPIDS AND METHODS OF MAKING AND USING THEREOF

CROSS REFERENCE TO RELATED APPLICATIONS

This application is a continuation of U.S. patent application Ser. No. 15/040,376, filed Feb. 10, 2016, which is a continuation of U.S. patent application Ser. No. 14/638,370, filed Mar. 4, 2015, now U.S. Pat. No. 9,295,678, which is a continuation of U.S. patent application Ser. No. 13/646,985, filed Oct. 8, 2012, now U.S. Pat. No. 9,006,473, which is a continuation of U.S. patent application Ser. No. 12/797,460, filed Jun. 9, 2010, now U.S. Pat. No. 8,309,526, which is a division of U.S. patent application Ser. No. 11/568,377, filed Oct. 26, 2006, now U.S. Pat. No. 7,776,916, which is a national phase application of International Patent Application No. PCT/US05/14305 filed Apr. 26, 2005, which claims priority to U.S. Patent Application Ser. No. 60/566,005, filed Apr. 28, 2004, the entire disclosures of which are hereby incorporated by reference in their entireties for all purposes.

ACKNOWLEDGEMENTS

This invention was made with government support under Grant Numbers RO1HL58115 and RO1HL64937 awarded by the National Institutes of Health. The government has certain rights in the invention.

BACKGROUND

Nitric oxide (•NO) is an endogenously generated, lipophilic signaling molecule that maintains vascular homeostasis via stimulation of soluble guanylate cyclase (1). In addition to mediating vascular relaxation, •NO potently modulates oxygen radical reactions, inflammatory cell function, post-translational protein modification and regulation of gene expression (2-5). There are multiple pathways whereby •NO-derived species can mediate the oxidation and nitration of biomolecules such as unsaturated fatty acids. Nitric oxide reacts at diffusion-limited rates with superoxide ($O_2^{\bullet-}$, k=$1.9 \times 10^{10}$ $M^{-1}$ $sec^{-1}$) to yield peroxynitrite ($ONOO^-$) and its conjugate acid, peroxynitritous acid (ONOOH), the latter of which undergoes homolytic scission to nitrogen dioxide (•$NO_2$) and hydroxyl radical (•OH) (2, 6). Also, biological conditions favor the reaction of $ONOO^-$ with $CO_2$, yielding nitrosoperoxycarbonate ($ONOOCO_2^-$; k=$3 \times 10^4$ $M^{-1}$ $sec^{-1}$), which rapidly yields •$NO_2$ and carbonate (•$CO_3^-$) radicals via homolysis, or rearrangement to $NO_3^-$ and $CO_2$ (7). During inflammation, neutrophil myeloperoxidase and heme proteins such as myoglobin and cytochrome c catalyze $H_2O_2$-dependent oxidation of nitrite ($NO_2^-$) to •$NO_2$, resulting in biomolecule oxidation and nitration that is influenced by the spatial distribution of catalytic heme proteins (8-11). Finally, even though the rate of reaction of •NO with $O_2$ is slow, (k=$2 \times 10^6$ $M^{-2}$ $sec^{-1}$) the small molecular radius, uncharged nature and lipophilicity of •NO and $O_2$ facilitate their diffusion and concentration in membranes and lipoproteins up to 20-fold (12-14). This "molecular lens" effect induced by •NO and $O_2$ solvation in hydrophobic cell compartments accelerates the reaction of •NO with $O_2$ to yield $N_2O_3$ and $N_2O_4$. As a result of these various reactions, a rich spectrum of primary and secondary reactions yield products capable of concerted oxidation, nitrosation and nitration of target molecules.

Multiple mechanisms can account for the nitration of fatty acids by •$NO_2$ (15-20). During both basal cell signaling and tissue inflammatory conditions, •$NO_2$ generated by the aforementioned reactions can react with membrane and lipoprotein lipids. Environmental sources also yield •$NO_2$ as a product of photochemical air pollution and tobacco smoke. In both in vivo and in vitro systems, •$NO_2$ has been shown to initiate auto-oxidation of polyunsaturated fatty acids via hydrogen abstraction from the bis-allylic carbon to form nitrous acid and a resonance-stabilized allylic radical (21). Depending on the radical environment, the lipid radical species can react with molecular oxygen to form a peroxyl radical. During inflammation or ischemia, when $O_2$ levels are lower, lipid radicals can react to an even greater extent with •$NO_2$ to generate multiple nitration products including singly nitrated, nitrohydroxy- and dinitro-fatty acid adducts (18, 19, 21). These products can be generated via either hydrogen abstraction or direct addition of •$NO_2$ across the double bond. Hydrogen abstraction causes a rearrangement of the double bonds to form a conjugated diene; however, the addition of •$NO_2$ maintains a methylene-interrupted diene configuration to yield singly nitrated polyunsaturated fatty acids (18). This arrangement is similar to nitration products generated by the nitronium ion ($NO_2^+$), which can be produced by $ONOO^-$ reaction with heme proteins or via secondary products of $CO_2$ reaction with $ONOO^-$ (20).

Reaction of polyunsaturated fatty acids with acidified nitrite ($HNO_2$) generates a complex mixture of products similar to those formed by direct reaction with •$NO_2$, including the formation of singly nitrated products that maintain the bis-allylic bond arrangement (18, 19). The acidification of $NO_2^-$ creates a labile species, $HNO_2$, which is in equilibrium with secondary products, including $N_2O_3$, •NO and •$NO_2$, all of which can participate in nitration reactions. The relevance of this pathway as a mechanism of fatty acid nitration is exemplified by physiological and pathological conditions wherein $NO_2^-$ is exposed to low pH (e.g., <pH 4.0). This may conceivably occur in the gastric compartment, following endosomal or phagolysosomal acidification or in tissues following-post ischemic reperfusion.

Nitrated linoleic acid ($LNO_2$) displays robust cell signaling activities that (at present) are anti-inflammatory in nature (20, 22-25). Synthetic $LNO_2$ inhibits human platelet function via cAMP-dependent mechanisms (26) and inhibits neutrophil $O_2^{\bullet-}$ generation, calcium influx, elastase release, CD11b expression and degranulation via non-cAMP, non-cGMP-dependent mechanisms (27). $LNO_2$ also induces vessel relaxation in part via cGMP-dependent mechanisms (22, 28). In aggregate, these data, derived from a synthetic fatty acid adduct, infer that $LNO_2$ species represent a novel class of lipid-derived signaling mediators. To date, a gap in the clinical detection and structural characterization of nitrated fatty acids has limited defining $LNO_2$ derivatives as biologically-relevant lipid signaling mediators that converge •NO and oxygenated lipid signaling pathways.

Therefore, it would be advantageous to produce nitrated lipids in substantially pure form so that their cell signaling activities can be characterized and their purified derivatives can be used to treat various diseases. Described herein are nitrated lipids and methods for producing nitrated lipids in pure form. Also described herein are methods for using the nitrated lipids to treat various diseases.

SUMMARY

Described herein are nitrated lipids and methods of making and using the nitrated lipids. The advantages of the invention will be set forth in part in the description which follows, and in part will be obvious from the description, or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

BRIEF DESCRIPTION OF THE DRAWINGS

The accompanying drawings, which are incorporated in and constitute a part of this specification, illustrate several embodiments of the invention and together with the description, serve to explain the principles of the invention.

FIG. 29 shows Scheme 2, possible mechanisms for NO formation by $LNO_2$. (Stage 1) Due to the strong electrophilic nature of the carbon adjacent to the nitroalkene and the acidity of its bound hydrogen, the vicinal nitrohydroxy fatty acid derivative is in equilibrium with the nitroalkene. (Stage 2) The mechanism of ·NO release from $LNO_2$ can result from the formation of a nitroso intermediate formed during aqueous $LNO_2$ decay. This nitroso intermediate is expected to have an especially weak C—N bond, easily forming ·NO and a radical stabilized by conjugation with the alkene and stabilized by the OH group, a moiety known to stabilize adjacent radicals.

FIG. 31 shows that nitroalkenes activate the ERK MAPK pathway in human lung epithelial cells, as shown by a dramatic increase in ERK phosphorylation (e.g., activation) and the phosphorylation of its downstream target signaling protein, pELK. The activation of these cell signaling mediators will profoundly impact on cell inflammatory responses, proliferation and differentiation. This example shows human lung epithelial cell responses of p-JNK and p-c-Jun.

DETAILED DESCRIPTION

Figure 1:
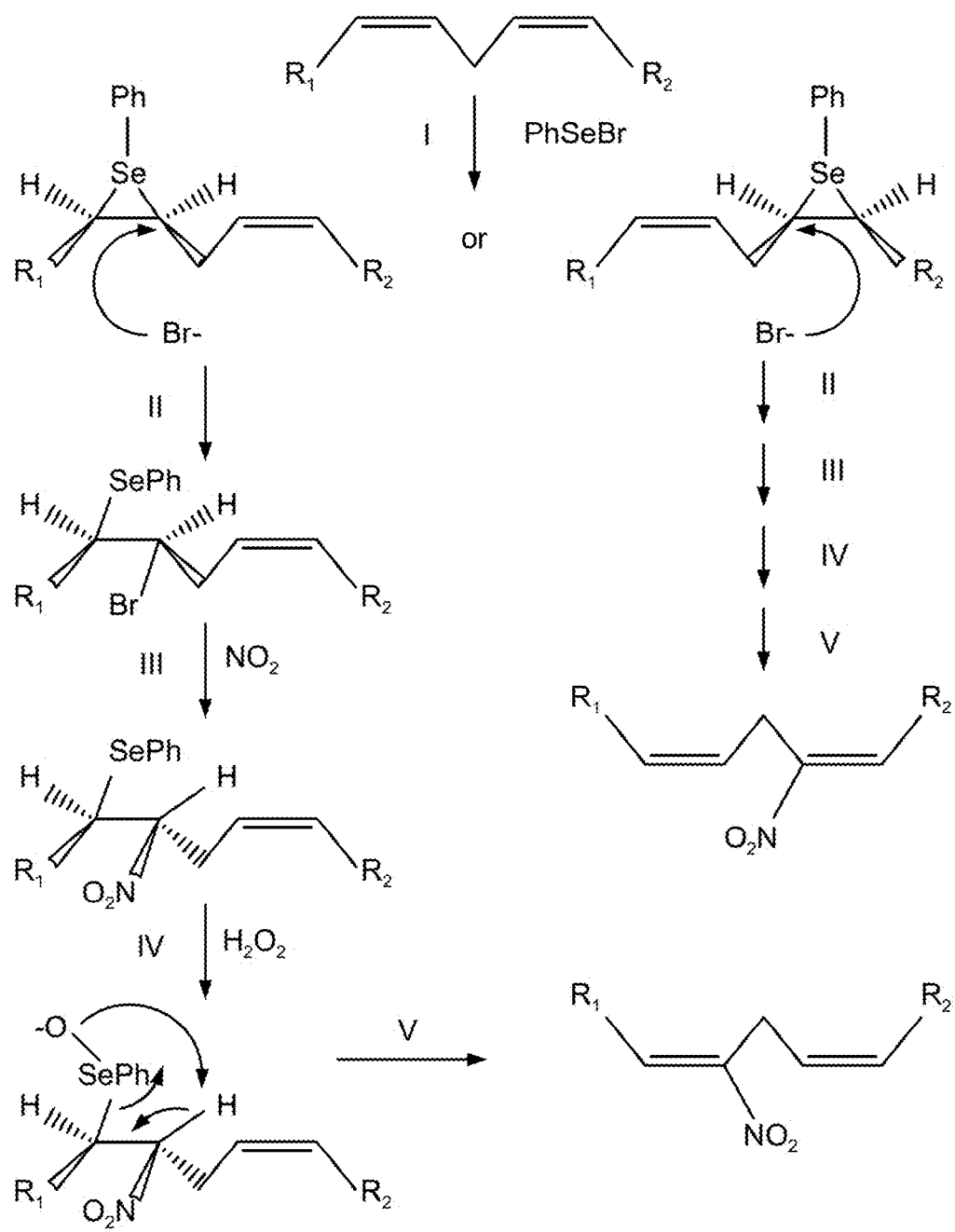
FIG. 1 shows a reaction scheme for producing nitrated lipids.

Before the present compounds, compositions, and/or methods are disclosed and described, it is to be understood that the aspects described below are not limited to specific compounds, synthetic methods, or uses as such may, of course, vary. It is also to be understood that the terminology used herein is for the purpose of describing particular aspects only and is not intended to be limiting.

In this specification and in the claims that follow, reference will be made to a number of terms that shall be defined to have the following meanings:

It must be noted that, as used in the specification and the appended claims, the singular forms "a," "an" and "the" include plural referents unless the context clearly dictates otherwise. Thus, for example, reference to "a pharmaceutical carrier" includes mixtures of two or more such carriers, and the like.

"Optional" or "optionally" means that the subsequently described event or circumstance can or cannot occur, and that the description includes instances where the event or circumstance occurs and instances where it does not. For example, the phrase "optionally substituted lower alkyl" means that the lower alkyl group can or can not be substituted and that the description includes both unsubstituted lower alkyl and lower alkyl where there is substitution.

Ranges may be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

References in the specification and concluding claims to parts by weight, of a particular element or component in a composition or article, denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent of a component, unless specifically stated to the contrary, is based on the total weight of the formulation or composition in which the component is included.

Variables such as $R^1$-$R^{16}$ used throughout the application are the same variables as previously defined unless stated to the contrary.

By "subject" is meant an individual. The subject can be a mammal such as a primate or a human. The term "subject" can include domesticated animals including, but not limited to, cats, dogs, etc., livestock (e.g., cattle, horses, pigs, sheep, goats, etc.), and laboratory animals (e.g., mouse, rabbit, rat, guinea pig, etc.).

By "contacting" is meant an instance of exposure by close physical contact of at least one substance to another substance. For example, contacting can include contacting a substance, such as a pharmacologic agent, with a cell. A cell can be contacted with a test compound, for example, a nitrated lipid, by adding the agent to the culture medium (by continuous infusion, by bolus delivery, or by changing the medium to a medium that contains the agent) or by adding the agent to the extracellular fluid in vivo (by local delivery, systemic delivery, intravenous injection, bolus delivery, or continuous infusion). The duration of contact with a cell or group of cells is determined by the time the test compound is present at physiologically effective levels or at presumed physiologically effective levels in the medium or extracellular fluid bathing the cell.

"Treatment" or "treating" means to administer a composition to a subject or a system with an undesired condition (e.g., inflammation) or at risk for the condition. The condition can include a disease or a predisposition to a disease. The effect of the administration of the composition to the subject can have the effect of but is not limited to reducing or preventing the symptoms of the condition, a reduction in the severity of the condition, or the complete ablation of the condition.

By "effective amount" is meant a therapeutic amount needed to achieve the desired result or results, e.g., increasing the expression of a gene, inhibiting $Ca^{+2}$ mobilization in a cell, inhibiting degranulation or CD11b expression in a neutrophil, etc.

Herein, "inhibition" or "suppression" means to reduce activity as compared to a control. It is understood that inhibition or suppression can mean a slight reduction in activity to the complete ablation of all activity. An "inhibitor" or "suppressor" can be anything that reduces the targeted activity.

Herein, "induce" means initiating a desired response or result that was not present prior to the induction step. The term "potentiate" means sustaining a desired response at the same level prior to the potentiating step or increasing the desired response over a period of time.

The term "alkyl group" as used herein is a branched or unbranched saturated hydrocarbon group of 1 to 24 carbon atoms, such as methyl, ethyl, n-propyl, isopropyl, n-butyl, isobutyl, t-butyl, pentyl, hexyl, heptyl, octyl, decyl, tetradecyl, hexadecyl, eicosyl, tetracosyl and the like. A "lower alkyl" group is an alkyl group containing from one to six carbon atoms.

The term "alkenyl group" is defined as a branched or unbranched hydrocarbon group of 2 to 24 carbon atoms and structural formula containing at least one carbon-carbon double bond.

The term "alkynyl group" is defined as a branched or unbranched hydrocarbon group of 2 to 24 carbon atoms and a structural formula containing at least one carbon-carbon triple bond.

The term "ester" is represented by the formula —OC(O)R, where R can be an alkyl, alkenyl, or group described above.

$R^1$-$R^{16}$ can, independently, possess two or more of the groups listed above. For example, if $R^1$ is a straight chain alkyl group, one of the hydrogen atoms of the alkyl group can be substituted with an ester group. Depending upon the groups that are selected, a first group may be incorporated within second group or, alternatively, the first group may be pendant (i.e., attached) to the second group. For example, with the phrase "an alkyl group comprising an ester group," the ester group may be incorporated within the backbone of alkyl group. Alternatively, the ester can be attached the backbone of the alkyl group. The nature of the group(s) that is (are) selected will determine if the first group is embedded or attached to the second group.

Disclosed are compounds, compositions, and components that can be used for, can be used in conjunction with, can be used in preparation for, or are products of the disclosed methods and compositions. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a number of different nucleosides and polymeric substrates are disclosed and discussed, each and every combination and permutation of the nucleoside and the polymeric substrate are specifically contemplated unless specifically indicated to the contrary. Thus, if a class of molecules A, B, and C are disclosed as well as a class of molecules D, E, and F and an example of a combination molecule, A-D is disclosed, then even if each is not individually recited, each is individually and collectively contemplated. Thus, in this example, each of the combinations A-E, A-F, B-D, B-E, B-F, C-D, C-E, and C-F are specifically contemplated and should be considered disclosed from disclosure of A, B, and C; D, E, and F; and the example combination A-D. Likewise, any subset or combination of these is also specifically contemplated and disclosed. Thus, for example, the sub-group of A-E, B-F, and C-E are specifically contemplated and should be considered disclosed from disclosure of A, B, and C; D, E, and F; and the example combination A-D. This concept applies to all aspects of this disclosure including, but not limited to, steps in methods of making and using the disclosed compositions. Thus, if there are a variety of additional steps that can be performed it is understood that each of these additional steps can be performed with any specific embodiment or combination of embodiments of the disclosed methods, and that each such combination is specifically contemplated and should be considered disclosed.

I. Nitrated Lipids

In one aspect, the nitrated lipids described herein are lipids comprising at least one nitro group ($NO_2$) covalently bonded to the lipid, wherein the nitrated lipid is substantially pure. The term "substantially pure" as defined herein is a nitrated lipid that exists predominantly as one species. In certain aspects, nitration of a lipid can produce two or more nitration products. For example, the lipid can be nitrated one or more times at different positions on the lipid. These are referred to as positional isomers. Additionally, if the lipid contains a carbon-carbon double bond, the stereochemistry about the carbon-carbon double bond can also vary. These are referred to as stereoisomers. The nitrated lipids described herein are substantially one compound (positional and stereoisomer). In one aspect, the nitrated lipid is 90%, 92%, 94%, 96%, 98%, 99%, 99.5%, or 100% one compound.

In one aspect, the nitrated lipids possess at least one allylic or vinyl nitro group. The phrase "allylic nitro group" has the general formula —C=C—C—($NO_2$). The phrase "vinyl nitro group" has the general formula —C=C—($NO_2$). In one aspect, the nitrated lipid possesses only one allylic nitro group. In another aspect, the nitrated lipid possesses only one vinyl nitro group. In another aspect, the nitrated lipid possesses one or more allylic nitro groups and/or one or more vinyl nitro groups.

Lipids known in the art can be nitrated using the techniques described herein to produce nitrated lipids. In general, lipids useful for producing the nitrated lipid include, but are not limited to, fats and fat derived materials. In one aspect, the nitrated lipid can include, but is not limited to, a nitrated fatty acid or ester thereof, a nitrated fatty alcohol, or a nitrated sterol. In another aspect, the nitrated lipid can be a nitrated complex lipid. Examples of complex lipids include, but are not limited to, glycerolipids (e.g., compounds having a glycerol backbone including, but not limited to, phospholipids, glycolipids, monoglycerides, diglycerides, triglycerides) or cholesterol (e.g., cholesterols having fatty acids attached to it such as cholesterol linoleate). In one aspect, the nitrated lipid comprises a fatty acid having at least one ester linkage [—O—C=O(R)], ether group (C—O—R) or vinyl ether group (C—O—C=C—R). Examples of lipids having at least one ether group or vinyl ether group that can be nitrated are depicted below in A and B, respectively.

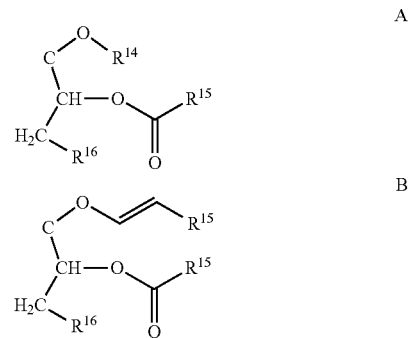

wherein
$R^{14}$ comprises $C_{16}$-$C_{22}$ alkyl, $C_{16}$-$C_{22}$ alkenyl, or $C_{16}$-$C_{22}$ alkynyl;
$R^{15}$ comprises $C_1$-$C_{20}$ alkyl, $C_1$-$C_{20}$ alkenyl, or $C_1$-$C_{20}$ alkynyl; and
$R^1$ comprises $C_1$-$C_{24}$ alkyl, $C_1$-$C_{24}$ alkenyl, or $C_1$-$C_{24}$ alkynyl.

In one aspect, the nitrated lipid is composed of a fatty acid having at least one carbon-carbon double bond. In one aspect, the nitrated lipid can be a nitrated fatty acid such as, for example, 14:1, 16:1, 18:1 (oleic acid ),18:2 (linoleic acid), 18:3 (linolenic acid), 20:4 (arachidonic acid), 22:6, or docosahexanoic acid, where the first number indicates the carbon chain length of the fatty acid, and the second number indicates the number of carbon-carbon double bonds present in the fatty acid.

In one aspect, the nitrated lipid can have the formula I

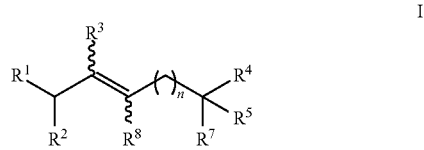

wherein
$R^1$ comprises $C_1$-$C_{24}$ alkyl, $C_1$-$C_{24}$ alkenyl, or $C_1$-$C_{24}$ alkynyl;
$R^2$, $R^3$, $R^7$, and $R^8$ comprise, independently, hydrogen, $NO_2$, OH, or OOH;
$R^4$ comprises $C_1$-$C_{24}$ alkyl, $C_1$-$C_{24}$ alkenyl, or $C_1$-$C_{24}$ alkynyl;

wherein $R^4$ comprises a terminal $COOR^6$ group, wherein $R^6$ comprises hydrogen, $C_1$-$C_{24}$ alkyl, or a pharmaceutically acceptable counterion, wherein $R^4$ optionally comprises one or more $NO_2$, OH, or OOH groups;

$R^5$ comprises hydrogen or $R^4$ and $R^5$ collectively forms =$C(R^9)(R^{10})$, wherein $R^9$ comprises $C_1$-$C_{24}$ alkyl, $C_1$-$C_{24}$ alkenyl, or $C_1$-$C_{24}$ alkynyl, wherein $R^9$ comprises a terminal $COOR^6$ group, wherein $R^9$ optionally comprises one or more $NO_2$, OH, or OOH groups;

$R^{10}$ comprises hydrogen, $NO_2$, OH, or OOH; and n is from 1 to 24;

wherein the nitrated lipid comprises at least one $NO_2$ group, wherein the nitrated lipid is substantially pure. In this aspect, the stereochemistry about the carbon-carbon double bond is substantially cis (or Z) or substantially trans (or E).

In another aspect, the nitrated lipid can have the formula II

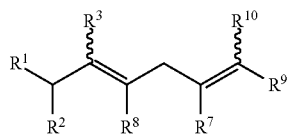

wherein $R^3$ is trans or cis to $R^8$, and $R^7$ is trans or cis to $R^{10}$, wherein the nitrated lipid is substantially pure. In this aspect, the stereochemistry about the carbon-carbon double bond is substantially cis (or Z) or substantially trans (or E). In one aspect, when the nitrated lipid has the formula II, $R^1$ comprises a $C_4$-$C_{10}$ alkyl group, $R^2$, $R^3$, $R^8$, and $R^{10}$ are hydrogen, $R^7$ is $NO_2$, and $R^9$ comprises a $C_6$-$C_{12}$ alkyl group. This class of nitrated lipids is depicted below, where the nitrated lipid has one vinyl nitro group.

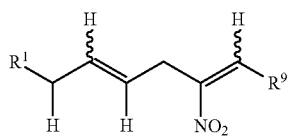

Figure 4:
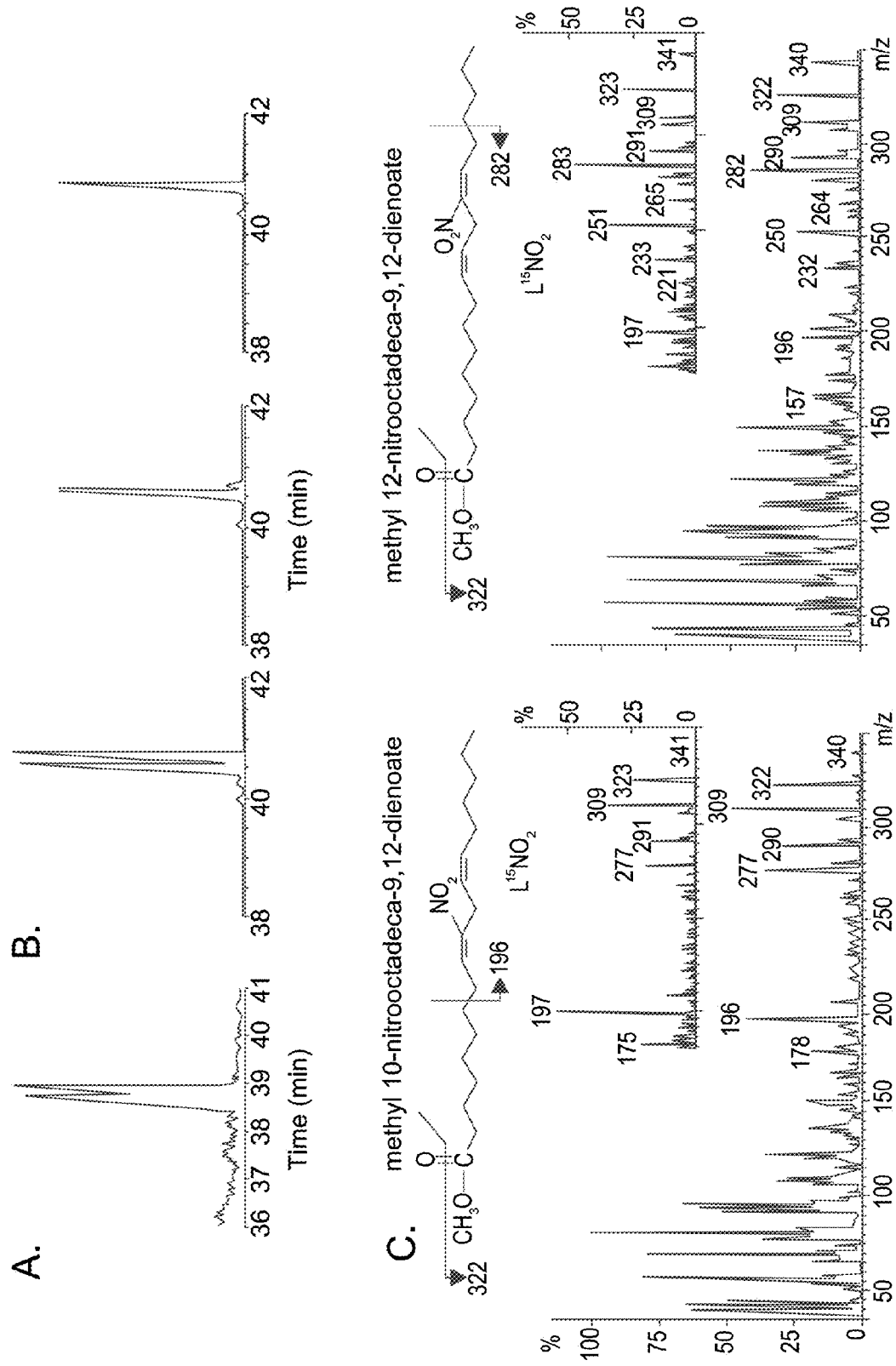
FIG. 4 shows the characterization of nitrated linoleic acid by GC mass spectrometry.

In a further aspect, when the nitrated lipid has the formula II, $R^3$ and $R^8$ are cis (Z) to one another, and $R^7$ and $R^{10}$ are cis (Z) to one another. In another aspect, the nitrated lipid is 10-nitro-9-cis,12-cis-octadecadienoic acid, which is depicted in FIG. 4C.

In another aspect, when the nitrated lipid has the formula II, $R^1$ comprises a $C_4$-$C_{10}$ alkyl group, $R^2$, $R^3$, $R^7$, and $R^{10}$ are hydrogen, $R^8$ is $NO_2$, and $R^9$ comprises a $C_6$-$C_{12}$ alkyl group. This class of nitrated lipids is depicted below, where the nitrated lipid has one vinyl nitro group.

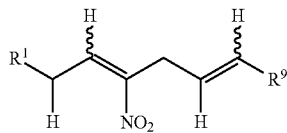

In a further aspect, $R^3$ and $R^8$ are cis (Z) to one another and $R^7$ and $R^{10}$ are cis (Z) to one another. In another aspect, the nitrated lipid is 12-nitro-9-cis,12-cis-octadecadienoic acid, which is depicted in FIG. 4C.

In another aspect, the nitrated lipid has the formula III

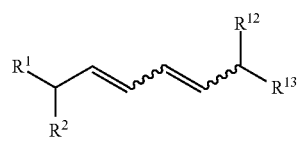

wherein $R^1$ comprises $C_1$-$C_{24}$ alkyl, $C_1$-$C_{24}$ alkenyl, or $C_1$-$C_{24}$ alkynyl;

$R^2$ and $R^{12}$ comprise, independently, hydrogen, $NO_2$, OH, or OOH; and $R^{13}$ comprises $C_1$-$C_{24}$ alkyl, $C_1$-$C_{24}$ alkenyl, or $C_1$-$C_{24}$ alkynyl, wherein $R^{13}$ comprises a terminal $COOR^6$ group, wherein $R^6$ comprises hydrogen, $C_1$-$C_{24}$ alkyl, or a pharmaceutically acceptable counterion, wherein $R^{13}$ optionally comprises one or more $NO_2$, OH, or OOH groups;

wherein the compound comprises at least one $NO_2$ group, wherein the nitrated lipid is substantially pure.

In another aspect, when the nitrated lipid has the formula III, $R^1$ comprises a $C_4$-$C_{10}$ alkyl group, $R^2$ is hydrogen, $R^{12}$ is $NO_2$, and $R^{13}$ comprises a $C_6$-$C_{12}$ alkyl group. This class of nitrated lipids is depicted below, where the nitrated lipid has one allylic nitro group.

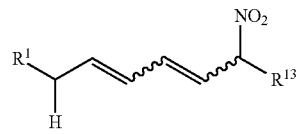

In this aspect, $R^1$ comprises a $C_4$-$C_{10}$ alkyl group, $R^2$ is $NO_2$, $R^{12}$ is hydrogen, and $R^{13}$ comprises a $C_6$-$C_{12}$ alkyl group. In one aspect, the nitrated lipid is 9-nitro-10,12-cis-octadecadienoic acid; 9-nitro-10,12-trans-octadecadienoic acid; 13-nitro-10, 12-cis-octadecadienoic acid; or 13-nitro-10, 12-trans-octadecadienoic acid.

Methods for preparing the nitrated lipids described herein are described below and in the Examples section.

II. Synthesis of Nitrated Lipids

Described herein are methods for preparing nitrated lipids. In one aspect, the method comprises (a) reacting an unsaturated lipid with a mercuric salt, a selenium compound, and a nitrating compound to produce a first intermediate, and (b) reacting the first intermediate with an oxidant.

Any of the lipids described above can be used to produce the nitrated lipids described herein. In one aspect, any unsaturated lipid having at least one carbon-carbon double bond can be used in this aspect to produce nitrated lipids.

In one aspect, step (a) can be performed in situ without isolation of the first intermediate. In another embodiment, the first intermediate can be trapped prior to step (b). The mercuric salt, a selenium compound, and a nitrating compound can be added in any order to the unsaturated lipid.

The selenium compound is any compound that is capable of reacting or interacting with the unsaturated group present in the lipid. In one aspect, when the unsaturated lipid possesses a carbon-carbon double bond, the selenium compound can form a three-membered ring intermediate, which is depicted, for example, in FIG. 1. In one aspect, the selenium compound possesses a leaving group capable of reacting with the three ring intermediate. Examples of leaving groups include, but are not limited to, halides (e.g., F, Cl, Br, I) and esters (e.g., acetate). Not wishing to be bound by theory, it is believed that the leaving group reacts with the three-membered ring intermediate to open the ring to produce a selenium-leaving group intermediate. One example of this intermediate is depicted in FIG. 1, where Br is the leaving group. Examples of selenium compounds useful herein include, but are not limited to, PhSeBr, PhSeCl, PhSeO$_2$CCF$_3$, PhSeO$_2$H, or PhSeCN.

The mercuric salt used in the methods described herein can be any mercuric salt known in the art. Not wishing to be bound by theory, it is believed that the mercuric salt facilitates the formation of the selenium three-membered ring intermediate. In one aspect, the mercuric salt comprises HgCl$_2$, Hg(NO$_3$)$_2$, or Hg(OAc)$_2$.

The nitrating compound is any compound that provides a source of NO$_2^-$ ions in solution. Not wishing to be bound by theory, it is believed that NO$_2^-$ reacts with the selenium intermediate formed upon the reaction between the unsaturated lipid and selenium compound by displacing the leaving group present in the intermediate. FIG. 1 depicts one aspect of this, where NO$_2^-$ displaces Br$^-$ by nucleophilic attack to produce a selenium/nitro intermediate. In one aspect, the nitrating compound can be any nitrite salt. In another aspect, the nitrating compound comprises NaNO$_2$ or AgNO$_2$.

The relative amounts of unsaturated lipid, selenium compound, mercuric salt, and nitrating compound can vary depending upon the specific reagents that are selected and reaction conditions. In one aspect, an equimolar amount or slight excess thereof of selenium compound, mercuric salt, and nitrating compound relative to the unsaturated lipid can be used. Step (a) is generally performed in a solvent, such as, for example, a polar or unpolar organic solvent. Examples of solvents useful herein include, but are not limited to, nitriles, ethers, esters, alkanes, alcohols, or combinations thereof. In one aspect, the solvent used in step (a) can be THF/acetonitrile. Step (a) can be performed at various temperatures depending upon the starting materials that are selected. In one aspect, the step (a) can be performed at room temperature.

By varying the reaction conditions in step (a), it is possible to increase the overall yield of the nitrated lipids as well as reduce the number of different types of nitrated lipids. In one aspect, the step (a) can be performed under anaerobic conditions. In another aspect, step (a) can be performed under anhydrous conditions. In a further aspect, step (a) is performed under anaerobic and anhydrous conditions.

After step (a), the intermediate that is produced is reacted with an oxidant to convert the intermediate to the nitrated lipid (step (b)). Not wishing to be bound by theory, the oxidant oxidizes the selenium compound to produce a selenium-oxo group, which rearranges to produce the nitrated lipid. One aspect of this mechanism is depicted in FIG. 1, whereupon oxidation, the selenium-oxo group rearranges to produce PhSeOH and a nitrated lipid possessing a vinyl nitro group. In one aspect, the oxidant comprises H$_2$O$_2$ or an organic hydroperoxide. The amount of oxidant will vary depending upon the selection of the oxidant and reaction conditions. In one aspect, a 2-fold, 3-fold, 5-fold, 7-fold, 9-fold, 10-fold, 15-fold, or 20-fold molar amount of oxidant is used compared to the molar amount of unsaturated lipid. In one aspect, step (b) is performed in an organic solvent at reduced temperature.

In one aspect, the unsaturated lipid comprises oleic acid, linoleic acid, linolenic acid, arachidonic acid, eicosapentaenoic acid, or docosahexanoic acid, the mercuric salt comprises HgCl$_2$, the selenium compound comprises PhSeBr, the nitrating compound comprises NaNO$_2$, and the oxidant comprises H$_2$O$_2$. In a further aspect, step (a) is performed under anaerobic and anhydrous conditions.

After step (b), one nitrated lipid or mixture of two or more nitrated lipid positional or stereoisomers may be present depending upon reagents and starting materials that are selected. In one aspect, if two or more nitrated lipids are present, each of the nitrated lipids can be separated to produce substantially pure nitrated lipid. In one aspect, the mixture of two or more nitrated lipids can be separated by chromatography. For example liquid chromatography, thin layer chromatography or column chromatography using silicic acid, silical gel or other adsorbents useful for lipid separations, can be used to separate the nitrated lipids. The solvent system used in this aspect will vary depending upon the type and number of nitrated lipids to be separated and can be determined by one of ordinary skill in the art.

Also described herein are methods for stabilizing nitrated lipids, comprising placing the nitrated lipid in a hydrophobic medium. The nitrated lipids are generally stable oils and can be stored indefinitely in organic solvents under anaerobic and anhydrous conditions and reduced temperature. Alternatively, the salts of the nitrated lipids are stable and can be further processed into a formulation. Alternatively, the more stable nitrohydroxy derivative can be formed under alkaline conditions, which at more neutral pH reversibly yields the parent nitrated fatty acid. Alternatively, the nitrated lipids can be placed in detergent emulsions or liposomes, which can be later administered to a subject.

III. Nitro/Hydroxy Lipids and Synthesis Thereof

In one aspect, described herein are lipids comprising at least one nitro group and at least one hydroxyl group, wherein the compound is substantially pure. In one aspect, the nitro group and the hydroxyl group are on adjacent carbon atoms. In this aspect, the lipid contains the fragment HO—C—C—NO$_2$. In another aspect, the nitro/hydroxy lipid has the formula X or XI

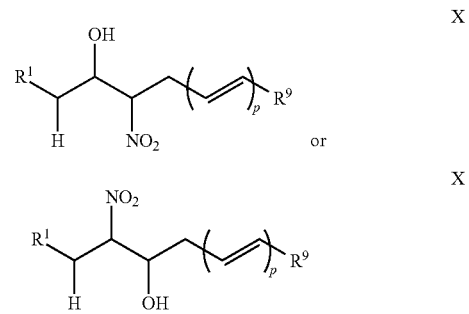

wherein R$^1$ comprises a C$_1$-C$_{24}$ alkyl group, a C$_1$-C$_{24}$ alkenyl group, or C$_1$-C$_{24}$ alkynyl group, and R$^9$ comprises a terminal COOR$^6$ group, wherein R$^6$ comprises hydrogen, C$_1$-C$_{24}$ alkyl, or a pharmaceutically acceptable counterion, and p is from 1 to 12. In a further aspect, the nitro/hydroxy lipid has the formula XII or XIII

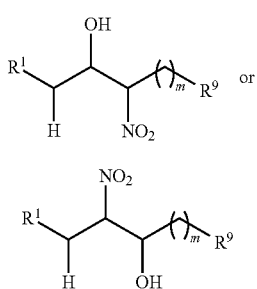

wherein $R^1$ comprises a $C_1$-$C_{24}$ alkyl group, a $C_1$-$C_{24}$ alkenyl group, or $C_1$-$C_{24}$ alkynyl group, and $R^9$ comprises a terminal $COOR^6$ group, wherein $R^6$ comprises hydrogen, $C_1$-$C_{24}$ alkyl, or a pharmaceutically acceptable counterion, and m is from 0 to 12.

Any of the nitrated lipids can be converted to the corresponding nitro/hydroxyl compound. In one aspect, the nitrated lipid is placed in an aqueous base. Not wishing to be bound by theory, it is believed that the nitrated lipid undergoes a Michael addition reaction with water followed by deprotonation to produce the nitro/hydroxyl lipid. This mechanism is depicted below.

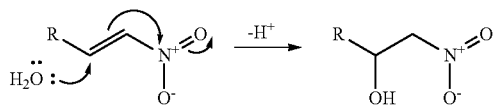

The nitro/hydroxyl lipid can be subsequently isolated by solvent extraction followed by purification using techniques known in the art (e.g., HPLC or thin layer chromatography).

IV. Methods of Use

Delivery

As used throughout, administration of any of the nitrated lipids described herein can occur in conjunction with other therapeutic agents. Thus, the nitrated lipids can be administered alone or in combination with one or more therapeutic agents. For example, a subject can be treated with a nitrated lipid alone, or in combination with chemotherapeutic agents, antibodies, antivirals, steroidal and non-steroidal anti-inflammatories, conventional immunotherapeutic agents, cytokines, chemokines, and/or growth factors. Combinations may be administered either concomitantly (e.g., as an admixture), separately but simultaneously (e.g., via separate intravenous lines into the same subject), or sequentially (e.g., one of the compounds or agents is given first followed by the second). Thus, the term "combination" or "combined" is used to refer to either concomitant, simultaneous, or sequential administration of two or more agents. Furthermore, two or more nitrated lipids described herein can be administered to a subject concomitantly, simultaneously, or sequentially.

The nitrated lipids can be administered in a number of ways depending on whether local or systemic treatment is desired, and on the area to be treated. Administration may be topically (including opthamalically, vaginally, rectally, intranasally), orally, by inhalation, or parenterally, for example by intravenous drip, subcutaneous, intraperitoneal or intramuscular injection. The disclosed compounds can be administered intravenously, intraperitoneally, intramuscularly, subcutaneously, intracavity, transdermally, intratracheally, extracorporeally, or topically (e.g., topical intranasal administration or administration by inhalant). As used herein, "topical intranasal administration" means delivery of the compositions into the nose and nasal passages through one or both of the nares and can comprise delivery by a spraying mechanism or droplet mechanism, or through aerosolization of the nucleic acid or vector. The latter can be effective when a large number of subjects are to be treated simultaneously. Administration of the compositions by inhalant can be through the nose or mouth via delivery by a spraying or droplet mechanism. Delivery can also be directly to any area of the respiratory system (e.g., lungs) via intubation.

Parenteral administration of the composition, if used, is generally characterized by injection. Injectables can be prepared in conventional forms, either as liquid solutions or suspensions, solid forms suitable for solution of suspension in liquid prior to injection, or as emulsions. A more recently revised approach for parenteral administration involves use of a slow release or sustained release system such that a constant dosage is maintained. See, e.g., U.S. Pat. No. 3,610,795, which is incorporated by reference herein in its entirety for the methods taught.

The compositions may be in solution or in suspension (for example, incorporated into microparticles, liposomes, or cells). These compositions may be targeted to a particular cell type via antibodies, receptors, or receptor ligands. The following references are examples of the use of this technology to target specific proteins to given tissue (Senter, et al., Bioconjugate Chem., 2:447-451, (1991); Bagshawe, K. D., Br. J. Cancer, 60:275-281, (1989); Bagshawe, et al., Br. J. Cancer, 58:700-703, (1988); Senter, et al., Bioconjugate Chem., 4:3-9, (1993); Battelli, et al., Cancer Immunol. Immunother., 35:421-425, (1992); Pietersz and McKenzie, Immunolog. Reviews, 129:57-80, (1992); and Roffler, et al., Biochem. Pharmacol, 42:2062-2065, (1991)). Vehicles such as "stealth" and other antibody conjugated liposomes (including lipid mediated drug targeting to colonic carcinoma), receptor mediated targeting of DNA through cell specific ligands, lymphocyte directed tumor targeting, and highly specific therapeutic retroviral targeting of murine glioma cells in vivo. In general, receptors are involved in pathways of endocytosis, either constitutive or ligand induced. These receptors cluster in clathrin-coated pits, enter the cell via clathrin-coated vesicles, pass through an acidified endosome in which the receptors are sorted, and then either recycle to the cell surface, become stored intracellularly, or are degraded in lysosomes. The internalization pathways serve a variety of functions, such as nutrient uptake, removal of activated proteins, clearance of macromolecules, opportunistic entry of viruses and toxins, dissociation and degradation of ligand, and receptor-level regulation. Many receptors follow more than one intracellular pathway, depending on the cell type, receptor concentration, type of ligand, ligand valency, and ligand concentration. Molecular and cellular mechanisms of receptor-mediated endocytosis has been reviewed (Brown and Greene, DNA and Cell Biology 10:6, 399-409 (1991)).

The exact amount of the compositions required will vary from subject to subject, depending on the species, age, weight and general condition of the subject, the severity of the disorder being treated, the particular nucleic acid to be targeted, its mode of administration and the like. Thus, it is not possible to specify an exact amount for every composition. However, an appropriate amount can be determined by one of ordinary skill in the art using only routine experimentation given the teachings herein. In one aspect, the amount of nitrated lipid that is administered can be from 1 nM to 1 mM, 10 nM to 1 mM, 20 nM to 1 mM, 50 nM to 1 mM, 100 nM to 1 mM, 200 nM to 1 mM, 300 nM to 1 mM, or 500 nM to 1 mM. The time at which the nitrated lipids can be administered will also vary depending upon the subject, the disorder, mode of administration, etc. The nitrated lipid can be administered to the subject prior to the onset of inflammation or during a time when the subject is experiencing inflammation. In one aspect, the nitrated lipid can be administered within 24 hours, 20 hours, 16 hours, 12 hours, 8 hours, 4 hours, 2 hours, 1 hour, or 30 minutes before inflammation occurs or 10 hours, 20 hours, 30 hours, 40 hours, 60 hours, 80 hours, 100 hours, or 120 hours after the onset of the inflammation.

Pharmaceutically Acceptable Carriers

The nitrated lipids can be used therapeutically in combination with a pharmaceutically acceptable carrier. Pharmaceutical carriers are known to those skilled in the art. These most typically would be standard carriers for administration of drugs to humans, including solutions such as sterile water, saline, and buffered solutions at physiological pH. The compositions can be administered intramuscularly or subcutaneously. Other compounds will be administered according to standard procedures used by those skilled in the art.

Pharmaceutical compositions may include carriers, thickeners, diluents, solvents, buffers, preservatives, surface active agents and the like in addition to the molecule of choice. Pharmaceutical compositions may also include one or more active ingredients such as antimicrobial agents, anti-inflammatory agents, anesthetics, and the like.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

Formulations for topical administration may include ointments, lotions, creams, gels, drops, suppositories, sprays, liquids and powders. Conventional pharmaceutical carriers, aqueous, powder or oily bases, thickeners and the like may be necessary or desirable.

Compositions for oral administration include powders or granules, suspensions or solutions in water or non-aqueous media, capsules, sachets, or tablets. Thickeners, flavorings, diluents, emulsifiers, dispersing aids or binders may be desirable.

Some of the nitrated lipids may potentially be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines. In another aspect, the nitrated lipid is in the form of the sodium or potassium salt.

In another embodiment, the nitrated lipids can be converted to the corresponding pharmaceutically-acceptable ester such as, for example, the methyl ester.

Therapeutic Uses

The methods described herein contemplate the use of single or mixtures of two or more nitrated or nitro/hydroxyl lipids. In one aspect, disclosed are methods for reducing or preventing inflammation in a subject with inflammation or at risk for inflammation, comprising administering an effective amount of any of the nitrated lipids described herein, wherein the nitrated lipid reduces or prevents the inflammation in the subject. Examples of inflammation include, but are not limited to, pulmonary inflammation, vascular inflammation, renal inflammation, inflammation of the central nervous system, hepatic inflammation, or splanchnic inflammation. The inflammation can be associated with an inflammatory disease including, but not limited to, systemic lupus erythematosus, Hashimoto's disease, rheumatoid arthritis, graft-versus-host disease, Sjögren's syndrome, pernicious anemia, Addison disease, scleroderma, Goodpasture's syndrome, Crohn's disease, autoimmune hemolytic anemia, myasthenia gravis, multiple sclerosis, Alzheimer's disease, amyotrophic lateral sclerosis, Basedow's disease, thrombopenia purpura, insulin-dependent diabetes mellitus, allergy; asthma, inflammatory bowel disease, cancer, ulcerative colitis, scleroderma, cardiomyopathy, atherosclerosis, hypertension, sickle cell disease, or respiratory distress syndrome of neonate and adults. In another aspect, the inflammation can be caused by an organ transplantation, respiratory distress, ventilator induced lung injury, ischemia reperfusion, hemorrhagic shock, or sepsis. In one aspect, when the pulmonary inflammation is caused by respiratory distress or sepsis, the nitrated lipids can reduce or prevent the accumulation of alveolar fluid in a subject.

In one aspect, the nitrated lipids described herein can modulate the expression or activity of one or more nucleic acids that encode one or more inflammatory-related or cell signaling polypeptides. The term "modulate" is defined herein as the ability of the nitrated lipid to decrease or increase the expression or activity relative to a control. The "control" can be either the amount of expression or activity in the absence of a nitrated lipid, or in the presence of solvent or non-nitrated parent lipid used for the synthesis of the nitrated lipid derivative. Alternatively, the "control" can be the amount of expression or activity before or after the period use (i.e., administration of the nitrated lipid). The term "inflammatory-related polyepetide" is defined herein as any polypeptide that can induce or potentiate an inflammatory response. Examples of genes that can be modulated by the nitrated lipids described herein and inflammatory-related polypeptides include, but are not limited to, prostaglandin H synthase-2, gamma glutamyl cysteine synthase, low density lipoprotein receptor, vascular endothelial growth factor, tocopherol binding protein, a heat shock protein (e.g., 10, 40, 60, 70, 90 kD ), prostaglandin receptor EP4, a protein tyrosine phosphatase, a Ca, Na, or K ATPase, a G-protein signaling regulator (e.g., 24 kD), a vasoactive intestinal peptide, a guanine nucleotide exchange factor, a bone morphogenetic protein, an aromatic-inducible cytochrome P450s, an ADP-ribosyltransferase, endothelin-1, a vascular cell adhesion molecule-1, an intercellular adhesion molecule-1, a tumor necrosis factor alpha receptor, an interleukin 1 beta receptor, a transforming growth factor beta receptor, an advanced glycation endproduct-specific receptor, a cAMP phosphodiesterase, a cGMP phosphodiesterase, a cyclin-dependent kinase, cathepsins B and D, a connective tissue growth factor, actin, myosin, a tubulin gene, a c-src tyrosine kinase, an insulin growth factor binding protein, a cysteine-rich angiogenic inducer 61, thrombospondin-1, a cadherin-associated protein beta, heme oxygenase-1, one or more of the genes listed in Table 5, one more of the genes listed in Table 6, one or more of the genes listed in Table 7, or a combination thereof. In one aspect, the nitrated lipid can modulate the nucleic acid 1.5 fold, 2 fold, 3-fold, 5-fold, 10-fold, 20-fold, 30-fold, 40-fold, 50-fold, 75-fold, 100-fold, 125-fold, 150-fold, or greater.

The nitrated lipids described herein can be used to mediate receptors in a cell in order to reduce or prevent inflammation in a subject. In one aspect, described herein are methods for inducing or potentiating peroxisome proliferator activated receptor (PPAR) activity, comprising contacting a cell comprising at least one PPAR receptor with one or more nitrated lipids under conditions that allow the compound to induce or potentiate the activity of the PPAR receptor. The PPAR receptor can be α, δ, or γ. Alternatively, other lipid receptors that nitrated lipids can bind to, be transported by, and mediate include the family of fatty acid binding proteins, G protein-coupled receptors and cis-retinoic acid binding protein. Not wishing to be bound by theory, it is believed that activation of cell receptors such as, for example, PPAR, can modulate the tissue expression and activity of inflammatory-related genes. A number of cell-types can be contacted with the nitrated lipids described herein in order to reduce or prevent inflammation in a subject. Examples of such cells include, but are not limited to the constituent cells of lung, airways, nasal passages, eyes, auditory system, liver, spleen, kidney, intestine, colon, genito-urinary tract, heart, brain, spinal cord, muscle, bone, connective tissue, blood and reticuloendothelial system and nervous tissue.

In another aspect, the nitrated lipids described herein can induce the expression or potentiate the activity of an inflammatory-related polypeptide when a cell comprising at least one nucleic acid that encodes the inflammatory-related polypeptide is contacted with a nitrated lipid under conditions that allow the compound to induce the expression or potentiate the activity of the inflammatory-related polypeptide. In one aspect, the following expressions or activities can be induced or potentiated with the nitrated lipids described herein:
1. Modification of downstream signaling regulated by small G-proteins.
2. Increased phosphorylation and activation of c-Jun N-terminal kinase.
3. Increased the phosphorylation and activation of the transcription factor c-Jun.
4. Modification of activator protein-1 binding and activator protein-1 mediated gene expression
5. Increased phosphorylation and activation of extracellular-signal regulated kinase.
6. Increased phosphorylation and activation of the transcription factor Elk-1.
7. Modification of binding to serum response element (SRE) and SRE mediated gene expression.
8. Increased synthesis of the transcription factor c-Fos.
9. Affect the nuclear translocation of the transcription factor Nrf-2 (Nuclear factor erythroid 2 related factor 2).
10. Modification of the electrophilic response element (also known as antioxidant response element) binding and the electrophilic response element mediated gene expression.
11. Modification of p38 mitogen activated protein kinase activation.
12. Modification of the nuclear translocation of the transcription factor p65.
13. Modification of nuclear factor-kappa B binding and nuclear factor kappa B mediated gene expression.

In other aspects, any of the nitrated lipids described herein can reduce a cell's response to an inflammatory stimulus. In one aspect, the cell can be a neutrophil, monocyte, or macrophage. For example, the nitrated lipids can inhibit neutrophil, monocyte, or macrophage degranulation (e.g., azurophilic) or release of hydrolases and proteases following degranulation, neutrophil, monocyte, or macrophage $O_2^{\bullet-}$ formation, expression of CD11b expression in a neutrophil, monocyte, or macrophage, and fMLP-induced $Ca^{+2}$ influx in a neutrophil, monocyte, or macrophage upon contact of the neutrophil, monocyte, or macrophage with the nitrated lipid. In these aspects, the neutrophil, monocyte, or macrophage can be contacted with the nitrated lipid in vivo, in vitro, or ex vivo.

In one aspect, described herein are methods for regulating the activity of a protein kinase signaling pathway, comprising reacting a kinase with a nitro lipid described herein. In another aspect, the nitrated lipids described herein can regulate the activity of a thiol-dependent enzyme in a cell by contacting the cell with a nitrated lipid of the present invention. The cell can be contacted with the nitrated lipid, in vivo, in vitro, or ex vivo. For example, nitroalkenes inhibit enzymes that depend on thiols as catalytic residues. Not wishing to be bound by theory, it is believed that the thiol can react with the nitrated lipid via a Michael addition reaction. Via this property, nitroalkenes also serve a potent stimuli of thiol modification-dependent protein kinases and their downstream cell signaling pathways. In this regard, a variety of cell protein kinases are activated by nitroalkenes and the associated thiol-dependent phosphoprotein phosphatases can also be inhibited by thiol alkylation. In one aspect, any thiol-dependent structural, cell signaling and catalytic protein can be regulated by the nitrated fatty acid compounds described herein.

In another aspect, the nitrated lipids described herein can control protein trafficking in cells by serving as a thiol-attached hydrophobic membrane trafficking agent for proteins to which they attach. Thus, the alkylation of proteins by membrane-avid nitrated fatty acids will facilitate the localization of proteins containing hydrophobic nitrated fatty acid-amino acid adducts to cytosol, plasma membrane and organelle (nucleus, endoplasmaic reticulum, mitochondrial, golgi, secretory vesicles) membranes.

In another aspect, the nitrated lipids described herein can inhibit platelet function in a subject upon administration of the nitrated lipid to the subject. In one aspect, the nitrated lipids can inhibit thrombin- or other stimuli-induced platelet aggregation by attenuating cAMP-dependent $Ca^{+2}$ mobilization and activation of the phosphorylation of vasodilator-stimulated phosphoprotein (VASP).

In another aspect, the nitrated lipids described herein can be used to induce or potentiate tissue repair in a subject suffering from inflammation. Not wishing to be bound by theory, it is believed that the nitrated lipids can down regulate events that result in inflammation or the impairment of vascular function and blood flow.

In another aspect, the nitrated lipids described herein can promote satiety in a subject upon administration of the nitrated lipid to the subject.

In another aspect, the nitrated lipids described herein can treat cancer upon administering an effective amount of the nitrated lipid to the subject. Not wishing to be bound by theory, it is believed that the nitrated lipids directly stimulate tumor cell killing and potentiate the killing of tumor cells by standard chemotherapeutic drugs. The cell necrosis and apoptosis-inducing activity is believed to be the result of nitrated lipid/PPAR ligand activity (e.g., PPAR activation), as well as by stimulating other cell signaling pathways noted above that mediate cell growth, cell differentiation and death signaling pathways.

In another aspect, the nitrated lipids set forth herein can act as nitric oxide (NO) donors, as described in the Examples. Therefore, the nitrated lipids described herein can be used to administer NO to a subject and/or treat a NO-related condition in a subject. These conditions include, but are not limited to, atherosclerosis, myocardial infarction, peripheral vascular disease, coronary artery diseases, heart failure, stroke, essential hypertension, diabetes mellitus, pre-eclampsia, erectile dysfunction, impotence, diabetic nephropathy, inflammatory glomerular diseases, acute renal failure, chronic renal failure, inflammation, bacterial infection, septic shock, respiratory distress syndromes, arthritis, cancer, impetigo, epidermolysis bullosa, eczema, neurodermatitis, psoriasis, pruritis, erythema, hidradenitis suppurativa warts, diaper rash and jock itch.

In another aspect, described herein are methods for detecting inflammation in a subject, comprising (a) measuring the amount of a nitrated lipid present in the subject and (b) comparing the amount of nitrated lipid in the subject to the amount of nitrated lipid present in a subject that is not experiencing any inflammation. In one aspect, patients with cardiovascular disease have increased amounts of nitrated fatty acid. Based on the presence of nitrated lipids, the detection of increased levels of nitrated fatty acids in blood, tissues and bodily fluids can serve to diagnose the occurrence, progression and/or resolution of the inflammatory process.

EXAMPLES

The following examples are put forth so as to provide those of ordinary skill in the art with a complete disclosure and description of how the compounds, compositions, and methods described and claimed herein are made and evaluated, and are intended to be purely exemplary and are not intended to limit the scope of what the inventors regard as their invention. Efforts have been made to ensure accuracy with respect to numbers (e.g., amounts, temperature, etc.) but some errors and deviations should be accounted for. Unless indicated otherwise, parts are parts by weight, temperature is in ° C. or is at ambient temperature, and pressure is at or near atmospheric. There are numerous variations and combinations of reaction conditions, e.g., component concentrations, desired solvents, solvent mixtures, temperatures, pressures and other reaction ranges and conditions that can be used to optimize the product purity and yield obtained from the described process. Only reasonable and routine experimentation will be required to optimize such process conditions.

Example 1

Materials. Linoleic acid was purchased from Nu-Check Prep (Elysian, Minn.). Phenylselenium bromide, HgCl$_2$, NaNO$_2$, anhydrous tetrahydrofuran, N,N-diisopropylethylamine (99.5%) and acetonitrile were obtained from Sigma/Aldrich (St Louis, Mo.). Silica gel HF thin layer chromatography (TLC) plates (250 m) were from Analtech (Newark, Del.). Pentafluorobenzyl bromide and methanolic BF$_3$ was from Pierce (Rockford, Ill.). Solvents used in synthesis were HPLC grade or better and were purchased from Fisher Scientific (Fairlawn, N.J.). Solvents used for mass spectrometric analyses from Burdick and Jackson (Muskigon, Mich.). [$^{13}$C]Linoleic acid was from Spectra Stable Isotopes (Columbia, Md.) and [$^{15}$N]NaNO$_2$ was from Cambridge Isotope Laboratories, Inc. (Andover, Mass.). [$^{14}$N]LNO$_2$, [$^{13}$C]LNO$_2$ and [$^{15}$N]LNO$_2$ positional isomers were synthesized as described previously for nitrated fatty acids.

Figure 2:
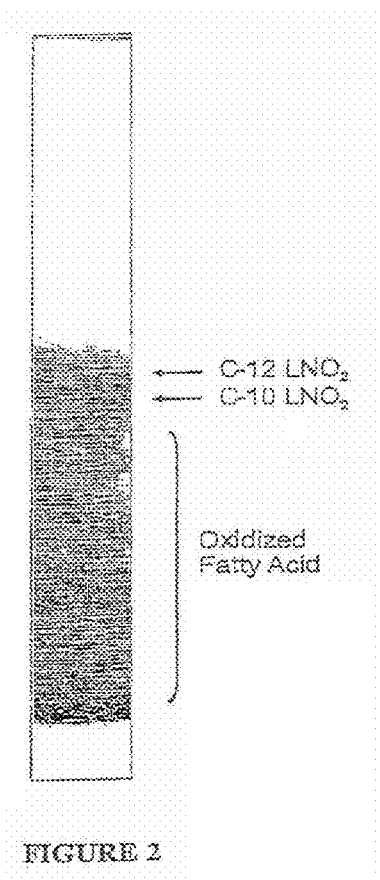
FIG. 2 shows the separation of C-10 and C-12 nitrated linoleic acid from a crude reaction mixture by thin layer chromatography.

LNO$_2$ synthesis. Linoleic acid/HgCl$_2$/phenylselenium bromide/NaNO$_2$ (1:1.3:1:1, mol/mol) were combined in THF/acetonitrile (1:1, v/v) with a final concentration of 0.15 M linoleic acid. Care was taken to use anhydrous solvents, dry glassware and reagents that had been dried in vacuo over phosphorus pentoxide. The reaction mixture was stirred (4 h, 25° C.) followed by centrifugation to sediment the precipitate. The supernatant was recovered, the solvent evaporated in vacuo, the product mixture redissolved in THF (original volume) and the temperature reduced to 0° C. A 10-fold molar excess of H$_2$O$_2$ was slowly added with stirring to the mixture then allowed to rest in an ice bath for 20 min followed by a gradual warming to room temp (45 min). The product mixture was extracted with equal parts saturated NaCl and diethyl ether, the organic phase collected, the solvent removed in vacuo and the lipid products were resolvated in CH$_2$Cl$_2$/CH$_3$OH (4:1, v/v). A mixture of LNO$_2$ positional isomers were initially separated from the product mixture by preparative TLC using silica gel HF plates developed twice in a solvent system consisting of hexane/ether/acetic acid (70:30:1, v/v). Regions of silica containing LNO$_2$ were scraped, extracted (29) and stored in CH$_3$OH under argon at −80° C. Under these conditions, purified nitrated linoleic acid is stable for >3 months. Large scale purification of the individual positional isomers was performed by preparative HPLC using a 250×21.2 mm C18 Phenomenex Luna column (5 μm particle size). Lipids were eluted from the column using a gradient solvent system consisting of A (H$_2$O containing 0.1% NH$_4$OH) and B (CNCH$_3$ containing 0.1% H$_2$O) under the following conditions: 20-80% B (linear increase, 45 min), 80% B (2 min), 20% B (5 min). Fractions were collected as positional isomers eluted, the solvent removed in vacuo and the lipids were stored in CH$_3$OH under argon at −80° C. Stable isotopes of LNO$_2$, specifically [$^{13}$C]LNO$_2$ and [$^{15}$N]LNO$_2$, were synthesized as above, except that [$^{13}$C]linoleic acid or [$^{15}$N]NaNO$_2$ were substituted in the synthetic scheme. FIG. 1 depicts a synthetic scheme for producing nitrated lipids. The process described above significantly increased the purity and yield of fatty acid allylic nitration products, facilitating structural resolution of specific LNO$_2$ positional isomers and future cell signaling studies (22, 32, 33). Preparative TLC permitted the initial resolution of nitrated fatty acids from starting materials and oxidized linoleic acid species (FIG. 2). The principal C-10 and C-12 positional isomers have R$_f$ values of 0.45 and 0.50, respectively. The changes in synthetic approaches, use of anhydrous reagents and the execution of nitrosenylation reaction steps under a nitrogen atmosphere resulted in an increase in yield of nitrated linoleic acid products from 4% to 56%.

In an alternate aspect, nitrated fatty acids can be separated and purified from oils such as, for example, fish oil, soy bean oil, and olive oil. For example, silica gel and silicic acid columns can be used to fractionate the nitro-fatty acids, followed by preparative TLC or HPLC to separate the different nitrated fatty acids. Nitro-oleate is the predominant (>90%) marine and plant-nitroalkene.

Spectral analysis of LNO$_2$. Initial concentrations of synthetic LNO$_2$ preparations were measured by chemiluminescent nitrogen analysis (Antek Instruments, Houston, Tex.)

using caffeine as a standard. This data was utilized to determine dilution concentrations for subsequent spectral analysis. The extinction coefficients (ε) for $LNO_2$ and the isotopic derivatives [$^{13}C$]$LNO_2$ and [$^{15}N$]$LNO_2$ were measured using a UV-VIS spectrophotometer (Shimadzu, Japan) set to measure absorbance at 329 nm, the absorbance maximum specific to $LNO_2$ as compared to linoleic acid. Absorbance values for increasing concentrations of $LNO_2$, [$^{15}N$]$LNO_2$ or [$^{13}C$]$LNO_2$ in MeOH containing 20 mM NaOH were plotted against concentration to calculate slope/extinction coefficient.

Figure 3:
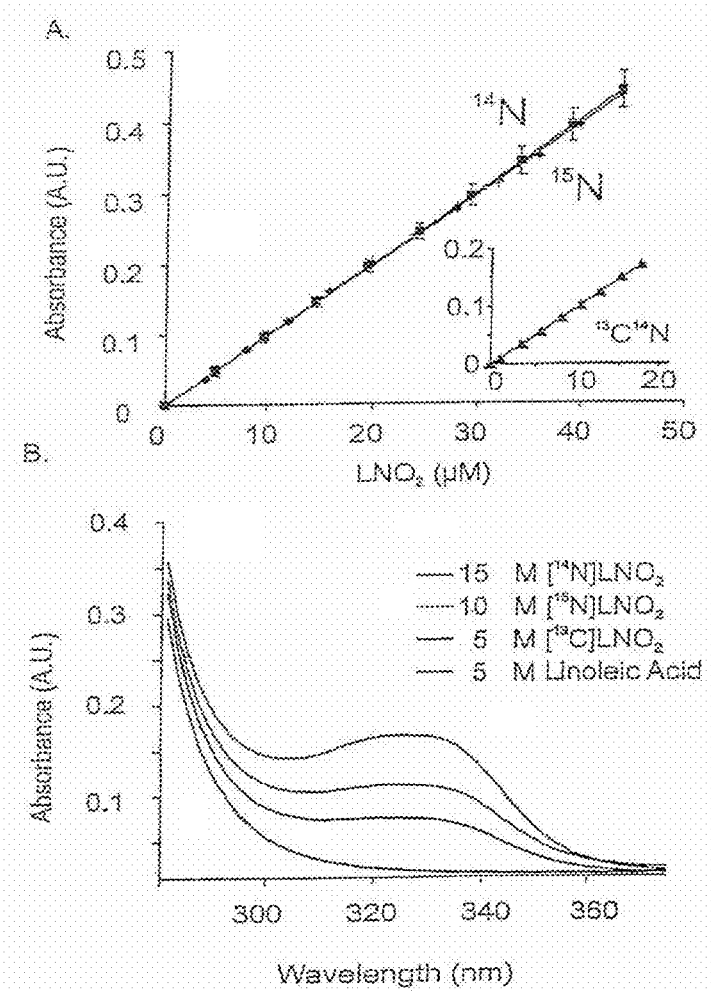
FIG. 3 shows the extinction coefficient (A) and ultraviolet light absorption spectrum (B) of nitrated linoleic acid.

Nitrated linoleic acid displays a characteristic absorption profile and maximum, permitting determination of an extinction coefficient and providing a facile method for measuring concentrations of synthetic $LNO_2$. This species displays a unique absorbance maximum at 329 nm, compared with linoleic acid (FIG. 3A). Plotting absorbance versus concentration profiles for each of the synthetic $LNO_2$ preparations reported herein—[$^{14}N$]$LNO_2$, [$^{15}N$]$LNO_2$ and [$^{13}C$]$LNO_2$—generated identical extinction coefficients for all $LNO_2$ derivatives: $\epsilon=10.1$ $cm^{-1}M^{-1}$ (FIG. 3B).

Red blood cell and plasma lipid isolation and extraction. Peripheral blood from healthy human volunteers was collected by venipuncture in heparinized tubes, centrifuged (1200×g; 10 min) and plasma isolated from red cell pellets from which the buffy coat was removed. Crude lipid extracts were prepared from packed red cells and plasma by the method of Bligh and Dyer (29) and analyzed by mass spectrometry. Care was taken to avoid acidification during all steps of plasma fractionation and lipid extraction to prevent artifactual lipid nitration due to the presence of endogenous $NO_2^-$. Extracts from red cells were analyzed by mass spectrometry; however, lipid extracts from plasma were first fractionated by TLC to separate $LNO_2$ from the bulk of neutral lipids present in plasma, minimizing ionization dampening during $LNO_2$ analysis by mass spectrometry. TLC plates were developed twice in a solvent system consisting of hexane:ether:acetic acid (70:30:1, v/v), and regions of silica containing $LNO_2$, identified by comparing to the migration of synthetic standards, were scraped and extracted (29). To measure the esterified $LNO_2$ content in red cell membranes and plasma lipoproteins, lipid extracts were first hydrolyzed (30), fractionated by TLC and analyzed by mass spectrometry.

In FIG. 6A, [$^{13}C$]$LNO_2$ was added to lipid extractions as an internal standard to quantitate the free and esterified $LNO_2$ content of red cells and plasma obtained from healthy human volunteers. The mean age of the 5 female and 5 male subjects was 34 yr. The endogenous $LNO_2$ isomers co-eluted with the added $^{13}C$-labeled $LNO_2$ internal standard, with the internal standard differentiated from endogenous $LNO_2$ by monitoring its unique m/z 342/295 MRM transition. In FIG. 6B, the internal standard curve for $LNO_2$ reveals linear detector responses over five orders of magnitude. The limit of quantitation (LOQ) for $LNO_2$, as defined by ten times the standard deviation of the noise, is approximately 0.3 fmol (~100 fg) injected on column.

Analysis of synthetic $LNO_2$ methyl and pentafluorobenzyl esters by gas chromatography mass spectrometry. Methyl ester-derivatives of synthetic $LNO_2$ isomers were analyzed by gas chromatography mass spectrometry (GC-MS) in both positive and negative ion modes. Electron-impact (EI) ionization was used to identify and characterize the fragmentation pattern of the two main positional isomers of $LNO_2$ methyl esters. Methyl esters were prepared by drying $LNO_2$ under a stream of nitrogen and redissolving in methanolic $BF_3$ (14% $BF_3$, 86% $CH_3OH$); with the methylation reaction proceeding for 8 min at 60° C. Methyl esters were then extracted with hexane, washed twice with saturated saline, redissolved in undecane and analyzed by electron-impact GC-MS. EI GC-MS was performed using a Saturn 2000 mass spectrometer coupled with a Varian 3800 gas chromatograph. Samples were ionized by electron impact at +70 eV. Methyl ester-derivatized $LNO_2$ isomers were resolved by GC using a CP-7420 capillary column (0.25 mm ID, 100 m fused silica, Varian, Palo Alto, Calif.) with the following temperature gradient: 60° C. (2 min); 60 to 120° C. at 20° C./min, held for 2 min; 120 to 270° C. at 20° C./min, held for 20 min. Helium was used as the carrier gas.

Due to the low sensitivity of positive ion GC-MS to $LNO_2$, negative ion chemical ionization (NICI) was used to characterize pentafluorobenzyl (PFB) esters of synthetic $LNO_2$ and detect $LNO_2$ species in vivo. PFB esters of synthetic $LNO_2$, red cell and plasma lipids were prepared (29), with biological lipids first partially purified by TLC as previously noted. Lipids were then subjected to PFB esterification and analysis by negative ion chemical ionization GC-MS using a Hewlett Packard 5890 GC (Palo Alto, Calif.) coupled to a single quadrupole Hewlett Packard MS using a 30 m CP-Sil 8CB-MS column (5% phenyl, 95% dimethylpolysiloxane; Varian, Palo Alto, Calif.) (31). The following temperature gradient was used to resolve the positional isomers of $LNO_2$: 165 to 190° C. at 10° C./min; 190 to 270° C. at 2° C./min; and 270 to 290° C. at 5° C./min. Helium and methane were used as carrier and reagent gases, respectively. The detection of $LNO_2$ was conducted by total ion count monitoring of [M-PFB]$^-$, i.e., m/z 324 ([$^{12}C^{14}N$]$LNO_2$), 325 ([$^{12}C$, $^{15}N$]) and 342 ([$^{13}C$, $^{14}N$]$LNO_2$).

Initial characterization of positional isomers of synthetic $LNO_2$ was via EI GC-MS on $LNO_2$ methyl esters. Total ion count monitoring of the derivatized parent ion $LNO_2$ revealed 2 dominant peaks at 38.75 and 39 min when resolved using a 100 m column (FIG. 4A). Product ion analysis of each peak (FIG. 4C) generated fragmentation patterns similar to previously reported for acidic nitration of ethyl linoleate (18). The first and second peaks correspond to linoleic acid that is nitrated on the 12- and the 10-carbon, respectively (referred to as C12 and C10 isomers). These two isomers are identified by the unique daughter ions m/z 250 and m/z 282 (specific to C12), and m/z 196 (specific to C10). Analysis of [$^{15}N$]$LNO_2$ revealed fragmentation patterns with these identifying ions shifted by m/z=+1, further affirming fragments containing the nitro group (FIG. 4C). As a control for potential $BF_3$-dependent artifactual products, anhydrous methanolic sulfuric acid (1%) esterification was performed to further verify the formation of the same respective $LNO_2$ methyl ester positional isomers.

Structural analysis of synthetic $LNO_2$ isomers by EI GC MS yielded important isomeric structural information and identification; but lacks sensitivity for the detection, structural characterization and quantification of $LNO_2$ derivatives present in biological samples. Thus, these analyses were performed by NICI GC-MS on $LNO_2$ species that had been derivatized to PFB esters (FIG. 4B). Chromatographic separation of both synthetic $LNO_2$ and TLC-separated red cell lipid extracts showed two dominant peaks, C12 and C10, and two minor peaks ascribed to C13 and C9 positional isomers of $LNO_2$; with approximately 95% of total peak area accounted for by C12 and C10 isomers. To confirm that the identities of the $LNO_2$—PFB derivatives were the same as those identified as $LNO_2$-methyl esters, the $LNO_2$—PFB derivatives were run on EI positive ionization mode and identified by formation of characteristic fragmentation pattern (data not shown). Initial detection and quantitation of endogenous levels of $LNO_2$ was performed using NICI GC-MS. $[^{13}C]LNO_2$ was added during the monophase of lipid extractions as an internal standard to correct for losses due to TLC and derivatization. The requirement for TLC separation to enrich fractions containing $LNO_2$, the additional requirement for derivatization and on-column thermal decomposition creating limitations for analyzing nitrohydroxy- and nitrohydroperoxy fatty acids all combined to yield inconsistent quantitation of $LNO_2$ levels in biological samples upon analysis by GC-MS. Consequently, we developed a LC-MS/MS based method to more reliably characterize and quantitate $LNO_2$ in biological samples.

Analysis of $LNO_2$ positional isomers by electrospray ionization triple quadrupole mass spectrometry. Qualitative analysis of nitrated linoleic acid positional isomers by electrospray ionization mass spectrometry was performed using an Applied Biosystems/MDS Sciex 4000 Q Trap™, a hybrid triple quadrupole-linear ion trap mass spectrometer. To separate and characterize the two major $LNO_2$ positional isomers, synthetic standards and lipid extracts from biological samples were resolved by reverse-phase high performance liquid chromatography (HPLC) using a 150×2 mm C18 Phenomenex Luna column (3 μm particle size). Lipids were eluted using a gradient solvent system consisting of A ($H_2O$ containing 0.1% $NH_4OH$) and B ($CNCH_3$ containing 0.1% $H_2O$) under the following conditions: 20-70% B (linear increase, 20 min), 70-95% B (2 min), 95% B (8 min), 95-20% B (1 min) and 20% B (5 min). Using these gradient conditions, two major and two minor $LNO_2$ positional isomers were separated with baseline resolution. The resolved positional isomers of $LNO_2$ were detected by mass spectrometry using a multiple reaction monitoring (MRM) scan mode by reporting molecules that undergo an m/z 324/277 mass transition. This transition, consistent with the loss of $HNO_2$ ($[M-(HNO_2)-H]^-$), is common for all mononitrated positional isomers of linoleic acid. Concurrent with MRM, enhanced product ion analysis (EPI) was performed to generate characteristic and identifying fragmentation patterns of the eluting species with a precursor mass of m/z 324. In some analyses, specific fragments appearing in the EPI spectra were further fragmented in the ion trap to generate a $MS^3$ spectrum to verify structural elucidation.

The most sensitive and selective technique available for analyte quantitation is triple quadrupole mass spectrometry detecting in the MRM. An HPLC separation strategy that baseline-resolved individual $LNO_2$ positional isomers permitted the MS-based quantitation of $LNO_2$ positional isomers, following chromatography of red cell and plasma lipid extracts. By monitoring the m/z 324/277 mass transition of the linoleate nitro derivative and the fatty acid parent molecule, respectively (FIG. 5A-1). To initially identify individual $LNO_2$ positional isomers resolved by HPLC separation, the two major species were collected (peaks 1 and 2, FIG. 6B), derivatized to PFB-esters and analyzed by GC-MS. From GC-MS analysis, the first species eluting upon HPLC separation was identified as the C12 isomer and the second the C10 nitro derivative. To further characterize synthetic $LNO_2$ isomeric structures, the linear ion trap mode of the hybrid mass spectrometer was used to perform enhanced product ion analysis on eluting peaks to generate a characteristic, identifying fragmentation pattern for each $LNO_2$ positional isomer (FIGS. 5B-1, C-1). The ion trap enabled the concentration and thus detection of otherwise minor fragment ions, with MS/MS analysis revealing the unique fragments m/z 168 and 228 for the C10 isomer, as well as the fragments common to all $LNO_2$ isomers (m/z 233, 244, 277, 293 and 306, FIG. 5C-1). The m/z 228 ion was further fragmented in the ion trap using the $MS^3$ scanning mode, generating a fragment with m/z 46, indicating the loss of a nitro group and assigning the nitro group to the 9-10 double bond. Using $[^{15}N]LNO_2$, the C10 isomer generated a fragment of m/z 229 that undergoes further fragmentation to m/z 47 (not shown). FIG. 5B-1 presents the characteristic fragmentation pattern obtained from MS/MS of the C12 isomer. The unique fragments to $C12-LNO_2$, m/z 196 and 157, and the common fragments (m/z 233, 244, 277, 293 and 306) are present and consistent with a nitro group located at the 12-carbon of linoleic acid. In aggregate, from the synthetic rationale and GC MS and HPLC-ESI MS/MS data, the C10 and the C12 isomers are identified as 10-nitro-9-cis,12-cis-octadecadienoic acid and 12-nitro-9-cis,12-cis-octadecadienoic acid, respectively.

Figure 5:
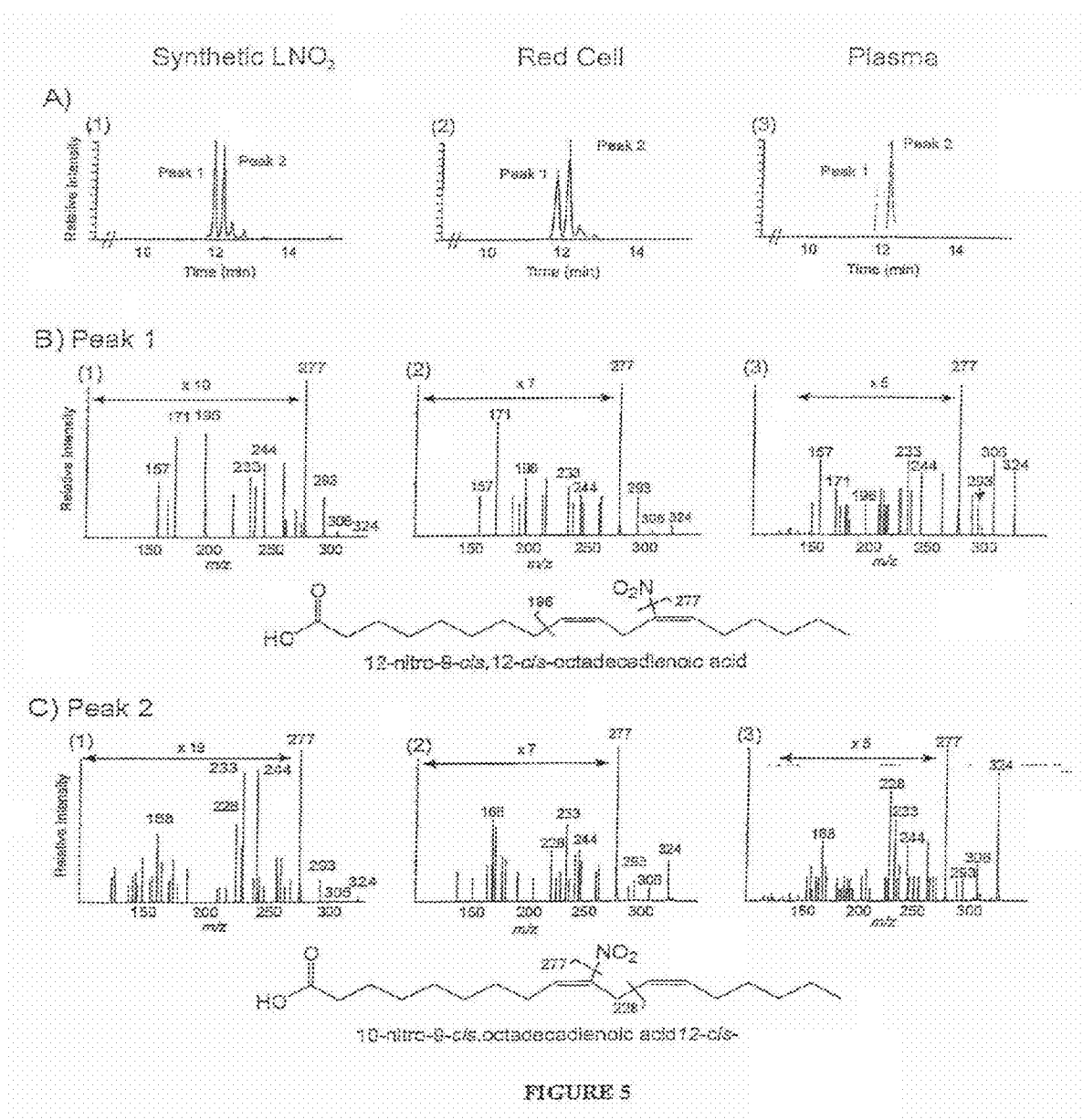
FIG. 5 shows the HPLC resolution of individual positional isomers of nitro derivatives of linoleic acid present in a) synthetic preparations, b) red cells and c) plasma; and in concert with this exemplification of positional isomer resolution is the structural characterization of individual nitrated linoleic acid positional isomers by electrospray ionization triple quadrupole mass spectrometry.

HPLC-ESI MS/MS was used to characterize and quantitate $LNO_2$ species present in healthy human blood, specifically red cells and plasma (FIG. 5). The MRM elution profiles for red cell and plasma lipid extracts were identical to those obtained from the synthetic standards (FIGS. 5B-2, C-2 and 5B-3, C-3). All characteristic fragments found in the EPI spectra of the synthetic C10 and C12 $LNO_2$ isomers were present in the resolved biological extracts, further affirming that red cells and plasma contain $LNO_2$ positional isomers identical to synthetic standards.

Control studies relevant to processing and analysis-induced lipid nitration. In the presence of nitrite and acidic conditions, unsaturated fatty acids undergo nitration to products that reflect the chromatographic and MS characteristics of nitrosenylation-derived synthetic $LNO_2$ isomers (18-20). Thus, acidic conditions were either avoided or documented for potential influence on product yield and nature. Importantly, lipid extractions were routinely conducted in the presence of pH 7.4 aqueous buffers. Comparison of $LNO_2$ content in preparations extracted under neutral or acidic conditions revealed that there was no difference in $LNO_2$ yield or $LNO_2$ isomer distribution only in the complete absence of $NO_2^-$. Acidic lipid extraction conditions (pH<4.0) in the presence of exogenously-added biological concentrations of $NO_2^-$ (10-500 μM) induced additional linoleate nitration, as indicated by nitration of $^{13}C$-linoleic acid added to pure linoleate or biological lipid extracts. When lipid extracts are separated by TLC prior to MS analysis, effective resolution of $LNO_2$ from native and oxidized fatty acids requires the use of a 1% acetic acid-containing solvent system. It was observed that when $NO_2^-$ was present in the TLC chromatographic solvent at concentrations not expected from biological analyses (>1 mM), $LNO_2$ was formed de novo by acid-catalyzed nitration reactions. Since the initial solvent extraction of lipids from synthetic mixtures or biological materials resulted in removal of >95% of all adventitious $NO_2^-$, confidence exists that artifactual fatty acid nitration reactions were not occurring during acidic HPLC or TLC resolution. With regard to biological sample analysis, this latter precept was affirmed by a) adding $^{13}C$-labeled linoleic acid prior to red cell and plasma lipid extraction, purification and MS analysis and b) observing no formation of $^{13}C$-labeled nitrated linoleic acid derivatives.

Detection and quantitation of $LNO_2$ in human red blood cells. Quantitation of $LNO_2$ in biological samples was performed as above, with modification. During the monophase stage of lipid extractions (29), a known quantity of $[^{13}C]LNO_2$ was added as internal standard to correct for loss during extraction and TLC. The gradient elution profile was changed so that all $LNO_2$ positional isomers co-eluted. Lipids were eluted from the same column used for structural characterization using a gradient solvent system consisting of A ($H_2O$ containing 0.1% $NH_4OH$) and B ($CNCH_3$ containing 0.1% $H_2O$) under the following conditions: 80-90% B (2 min), 90% B (3 min), 90-80% B (1 min) and 80% B (2 min). Two MRM transitions were monitored: m/z 324/277, for LNO$_2$ isomers, and m/z 342/295, a transition consistent with the loss of HNO$_2$ for the $^{13}$C-labeled internal standard. The areas under each peak were integrated, the ratio of analyte to internal standard areas was determined and amounts of LNO$_2$ were quantitated using Analyst 1.4 quantitation software (Applied Biosystems, Foster City, Calif.) by fitting the data to an internal standard curve. Adjustable mass spectrometer settings for both qualitative and quantitative analyses were as follows: CUR 10; IS −4500; TEM 450; GS1 50; GS2 60; CAD 2 (8 when EPI experiments were concurrently performed); DP −50; and EP −10. House-generated zero grade air was used as the source gas and nitrogen was used as the curtain and collision gases.

Figure 6:
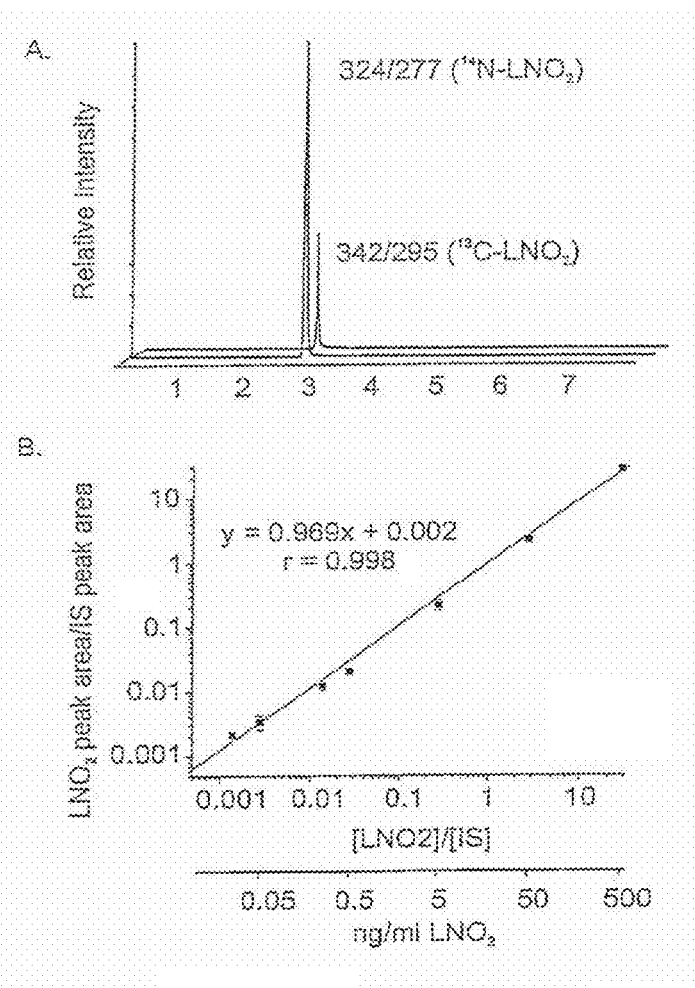
FIG. 6 shows the standard curve used for quantitative analysis of red blood cell and plasma nitrated linoleic acid content.

To quantitate net LNO$_2$ species present in red cells and plasma, HPLC gradient conditions were changed (see Experimental Methods) so that all positional isomers co-eluted (FIG. 6). MRM transitions for the combined LNO$_2$ and [$^{13}$C]LNO$_2$ (m/z 324 and 342, respectively) were monitored, with analytes eluting at 2 min. Nitrated linoleic acid concentration was a function of the ratio of analyte to internal standard peak areas using an internal standard curve that is linear over five orders of magnitude. Blood samples obtained from ten healthy human volunteers (5 female, 5 male, ages ranging from 22 to 45) revealed free LNO$_2$ in red cells (i.e., LNO$_2$ not esterified to glycerophospholipids or neutral lipids) to be 49.6±16.6 pmol/ml packed cells. Total free and esterified LNO$_2$, the amount present in saponified samples, was 249±104 pmol/ml packed cells. Thus, approximately 75% of LNO$_2$ in red cells exists as esterified fatty acids. In plasma, free and total (free plus esterified) LNO$_2$ was 78.9±34.5 pmol/ml plasma 629±242 nM, respectively, with free LNO$_2$ representing 85% of total (Table 1). These values indicate that LNO$_2$ species are quantitatively the greatest pool of bioactive oxides of nitrogen in the vascular compartment (34-37).

Throughout the Background and Example 1, several publications have been referenced. These publications are listed in the Reference List following Example 1. The disclosures of these publications in their entireties are hereby incorporated by reference into this application in order to more fully describe the compounds, compositions and methods described herein.

TABLE 1

Biologically active nitrogen oxide derivatives in human blood - comparison with net C10- and C12-nitro derivatives of linoleic acid. Venous blood was obtained from healthy human volunteers, centrifuged (1200 x g; 10 min) and plasma isolated from red cell pellets from which the buffy coat was removed. Total lipid extracts were prepared from packed red cells and plasma (29) and analyzed by mass spectrometry as described in Experimental Methods. Total LNO$_2$ (free plus esterified) was determined in lipid extracts following saponification. Free and total LNO$_2$ was quantitated by fitting analyte to internal standard area ratios obtained by mass spectrometry to an internal standard curve. Data are expressed as mean ± SD (n = 10; 5 female, 5 male).

| Species | Compartment | Concentration (nM) | Reference |
|---|---|---|---|
| NO$_2$$^-$ | Plasma | 205 ± 21 | (35, 36) |
| RSNO | Plasma | 7.2 ± 1.1 | (35, 36) |
| LNO$_2$ | Plasma Free | 80 ± 34 | |
| | Esterified | 550 ± 274 | |
| | Total | 630 ± 240 | |
| Hb-NO | Blood | >50 | (37) |
| Hb-SNO | Blood | 0-150 | (34) |

TABLE 1-continued

Biologically active nitrogen oxide derivatives in human blood - comparison with net C10- and C12-nitro derivatives of linoleic acid. Venous blood was obtained from healthy human volunteers, centrifuged (1200 x g; 10 min) and plasma isolated from red cell pellets from which the buffy coat was removed. Total lipid extracts were prepared from packed red cells and plasma (29) and analyzed by mass spectrometry as described in Experimental Methods. Total LNO$_2$ (free plus esterified) was determined in lipid extracts following saponification. Free and total LNO$_2$ was quantitated by fitting analyte to internal standard area ratios obtained by mass spectrometry to an internal standard curve. Data are expressed as mean ± SD (n = 10; 5 female, 5 male).

| Species | Compartment | Concentration (nM) | Reference |
|---|---|---|---|
| LNO$_2$ | Packed red cells Free | 25 ± 8 | |
| | Esterified | 199 ± 60 | |
| | Total | 224 ± 52 | |
| LNO$_2$ | Whole Blood* | 477 ± 128 | |

*assuming a 40% hematocrit

REFERENCES

1. Arnold, W. P., Mittal, C. K., Katsuki, S. & Murad, F. (1977) *Proc. Natl. Acad. Sci. U.S.A* 74, 3203-3207.
2. Beckman, J. S., Beckman, T. W., Chen, J., Marshall, P. A. & Freeman, B. A. (1990) *Proc. Natl. Acad. Sci. U.S.A* 87, 1620-1624.
3. Nathan, C. (1992) *Federation of American Societies for Experimental Biology Journal* 6, 3051-3064.
4. Jourd'heuil, D., Miranda, K. M., Kim, S. M., Espey, M. G., Vodovotz, Y., Laroux, S., Mai, C. T., Miles, A. M., Grisham, M. B. & Wink, D. A. (1999) *Arch. Biochem. Biophys.* 365, 92-100.
5. Rubbo, H., Darley-Usmar, V. & Freeman, B. A. (1996) *Chem. Res. Toxicol.* 9, 809-820.
6. Kissner, R., Nauser, T., Bugnon, P., Lye, P. G. & Koppenol, W. H. (1997) *Chem. Res. Toxicol.* 10, 1285-1292.
7. Radi, R., Denicola, A. & Freeman, B. A. (1999) *Methods Enzymol.* 301, 353-367.
8. Baldus, S., Eiserich, J. P., Mani, A., Castro, L., Figueroa, M., Chumley, P., Ma, W., Tousson, A., White, C. R., Bullard, D. C. et al. (2001) *J Clin. Invest* 108, 1759-1770.
9. Castro, L., Eiserich, J. P., Sweeney, S., Radi, R. & Freeman, B. A. (2004) *Arch. Biochem. Biophys.* 421, 99-107.
10. Eiserich, J. P., Baldus, S., Brennan, M. L., Ma, W., Zhang, C., Tousson, A., Castro, L., Lusis, A. J., Nauseef, W. M., White, C. R. et al. (2002) *Science* 296, 2391-2394.
11. Grisham, M. B. (1985) *J Free Radic. Biol. Med.* 1, 227-232.
12. Liu, X., Miller, M. J., Joshi, M. S., Thomas, D. D. & Lancaster, J. R., Jr. (1998) *Proc. Natl. Acad. Sci. U. S. A* 95, 2175-2179.
13. Subczynski, W. K., Lomnicka, M. & Hyde, J. S. (1996) *Free Radic. Res.* 24, 343-349.
14. Thomas, D. D., Liu, X., Kantrow, S. P. & Lancaster, J. R., Jr. (2001) *Proc. Natl. Acad Sci. U. S. A* 98, 355-360.
15. Baldus, S., Castro, L., Eiserich, J. P. & Freeman, B. A. (2001) *Am. J. Respir. Crit Care Med.* 163, 308-310.
16. Gallon, A. A. & Pryor, W. A. (1993) *Lipids* 28, 125-133.
17. Gallon, A. A. & Pryor, W. A. (1994) *Lipids* 29, 171-176.
18. Napolitano, A., Camera, E., Picardo, M. & d'Ischia, M. (2000) *J. Org. Chem.* 65, 4853-4860.
19. Napolitano, A., Crescenzi, O., Camera, E., Giudicianni, I., Picardo, M. & d'Ischia, M. (2004) *Tetrahedron* 58, 5061-5067.

20. O'Donnell, V. B., Eiserich, J. P., Chumley, P. H., Jablonsky, M. J., Krishna, N. R., Kirk, M., Barnes, S., Darley-Usmar, V. M. & Freeman, B. A. (1999) *Chem. Res. Toxicol.* 12, 83-92.
21. Pryor, W. A., Lightsey, J. W. & Church, D. F. (2004) *Journal of the american chemical society* 104, 6685-6692.
22. Lim, D. G., Sweeney, S., Bloodsworth, A., White, C. R., Chumley, P. H., Krishna, N. R., Schopfer, F., O'Donnell, V. B., Eiserich, J. P. & Freeman, B. A. (2002) *Proc. Natl. Acad. Sci. U. S. A* 99, 15941-15946.
23. Coles, B., Bloodsworth, A., Clark, S. R., Lewis, M. J., Cross, A. R., Freeman, B. A. & O'Donnell, V. B. (2002) *Circ. Res.* 91, 375-381.
24. O'Donnell, V. B. & Freeman, B. A. (2001) *Circ. Res.* 88, 12-21.
25. O'Donnell, V. B., Chumley, P. H., Hogg, N., Bloodsworth, A., Darley-Usmar, V. M. & Freeman, B. A. (1997) *Biochemistry* 36, 15216-15223.
26. Coles, B., Bloodsworth, A., Eiserich, J. P., Coffey, M. J., McLoughlin, R. M., Giddings, J. C., Lewis, M. J., Haslam, R. J., Freeman, B. A. & O'Donnell, V. B. (2002) *J. Biol. Chem.* 277, 5832-5840.
27. Coles, B., Bloodsworth, A., Clark, S. R., Lewis, M. J., Cross, A. R., Freeman, B. A. & O'Donnell, V. B. (2002) *Circ. Res.* 91, 375-381.
28. Balazy, M., Iesaki, T., Park, J. L., Jiang, H., Kaminski, P. M. & Wolin, M. S. (2001) *J. Pharmacol. Exp. Ther.* 299, 611-619.
29. Bligh, E. G. & Dyer, W. L. (1959) *Can. J. Biochem. Physiol.* 37, 911-917.
30. Nakamura, T., Bratton, D. L. & Murphy, R. C. (1997) *J. Mass Spectrom.* 32, 888-896.
31. Wheelen, P., Zirrolli, J. A. & Murphy, R. C. (1994) *J. Am. Soc. Mass Spectrom.* 6, 40-51.
32. d'Ischia, M., Rega, N. & Barone, V. (1999) *Tetrahedron* 55, 9297-9308.
33. Ranu, B. C. & Chakraborty, R. (1991) *Tetrahedron Letters* 32, 3579-3582.
34. Gladwin, M. T., Shelhamer, J. H., Schechter, A. N., Pease-Fye, M. E., Waclawiw, M. A., Panza, J. A., Ognibene, F. P. & Cannon, R. O., III (2000) *Proc. Natl. Acad. Sci. U.S.A* 97, 11482-11487.
35. Rassaf, T., Bryan, N. S., Kelm, M. & Feelisch, M. (2002) *Free Radic. Biol. Med.* 32, 1589-1596.
36. Rassaf, T., Bryan, N. S., Maloney, R. E., Specian, V., Kelm, M., Kalyanaraman, B., Rodriguez, J. & Feelisch, M. (2003) *Nat. Med.* 9, 481-482.
37. Cosby, K., Partovi, K. S., Crawford, J. H., Patel, R. P., Reiter, C. D., Martyr, S., Yang, B. K., Waclawiw, M. A., Zalos, G., Xu, X. et al. (2003) *Nat. Med.* 9, 1498-1505.
38. Zelinsky, N. D. & Rosanoff, M. A. (1912) *Z. Physikal Chem.* 78, 629-633.
39. Finlayson-Pitts, B. J., Sweetman, L. L. & Weissbart, B. (1987) *Toxicol. Appl. Pharmacol.* 89, 438-448.
40. Hogg, N., Kalyanaraman, B., Joseph, J., Struck, A. & Parthasarathy, S. (1993) *FEBS Lett.* 334, 170-174.
41. Rubbo, H., Radi, R., Trujillo, M., Telleri, R., Kalyanaraman, B., Barnes, S., Kirk, M. & Freeman, B. A. (1994) *J. Biol. Chem.* 269, 26066-26075.
42. Rubbo, H., Parthasarathy, S., Barnes, S., Kirk, M., Kalyanaraman, B. & Freeman, B. A. (1995) *Arch. Biochem. Biophys.* 324, 15-25.
43. Foster, M. W., McMahon, T. J. & Stamler, J. S. (2003) *Trends Mol. Med.* 9, 160-168.
44. Schopfer, F. J., Baker, P. R. & Freeman, B. A. (2003) *Trends Biochem. Sci.* 28, 646-654.
45. Coles, B., Bloodsworth, A., Eiserich, J. P., Coffey, M. J., McLoughlin, R. M., Giddings, J. C., Lewis, M. J., Haslam, R. J., Freeman, B. A. & O'Donnell, V. B. (2002) *J. Biol. Chem.* 277, 5832-5840.
46. Lima, E. S., Di Mascio, P., Rubbo, H. & Abdalla, D. S. (2002) *Biochemistry* 41, 10717-10722.
47. Lima, E. S., Di Mascio, P. & Abdalla, D. S. (2003)*J. Lipid Res.* 44, 1660-1666.
48. Knowles, M. E., McWeeny, D. J., Couchman, L. & Thorogood, M. (1974) *Nature* 247, 288-289.
49. Hayama, T., Tomoda, S., Takeuchi, Y. & Nomura, Y. (1982) *Tetrahedron Letters* 23, 4733-4734.

Example 2

Allylic nitro derivatives of linoleic acid (nitrolinoleic acid, $LNO_2$) are formed via nitric oxide-dependent oxidative inflammatory reactions and are found at concentrations of ~500 nM in the blood of healthy individuals. It will be shown that nitrolinoleic acid ($LNO_2$) is a potent endogenous ligand for peroxisome proliferator-activated receptor γ (PPAR γ; $K_i$~133 nM) that acts within physiological concentration ranges. This nuclear hormone receptor (PPARγ) regulates glucose homeostasis, lipid metabolism and inflammation. PPARγ ligand activity is specific for $LNO_2$ and not mediated by $LNO_2$ decay products, NO donors, linoleic acid or oxidized linoleic acid. $LNO_2$ is a significantly more robust PPAR ligand than other reported endogenous PPARγ ligands, including lysophosphatidic acid (LPA 16:0 and LPA 18:1), 15-deoxy-$\Delta^{12,14}$-$PGJ_2$, conjugated linoleic acid and azelaoyl-PC. $LNO_2$ activation of PPAR γ via CV-1 cell luciferase reporter gene expression analysis revealed a ligand activity that rivals or exceeds synthetic PPARγ agonists such as Rosiglitazone and Ciglitazone, is co-activated by 9 cis-retinoic acid and is inhibited by the PPAR γ antagonist GW9662. $LNO_2$ induces PPARγ-dependent macrophage CD-36 expression, adipocyte differentiation and glucose uptake also at a potency rivaling thiazolidinediones. These observations reveal that nitric oxide (•NO)-mediated cell signaling reactions can be transduced by fatty acid nitration products and PPAR-dependent gene expression.

The reaction of nitric oxide (•NO) with tissue free radical and oxidative intermediates yields secondary oxides of nitrogen that mediate oxidation, nitration and nitrosation reactions (1, 2). Of present relevance, the reaction of •NO and •NO-derived species with oxidizing unsaturated fatty acids is kinetically rapid and exerts a multifaceted impact on cell redox and signaling reactions. Nitric oxide readily out-competes lipophilic antioxidants for the scavenging of lipid radicals, resulting in the inhibition of peroxyl radical-mediated chain propagation reactions (3). Both the catalytic activity and gene expression of eicosanoid biosynthetic enzymes are also regulated by •NO, affirming a strong linkage between •NO and fatty acid oxygenation product synthesis and signaling (4, 5). Consistent with this latter precept, fatty acid nitration products generated by •NO-derived species inhibit multiple aspects of inflammatory cell function, indicating that nitrated fatty acids are both byproducts and mediators of redox signaling reactions (6-8).

Recently, the structural characterization and quantitation of nitrolinoleic acid ($LNO_2$) in human red cells and plasma revealed this unsaturated fatty acid derivative to be the most abundant bioactive oxide of nitrogen in the vasculature. Net blood levels of ~80 and 550 nM free and esterified $LNO_2$, respectively, were measured in healthy humans (9). The observation that •NO-dependent oxidative inflammatory reactions yields allylic nitro derivatives of unsaturated fatty acids displaying cGMP-independent cell signaling properties (5) led to the identification of a receptor that can transduce $LNO_2$ signaling. Affymetrix oligonucleotide microarray analysis of cRNA prepared from methanol (vehicle), linoleic acid (LA)- and $LNO_2$-treated human aortic smooth muscle cells indicated that $LNO_2$ specifically and potently regulated the expression of key inflammatory, cell proliferation and cell differentiation-related proteins. Multiple PPARγ target genes were significantly regulated, suggesting that $LNO_2$ serves as an endogenous PPARγ ligand.

PPARγ is a nuclear hormone receptor that binds lipophilic ligands. Downstream effects of PPARγ activation include modulation of metabolic and cellular differentiation genes and regulation of inflammatory responses (e.g., integrin expression, lipid transport by monocytes), adipogenesis and glucose homeostasis (10, 11). In the vasculature, PPARγ is expressed in monocytes, macrophages, smooth muscle cells and endothelium (12) and plays a central role in regulating the expression of genes related to lipid trafficking, cell proliferation and inflammatory signaling(13). While synthetic thiazolidinediones (TZDs) such as Rosiglitazone and Ciglitazone are appreciated to be the most potent PPARγ ligands yet described, considerable interest and debate remains focused on the identity of endogenous PPARγ ligands because of therapeutic potential and their intrinsic value in understanding cell signaling. At present, tissue and plasma levels of putative PPAR ligands are frequently not precisely defined and when so, are found in concentrations sometimes orders of magnitude lower than those required to activate specific α, γ or δ PPAR subtypes (14-16). As set forth herein, the allylic nitro derivatives of fatty acids are robust endogenous PPARγ ligands that act within physiological concentration ranges to modulate key PPARγ-regulated signaling events including adipogenesis, adipocyte glucose homeostasis and CD36 expression in macrophages.

Materials. $LNO_2$ and $[^{13}C]LNO_2$ were synthesized and purified using linoleic acid (NuCheckPrep, Elysian, Minn.) and $[^{13}C]$linoleic acid (Spectra Stables Isotopes, Columbia, Md.) subjected to nitroselenylation as previously described (9). $LNO_2$ concentrations were quantified spectroscopically and by chemiluminescent nitrogen analysis (Antec Instruments, Houston, Tex.) using caffeine as a standard (9). Anti-CD36 antibody (kindly provided by Dr. de Beer at University of Kentucky Medical Center, Lexington, Ky.); anti-PPARγ and anti-β-actin antibodies were from Santa Cruz (Santa Cruz, Calif.); and anti-aP2 antibody was from Chemicon International Inc. (Temecula, Calif.). Horseradish peroxidase-linked goat anti-rabbit IgG and Coomasie Blue were from Pierce (Rockford, Ill.). [$^3$H]Rosiglitazone was from American Radiolabeled Chemical, Inc. (St. Louis, Mo.). [$^3$H] 2-Deoxy-D-glucose was from Sigma (St Louis, Mich.). Scintil-Safe Plus™ 50% was from Fisher Scientific (Pittsburgh, Pa.). Rosiglitazone, Ciglitazone, 15-deoxy-$\Delta^{12,14}$-$PGJ_2$, Conjugated Linoleic Acid (CLA1, CLA2) and GW9662 were from Cayman Chemical (Ann Arbor, Mich.). 1-palmitoyl-2-hydroxy-sn-glycero-3-Phosphate (16:0 LPA), 1-O-9-(Z)-octadecenyl-2-hydroxy-sn-glycero-3-phosphate (18:1 LPA), 1-O-hexadecyl-2-azelaoyl-sn-glycero-3-phosphocholine (azPC), 1-Palmitoy-2-Azelaoyl-sn-Glycero-3-Phosphocholine (azPC Ester) were from Avanti Polar Lipids, Inc. (Alabaster, Ala.).

Cell Transient Transfection Assay. CV-1 cells from ATCC (Manassas, Va.) were grown to ~85% confluence in DMEM/F12 supplemented with 10% FBS, 1% penicillin-streptomycin. Then, cells were transiently co-transfected with a plasmid containing the luciferase gene under regulation by four Gal4 DNA binding elements ($UAS_G$×4 TK-Luciferase, a gift from Dr. Ronald M. Evans), in concert with plasmids containing the ligand binding domain for the different nuclear receptors fused to the Gal4 DNA binding domain. For assessing full-length PPAR receptors, CV-1 cells were transiently co-transfected with a plasmid containing the luciferase gene under the control of three tandem PPAR response elements (PPRE) (PPRE×3 TK-Luciferase) and hPPARγ, hPPARα or hPPARδ expression plasmids, respectively. In all cases, fluorescence protein (GFP) expression plasmid was co-transfected as the control for the transfection efficiency. Twenty-four hours after the transfection, cells were cultured for another 24 hours in Optium-MEM (Invitrogen, Carlsbad, Calif.). Then, cells were treated with different compounds as indicated in figures for 24 hours in Optium-MEM. Reporter luciferase assay kits from Promega (Madison, Wis.) were used to measure the luciferase activity according to the manufacturer's instructions with a luminometer (Victor II, Perkin-Elmer). Luciferase activity was normalized by GFP units. Each condition was performed at least in triplicates in each experiment. All experiments were repeated at least three times.

PPARγ Competition Binding Assay. Human PPARγ1 cDNA was inserted into pGEX from Amersham Biosciences Corp (Piscataway, N.J.) containing the gene encoding glutathione S-transferase (GST). GST-PPARγ protein induction and receptor binding was assessed as previously described (17).

3T3-L1 Differentiation and Oil Red O Staining. 3T3-L1 preadipocytes were propagated and maintained in DMEM containing 10% FBS. To induce differentiation, 2-day postconfluent preadipocytes (designated day 0) were cultured in DMEM containing 10% FBS plus 3 μM $LNO_2$ for 14 days. The medium was changed every two days. Rosiglitazone (3 μM) and linoleic acid (10 μM) were used as the positive and negative control, respectively. The differentiated adipocytes were stained by Oil red O as previously described (18).

[$^3$H]-2-Deoxy-D-glucose Uptake Assay in Differentiated 3T3-L1 Adipocyte. [$^3$H]-2-Deoxy-D-glucose uptake assay as previously described (19) 3T3-L1 preadipocytes were grown in 24-well tissue culture plates, 2-day postconfluent preadipocytes were treated by 10 μg/ml insulin (Sigma), 1 μM dexamethasone (Sigma), and 0.5 mM 3-isobutyl-1-methylxanthine (Sigma) in DMEM containing 10% FBS for two days, then cells were kept in 10 μg/ml insulin also in DMEM containing 10% FBS for 6 days (changed medium every three days). Eight days after induction of adipogenesis, test compounds in DMEM containing 10% FBS were added for an additional 2 days (changed medium every day) and PPARγ-specific antagonist GW9662 were pretreated 1 h before other additions. After two rinses with serum-free DMEM, cells were incubated for 3 h in serum-free DMEM and rinsed at room temperature three times with freshly prepared KRPH buffer (5 mM phosphate buffer, 20 mM HEPES, 1 mM $MgSO_4$, 1 mM $CaCl_2$, 136 mM NaCl, 4.7 mM KCl, pH 7.4). The buffer was replaced with 1 μCi/ml of [$^3$H]-2-deoxy-D-glucose in KRPH buffer for 10 min at room temperature. The treated cells were rinsed carefully three times with cold PBS, lysed overnight in 0.8N NaOH (0.4 ml/well), and neutralized with 13.3 μl of 12N HCl. Lysate (360 μl) was added to 4 ml Scinti-Safe Plus TM 50% in a scintillation vial, and the vials were mixed and counted.

RNA and Protein Preparation and Analysis. RNA and protein expression levels were analyzed by quantitative real-time PCR and Western blot analysis as previously described.[25]

$LNO_2$ decay. $LNO_2$ decay was induced by incubating 3 μM $LNO_2$ in medium+serum at 37° C. At different times, samples were removed and analyzed for bioactivty or for LNO$_2$ content by Bligh and Dyer extraction in the presence of 1 μM [$^{13}$C] LNO$_2$ as an internal standard. Non-decayed LNO$_2$ was quantified via triple quadrupole mass spectrometric analysis (Applied Biosystems/MDS Sciex, Thornhill, Ontario, Canada) as previously reported (9).

Figure 7:
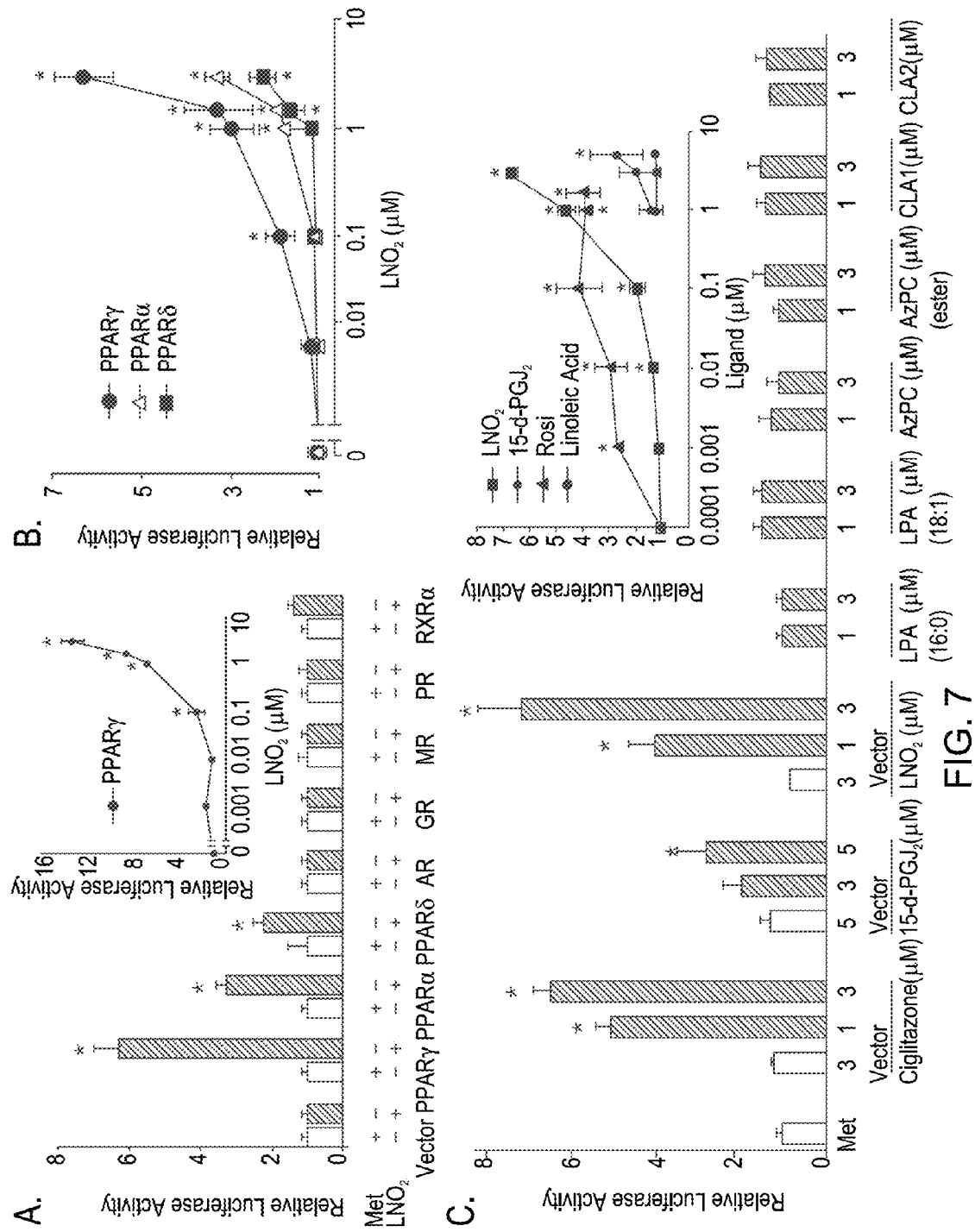
FIG. 7 shows that $LNO_2$ is a potent PPAR ligand. (A) CV-1 cells, transiently co-transfected with different nuclear receptor ligand binding domains fused to the Gal4 DNA binding domain and the luciferase reporter gene under the control of four Gal4 DNA binding elements, were incubated with vehicle (methanol) or $LNO_2$ (3 μM, 2 hr, n=4). (A, inset) Dose-response of $LNO_2$-dependent PPARγ ligand binding domain activation (n=4). (B) Dose-response of $LNO_2$-dependent PPARγ, α and δ activation (n=4). The luciferase reporter gene was under the control of three PPAR response elements (C) Response of CV-1 cells transfected with PPARγ and a luciferase reporter construct under the control of PPRE following exposure to $LNO_2$ and other reported PPARγ ligands (1 and 3 μM each of ciglitazone, 15-deoxy-$\Delta^{12,14}$-$PGJ_2$, 1-palmitoyl-2-hydroxy-sn-glycero-3-phosphocholine (LPA 16:0), 1-oleoyl-2-hydroxy-sn-glycero-3-phosphocholine (LPA 18:1), 1-O-hexadecyl-2-azelaoyl-sn-glycero-3-phosphocholine (AzPC), 1-palmitoyl-2-azelaoyl-sn-glycero-3-phosphocholine (azPC ester), $\Delta^{9,11}$-conjugated linoleic acid (CLA-1) and $\Delta^{10,12}$-conjugated linoleic acid (CLA-2), with (n=3 to 5). "Vector" indicates empty vector (C, inset) Using the same reporter construct, the dose response of PPARγ activation by $LNO_2$, rosiglitazone, 15-deoxy-$\Delta^{12,14}$-$PGJ_2$ and linoleic acid was measured (n=3). All values are expressed as mean±SD. (*) represents significantly different (P<0.05) from vehicle control using Student's t test. All experiments were repeated at least three times.

To characterize LNO$_2$ as a potential ligand for a lipid-binding nuclear receptor [e.g., PPARα, PPARγ, PPARδ, androgen receptor (AR), glucocorticoid receptor (GR), mineralocorticoid receptor (MR), progesterone receptor (PR) and retinoic X receptor α (RXRα)], CV-1 reporter cells were co-transfected with plasmids containing the ligand binding domain for these nuclear receptors fused to the Gal4 DNA binding domain and the luciferase gene under regulation of four Gal4 DNA binding elements. LNO$_2$ (1 μM) induced significant activation of PPARγ (620%), PPARα (325%) and PPARδ (221%), with no impact on AR, GR, MR, PR or RXRα receptor activation (FIG. 7A). To further explore PPAR activation by LNO$_2$, CV-1 cells were transiently co-transfected with a plasmid containing the luciferase gene under three PPAR response elements (PPRE) in concert with PPARγ, PPARα or PPARδ expression plasmids. Dose-dependent activation by LNO$_2$ was observed for all PPARs by LNO$_2$ (FIG. 7B), with PPARγ showing the greatest response at clinically-relevant concentrations of LNO$_2$.

Figure 8:
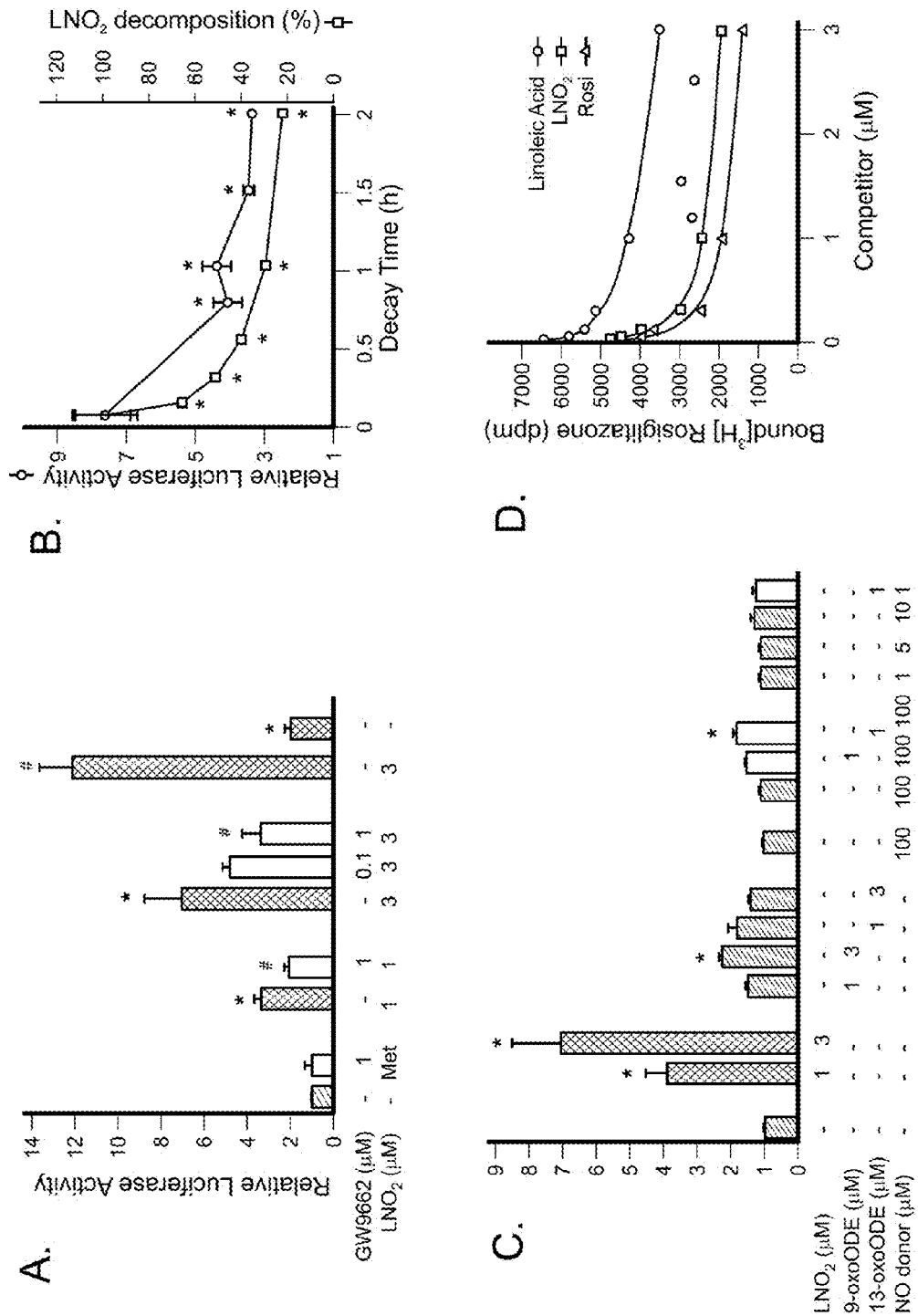
FIG. 8 shows the characterization of the PPARγ ligand activity of $LNO_2$. (A) Using CV-1 cells cotransfected with PPARγ and PPRE-controlled luciferase expression plasmids, the activation of PPARγ by $LNO_2$ was evaluated in the absence or presence of PPARγ-specific antagonist GW9662 added 1 hr prior to $LNO_2$ addition or upon co-addition of the RXR receptor co-activating ligand 9-cis-retinoic acid (n=3). PPARγ activation by $LNO_2$ was inhibited in a dose-dependent manner by GW9662 and was enhanced in the presence of the coactivator 9-cis-retinoic acid. (B) The action of $LNO_2$ as a PPARγ ligand was compared with $LNO_2$-derived decay products. Effective $LNO_2$ concentrations after selected decay periods were measured by LC-MS with electrospray ionization using [$^{13}$C]$LNO_2$ as internal standard (9). PPARγ activation was assessed via PPRE reporter analysis in CV-1 cells. (n=3) (c) Potential PPAR ligand activity of $LNO_2$ decay products was measured via PPRE reporter analysis (n=4) (D) Competition of $LNO_2$, linoleate and unlabeled Rosiglitazone for PPARγ-bound [$^3$H] Rosiglitazone. For (A-C), all values are expressed as mean±SD. (*) represents significantly different (P<0.05) from vehicle control, and (#) represents significantly different from $LNO_2$ alone, using Student's t test. All experiments were repeated at least three times.

PPARγ activation by LNO$_2$ rivaled that induced by Ciglitazone and Rosiglitazone and exceeded that of 15-deoxy-$\Delta^{12,14}$-PGJ$_2$ (20, 21), which only occurred at concentrations 3 orders of magnitude greater than found clinically (FIG. 7C and inset). Several other reported endogenous PPARγ activators added in equimolar concentration with LNO$_2$ [linoleic acid (LA), conjugated linoleic acid (CLA1, CLA2), lysophosphatidic acid (LPA-16:0, LPA-18:1), azPC (azelaoylPC) and azPC ester; 1 and 3 μM], displayed no significant activation of PPARγ reporter gene expression when compared with vehicle control (FIG. 7C) (22-24) LNO$_2$-mediated PPARγ activation was inhibited by the PPARγ-specific antagonist GW9662 and enhanced ~180% by co-addition of the RXRα agonist 9-cis-retinoic acid, which facilitates PPRE promoter activation via heterodimerization of activated RXRα with PPARγ (FIG. 8A).

LNO$_2$ slowly undergoes decay reactions in aqueous solution, displaying a 30-60 min half-life (FIG. 8B) and yielding •NO and an array of oxidation products. The activation of PPARγ paralleled the presence and concentration of the LNO$_2$ parent molecule, as determined by concomitant receptor activation analysis and mass spectrometric quantitation of residual LNO$_2$ in reaction mixtures undergoing different degrees of aqueous decomposition prior to addition to CV-1 cells (FIG. 8B). Affirmation that activation of PPARγ is LNO$_2$-specific, rather than a consequence of LNO$_2$ decay products, was established by treatment of PPARγ-transfected CV-1 cells with •NO donors and oxidized linoleic acid derivatives. Additionally, the fatty acid oxidation products 9- and 13-oxoODE are reported endogenous PPARγ stimuli (25-27). 13-oxoODE had no effect on PPARγ-dependent reporter gene expression (FIG. 8C). Only high and non-physiological concentrations of 9-oxoODE, and the concerted addition of high concentrations of 13-oxoODE and S-nitrosoglutathione or spermine-NONOate, resulted in modest PPARγ activation (FIG. 8C). The •NO donors added individually did not activate PPARγ, even at high concentrations, eliminating the possibility that PPARγ-mediated signaling by LNO$_2$ is due to •NO derivatives released during LNO$_2$ decay (FIG. 8C).

Competitive PPARγ binding analysis quantified the displacement of [$^3$H]Rosiglitazone by unlabeled Rosiglitazone, LNO$_2$ and linoleic acid. The calculated binding affinity (Ki) for Rosiglitazone was 53 nM, consistent with reported values (FIG. 8D, 40-50 nM (28)). LNO$_2$ displayed an estimated Ki of 133 nM and linoleic acid an estimated Ki of >1,000 nM (previously reported as 1.7 to 17 μM (28)). This reveals that the Ki for LNO$_2$ displacement of [$^3$H]Rosiglitazone from PPARγ is comparable to this highly avid ligand.

Figure 9:
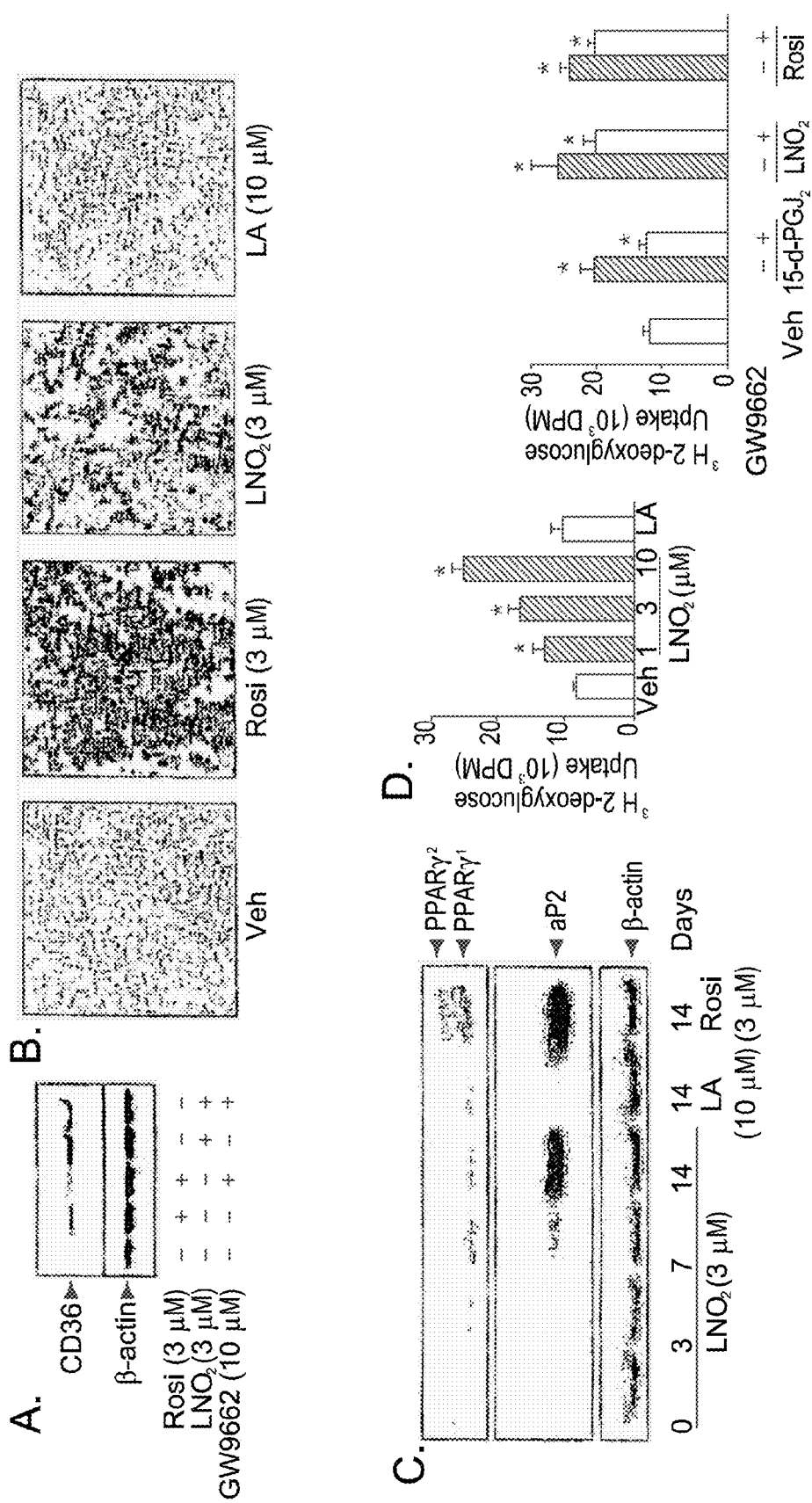
FIG. 9 shows that $LNO_2$ induces CD36 expression in macrophages and adipogenesis of 3T3-L1 preadipocytes. (A) Mouse RAW264.7 macrophages at ~90% confluence were cultured in DMEM with 1% FBS for 16 hours and then treated with various stimuli for 16 hours as indicated. The PPARγ-specific antagonist GW9662 was added 1 h prior to the treatment. The cell lysate was immunoblotted with anti-CD36 and anti-β-actin antibodies. (B,C) Two days after reaching confluence, 3T3-L1 preadipocytes were cultured for 14 days and stained using Oil red O as previously(18) (B) or treated with various stimuli as indicated and the cell lysate was immunoblotted with anti-PPARγ, anti-aP2 and anti-β-actin antibodies (C). (D) $LNO_2$ increases [$^3$H]-2-deoxy-D-glucose uptake in 3T3-L1 adipocytes. Left panel: The dose-dependent effects of LNO2O on [$^3$H]-2-deoxy-D-glucose uptake in 3T3-L1 adipocytes. Right panel: PPARγ-specific antagonist GW9662 was added 1 h before the treatment. [$^3$H]-2-deoxy-D-glucose uptake assay was performed as described in supplemental methods. All experiments were repeated at least three times. Values are expressed as mean±SD (n=6). Statistical analysis was done by using Student's t test (*p<0.05 vs vehicle control; #p<0.05 vs GW9662 untreated groups). Vehicle (Veh); Rosiglitazone (Rosi); 15-deoxy-$PGJ_2$ (15-d-$PGJ_2$); linoleic acid (LA).

The PPARγ agonist actions of LNO$_2$ were also examined in a biological context, using cell models noted for well-established PPARγ-dependent functions. The scavenger receptor CD36 is expressed in diverse cell types, including platelets, adipocytes and macrophages. In macrophages, CD36 is a receptor for oxidized LDL, with expression positively regulated by PPAR (29). Treatment of mouse RAW264.7 macrophages with LNO$_2$ induced greater CD36 receptor protein expression than an equivalent Rosiglitazone concentration, a response partially inhibitable by the PPARγ-specific antagonist GW9662 (FIG. 9A). Moreover, quantitative real-time PCR revealed that LNO$_2$-dependent PPAR transactivation induced a dose-dependent increase in CD36 mRNA expression in these macrophages.

PPARγ plays an essential role in the differentiation of adipocytes (30, 31). In support of this precept, selective disruption of PPARγ results in impaired development of adipose tissue (18, 32). To define if LNO$_2$ induces PPARγ-activated adipogenesis, 3T3-L1 preadipocytes were treated with LNO$_2$, Rosiglitazone or linoleic acid for two weeks. Adipocyte differentiation was assessed both morphologically and via oil red O staining, which reveals the accumulation of intracellular lipids. Vehicle and linoleic acid did not affect differentiation, while LNO$_2$ induced >30% of 3T3-L1 preadiopcyte differentiation (FIG. 9B). Rosiglitazone treatment affirmed a positive PPARγ-dependent response. LNO$_2$ and Rosiglitazone-induced preadipocyte differentiation also resulted in expression of specific adipocyte markers (PPARγ2 and aP2), an event not detected for linoleic acid (FIG. 9C). PPARγ ligands play a central role in glucose metabolism, with TZDs widely used as insulin-sensitizing drugs. Addition of LNO$_2$ (1-10 μM) to differentiated adipocytes induced a dose-dependent increase in glucose uptake (FIG. 9D, Left panel). The impact of LNO$_2$ on glucose uptake was greater than that observed for equimolar 15-deoxy-PGJ$_2$, equivalent to Rosiglitazone and similarly inhibited by the PPARγ-specific antagonist GW9662 (FIG. 9D, Right panel). In aggregate, these observations establish that LNO$_2$ induces well-characterized PPARγ-dependent signaling actions towards macrophage CD36 expression and adipogenesis.

The identification of bona fide high affinity endogenous PPARγ ligands has been a provocative issue that, when resolved, will advance our understanding of endogenous PPARγ modulation and can reveal new means for intervention in diverse metabolic disorders and disease processes. This will also shed light on the broader contributions of this nuclear hormone receptor family to both the maintenance of tissue homeostasis and the regulation of cell and organ dysfunction. Of relevance, the generation of PPAR-activating intermediates from complex lipids often requires hydrolysis by phospholipase A$_2$ (PLA$_2$), with the identity of phospholipid sn-2 position fatty acid derivatives that might serve as PPAR agonists still forthcoming (33, 34). Thus, the fact that ~80% of LNO$_2$ present in a variety of tissue compartments is esterified encourages the notion that this pool of high affinity PPAR ligand activity will be mobilized upon the PLA$_2$ activation that occurs during inflammation to regulate the formation of cell signaling molecules.

Comparison of PPARγ-dependent gene expression induced by LNO$_2$ with that of TZDs and putative fatty acid- and phospholipid-derived PPARγ ligands further affirmed the robust activity of LNO$_2$ as a PPARγ ligand. While a number of endogenous lipophilic species are proposed as PPARγ ligands, their intrinsically low binding affinities and in vivo concentrations do not support a capability to serve as physiologically-relevant signaling mediators. Presently-reported endogenous PPARγ agonists include free fatty acids, components of oxidized plasma lipoproteins (9- and 13-oxoODE, azPC), conjugated linoleic acid derivatives (CLA1 and CLA2), products of phospholipase hydrolysis of complex lipids (LPA), platelet activating factor (PAF) and eicosanoid derivatives such as the dehydration product of PGD$_2$, 15-deoxy-$\Delta^{12,14}$-PGJ$_2$ (14, 22, 23). Herein, minimal or no activation of PPARγ reporter gene expression by 1-3 μM concentrations of these putative ligands was observed, in contrast to the dose-dependent PPAR activation by LNO$_2$ that, for PPARγ, was significant at clinically-relevant concentrations as low as 100 nM. A dilemma exists in that some putative endogenous PPARγ agonists have only been generated by aggressive in vitro oxidizing conditions (e.g., Cu-mediated LDL oxidation) and have not been clinically quantified or detected (for instance, azPC, CLA). Other lipid derivatives proposed as PPAR ligands are present in <100 nM tissue concentrations, orders of magnitude below their binding affinities (1-15 μM) and are not expected to result in significant receptor occupancy and activation in vivo. This latter category includes free fatty acids, eicosanoids, 9- and 13-oxoODE, PAF and 15-deoxy-$\Delta^{12,14}$-PGJ$_2$ (14). For example, while LPA is a notable PPAR ligand of relevance to vascular, inflammatory and cell proliferative diseases the plasma concentration of LPA is well below 100 nM (35, 36) and its binding affinity for PPAR has not been established. Also, the in vivo downstream vascular signaling actions of LPA are inconsistent with its proposed PPARγ ligand activity (24, 37-39). Future studies using mice genetically deficient for PPARγ and NOS isoforms should assist in defining the mechanisms of formation and endogenous PPAR ligand activity of nitrated fatty acids.

In summary, LNO$_2$ is a high affinity ligand for PPARs, especially PPARγ, that activates both reporter constructs and cells at physiological concentrations. Fatty acid nitration products, generated by •NO-dependent reactions, are thus expected to display broad cell signaling capabilities as endogenous nuclear receptor-dependent paracrine signaling molecules with a potency that rivals TZDs (FIG. 7C). Present data reveals that LNO$_2$ mediates cell differentiation in adipocytes, CD36 expression in macrophages, and inflammatory-related signaling events in endothelium (e.g., inhibition of VCAM-1 expression and function, not shown) with an important contribution from PPARγ-dependent mechanisms (FIG. 9A-D). Allylic nitro derivatives of fatty acids thus represent a unique class of receptor-dependent cell differentiation, metabolic and anti-inflammatory signaling molecules that serve to converge •NO and oxygenated lipid redox signaling pathways.

Throughout Example 2, several publications have been referenced. These publications are listed in the Reference List for Example 2. The disclosures of these publications in their entireties are hereby incorporated by reference into this application in order to more fully describe the compounds, compositions and methods described herein.

REFERENCE LIST FOR EXAMPLE 2

1. Schopfer, F. J., Baker, P. R. & Freeman, B. A. (2003) *Trends Biochem. Sci.* 28, 646-654.
2. Hogg, N. (2002) *Annu. Rev. Pharmacol. Toxicol.* 42, 585-600.
3. Rubbo, H., Radi, R., Anselmi, D., Kirk, M., Barnes, S., Butler, J., Eiserich, J. P. & Freeman, B. A. (2000) *J. Biol. Chem.* 275, 10812-10818.
4. Marnett, L. J., Wright, T. L., Crews, B. C., Tannenbaum, S. R. & Morrow, J. D. (2000) *J. Biol. Chem.* 275, 13427-13430.
5. O'Donnell, V. B. & Freeman, B. A. (2001) *Circ. Res.* 88, 12-21.
6. Coles, B., Bloodsworth, A., Eiserich, J. P., Coffey, M. J., McLoughlin, R. M., Giddings, J. C., Lewis, M. J., Haslam, R. J., Freeman, B. A. & O'Donnell, V. B. (2002) *J. Biol. Chem.* 277, 5832-5840.
7. Coles, B., Bloodsworth, A., Clark, S. R., Lewis, M. J., Cross, A. R., Freeman, B. A. & O'Donnell, V. B. (2002) *Circ. Res.* 91, 375-381.
8. Rubbo, H., Radi, R., Trujillo, M., Telleri, R., Kalyanaraman, B., Barnes, S., Kirk, M. & Freeman, B. A. (1994) *J. Biol. Chem.* 269, 26066-26075.
9. Baker, P. R., Schopfer, F. J., Sweeney, S. & Freeman, B. A. (2004) *Proc. Natl. Acad. Sci. U.S.A* 101, 11577-11582.
10. Lee, C. H. & Evans, R. M. (2002) *Trends Endocrinol. Metab.* 13, 331-335.
11. Marx, N., Duez, H., Fruchart, J. C. & Staels, B. (2004) *Circ. Res.* 94, 1168-1178.
12. Wang, N., Verna, L., Chen, N. G., Chen, J., Li, H., Forman, B. M. & Stemerman, M. B. (2002) *J. Biol. Chem.* 277, 34176-34181.
13. Chen, Y. E., Fu, M., Zhang, J., Zhu, X., Lin, Y., Akinbami, M. A. & Song, Q. (2003) *Vitam. Horm.* 66, 157-188.
14. Bell-Parikh, L. C., Ide, T., Lawson, J. A., McNamara, P., Reilly, M. & FitzGerald, G. A. (2003) *J. Clin. Invest.* 112, 945-955.
15. Rosen, E. D. & Spiegelman, B. M. (2001) *J Biol. Chem.* 276, 37731-37734.
16. Tzameli, I., Fang, H., Ollero, M., Shi, H., Hamm, J. K., Kievit, P., Hollenberg, A. N. & Flier, J. S. (2004) *J. Biol. Chem.*
17. Fu, J., Gaetani, S., Oveisi, F., Lo, V. J., Serrano, A., Rodriguez, D. F., Rosengarth, A., Luecke, H., Di Giacomo, B., Tarzia, G. et al. (2003) *Nature* 425, 90-93.
18. Zhang, J., Fu, M., Cui, T., Xiong, C., Xu, K., Zhong, W., Xiao, Y., Floyd, D., Liang, J., Li, E. et al. (2004) *Proc. Natl. Acad. Sci. U. S. A* 101, 10703-10708.
19. Mukherjee, R., Hoener, P. A., Jow, L., Bilakovics, J., Klausing, K., Mais, D. E., Faulkner, A., Croston, G. E. & Paterniti, J. R., Jr. (2000) *Mol. Endocrinol.* 14, 1425-1433.
20. Forman, B. M., Tontonoz, P., Chen, J., Brun, R. P., Spiegelman, B. M. & Evans, R. M. (1995) *Cell* 83, 803-812.
21. Kliewer, S. A., Lenhard, J. M., Willson, T. M., Patel, I., Morris, D. C. & Lehmann, J. M. (1995) *Cell* 83, 813-819.
22. Davies, S. S., Pontsler, A. V., Marathe, G. K., Harrison, K. A., Murphy, R. C., Hinshaw, J. C., Prestwich, G. D., Hilaire, A. S., Prescott, S. M., Zimmerman, G. A. et al. (2001) *J. Biol. Chem.* 276, 16015-16023.
23. McIntyre, T. M., Pontsler, A. V., Silva, A. R., St Hilaire, A., Xu, Y., Hinshaw, J. C., Zimmerman, G. A., Hama, K., Aoki, J., Arai, H. et al. (2003) *Proc. Natl. Acad. Sci. U.S.A* 100, 131-136.
24. Zhang, C., Baker, D. L., Yasuda, S., Makarova, N., Balazs, L., Johnson, L. R., Marathe, G. K., McIntyre, T. M., Xu, Y., Prestwich, G. D. et al. (2004) *J. Exp. Med.* 199, 763-774.

25. Kliewer, S. A., Sundseth, S. S., Jones, S. A., Brown, P. J., Wisely, G. B., Koble, C. S., Devchand, P., Wahli, W., Willson, T. M., Lenhard, J. M. et al. (1997) *Proc. Natl. Acad. Sci. U. S. A* 94, 4318-4323.
26. Nagy, L., Tontonoz, P., Alvarez, J. G., Chen, H. & Evans, R. M. (1998) *Cell* 93, 229-240.
27. Von Knethen, A. & Brune, B. (2002) *J. Immunol.* 169, 2619-2626.
28. Ferry, G., Bruneau, V., Beauverger, P., Goussard, M., Rodriguez, M., Lamamy, V., Dromaint, S., Canet, E., Galizzi, J. P. & Boutin, J. A. (2001) *Eur. J. Pharmacol.* 417, 77-89.
29. Chawla, A., Barak, Y., Nagy, L., Liao, D., Tontonoz, P. & Evans, R. M. (2001) *Nat. Med.* 7, 48-52.
30. Tontonoz, P., Hu, E., Graves, R. A., Budavari, A. I. & Spiegelman, B. M. (1994) *Genes Dev.* 8, 1224-1234.
31. Tontonoz, P., Hu, E. & Spiegelman, B. M. (1994) *Cell* 79, 1147-1156.
32. Evans, R. M., Barish, G. D. & Wang, Y. X. (2004) *Nat. Med.* 10, 355-361.
33. Delerive, P., Furman, C., Teissier, E., Fruchart, J., Duriez, P. & Staels, B. (2000) *FEBS Lett.* 471, 34-38.
34. Pawliczak, R., Han, C., Huang, X. L., Demetris, A. J., Shelhamer, J. H. & Wu, T. (2002) *J. Biol. Chem.* 277, 33153-33163.
35. Saulnier-Blache, J. S., Girard, A., Simon, M. F., Lafontan, M. & Valet, P. (2000) *J. Lipid Res.* 41, 1947-1951.
36. Xu, Y., Shen, Z., Wiper, D. W., Wu, M., Morton, R. E., Elson, P., Kennedy, A. W., Belinson, J., Markman, M. & Casey, G. (1998) *JAMA* 280, 719-723.
37. Chen, Z., Ishibashi, S., Perrey, S., Osuga, J., Gotoda, T., Kitamine, T., Tamura, Y., Okazaki, H., Yahagi, N., Iizuka, Y. et al. (2001) *Arterioscler. Thromb. Vasc. Biol.* 21, 372-377.
38. Claudel, T., Leibowitz, M. D., Fievet, C., Tailleux, A., Wagner, B., Repa, J. J., Torpier, G., Lobaccaro, J. M., Paterniti, J. R., Mangelsdorf, D. J. et al. (2001) *Proc. Natl. Acad. Sci. U.S.A* 98, 2610-2615.
39. Collins, A. R., Meehan, W. P., Kintscher, U., Jackson, S., Wakino, S., Noh, G., Palinski, W., Hsueh, W. A. & Law, R. E. (2001) *Arterioscler. Thromb. Vasc. Biol.* 21, 365-371.

Example 3

The synthesis, structural characterization, clinical quantitation and cell signaling activity of nitrated oleic acid ($OA-NO_2$) are reported. Analysis of plasma and urine also revealed the presence of additional nitrated fatty acids, including nitrated linolenic, arachidonic, eicosapentaenoic and docosahexaenoic acids and multiple nitrohydroxy derivatives, which reveal the ubiquity of nitrated fatty acid derivatives in humans. Two nitroalkene derivatives of oleic acid were synthesized (9- and 10-nitro-9-cis-octadecenoic acid), structurally characterized and compared with nitrated fatty acids present in plasma, red cells and urine of healthy humans. Based on HPLC elution and mass spectrometric characteristics, these two regioisomers of $OA-NO_2$ were identified in clinical samples. Using $^{13}C$ isotope dilution, $OA-NO_2$ was quantitated, with plasma free and esterified levels of 619±52 and 302±369 nM, respectively. In red blood cells, free and esterified $OA-NO_2$ was 59±11 and 155±65 nM, respectively. Assuming a 40% hematocrit, $OA-NO_2$ levels are ~50% greater than that of nitrated linoleic acid; with combined free and esterified levels of these two nitroalkene derivatives exceeding 1 µM. $OA-NO_2$ potently activated peroxisome proliferator activated receptor-γ and induced PPAR γ-dependent adipogenesis and deoxyglucose uptake in 3T3 L1 preadipocytes. These data reveal that multiple nitrated fatty acids comprise a class of •NO and fatty acid-derived signaling molecules.

The oxidation of unsaturated fatty acids converts lipids, otherwise serving as cell metabolic precursors and structural components, into potent signaling molecules including prostaglandins, leukotrienes, isoprostanes, hydroxy- and hydroperoxy-eicosatetraenoates and platelet-activating factor. This process, either enzymatic or auto-oxidative, orchestrates immune responses, neurotransmission and the regulation of cell growth. For example, prostaglandins are cyclooxygenase-derived lipid mediators that signal via receptor-ligand interactions to regulate inflammatory responses, vascular function, initiation of parturition, cell survival and angiogenesis (1). In contrast, the various isoprostane products of arachidonic acid auto-oxidation exert vasoconstrictive and pro-inflammatory signaling actions via both receptor-dependent and -independent mechanisms (2). A common element of these diverse lipid signaling actions is that nitric oxide (•NO) and other reactive nitrogen species significantly impact lipid mediator formation and bioactivities.

The ability of •NO and •NO-derived reactive species to oxidize, nitrosate and nitrate biomolecules suggests that •NO might also influence the synthesis and reactions of bioactive lipids (3-5). Interactions between •NO and lipid oxidation pathways are multifaceted and interdependent. For example, •NO regulates both the activity and expression of prostaglandin H synthase (6). Conversely, leukotriene products of lipoxygenases induce nitric oxide synthase-2 expression to increase •NO production (7). Furthermore, the autocatalytic chain propagation reactions of lipid peroxyl radicals during membrane and lipoprotein oxidation are potently inhibited by •NO (8). Of relevance, reactions between •NO-derived species and lipid oxidation intermediates yield nitrated fatty acids. Recently, the nitroalkene derivative of linoleic acid ($LNO_2$) has been detected in human blood at concentrations sufficient to induce biological responses (~500 nM, refs. (9-12)). Compared with other •NO-derived species such as nitrite ($NO_2^-$), nitrosothiols (RSNO) and heme-nitrosyl complexes, $LNO_2$ represents the single most abundant pool of bioactive oxides of nitrogen in the healthy human vasculature (9,13-16).

In vitro studies have shown that $LNO_2$ mediates cGMP-dependent vascular relaxation, cGMP-independent inhibition of neutrophil degranulation and superoxide formation, and inhibition of platelet activation (10-12). Recently, $LNO_2$ has been shown to exert cell signaling actions via ligation and activation of peroxisome proliferator activated receptors (PPAR) (17), a class of nuclear hormone receptors that modulates the expression of metabolic and cellular differentiation and inflammatory-related genes (18,19).

Figure 10:
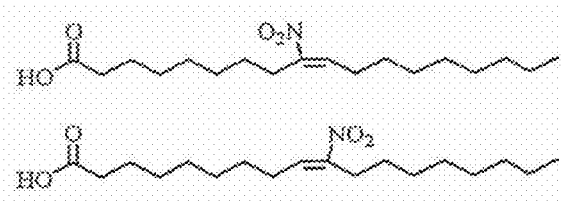
FIG. 10 shows nitrated oleic acid (OA-$NO_2$). Two regioisomers of OA-$NO_2$ were synthesized by nitrosenylation of oleic acid and purified as described in Experimental Procedures, generating 9- and 10-nitro-9-cis-octadecenoic acids.

The identification of $LNO_2$ as an endogenous PPARγ ligand that acts within physiologically-relevant concentrations motivated a search for other nitrated lipids that might serve related signaling actions. Herein, fatty acid nitroalkene products in plasma and urine are abundant and ubiquitous are reported. Of the total fatty acid content in red cells, linoleic acid and oleic acid comprise ~8% and ~18%, respectively (20). Thus, due to its prevalence and structural simplicity, oleic acid was evaluated as a potential candidate for nitration. Herein, reported is the synthesis, structural characterization and cell signaling activity of 9- and 10-nitro-9-cis-octadecaenoic acids (nitrated oleic acid; $OA-NO_2$; FIG. 10) and that $OA-NO_2$ regioisomers are present in human blood at levels exceeding those of $LNO_2$. Furthermore, $OA-NO_2$ activates PPARγ with a greater potency than LNO$_2$. These data reveal that nitrated unsaturated fatty acids represent a novel class of lipid-derived, receptor-dependent signaling mediators.

Methods

Materials. 9-Octadecenoic acid (oleic acid) and its respective methyl ester, methyl-9-octadecenoate was purchased from Nu-Check Prep (Elysian, Minn.). LNO$_2$ and [$^{13}$C] LNO$_2$ were synthesized as previously described (9,12); OA-NO$_2$ and [$^{13}$C]OA-NO$_2$ were synthesized as described in below. Phenylselenium bromide, HgCl$_2$, NaNO$_2$, anhydrous tetrahydrofuran (THF), CH$_3$CN, CDCl$_3$, insulin, dexamethasone and 3-isobutyl-1-methylxanthine were obtained from Sigma/Aldrich (St Louis, Mo.). Silica gel G and HF thin layer chromatography plates (250 and 2000 m) were from Analtech (Newark, Del.). Methanolic BF$_3$, horseradish peroxidase-linked goat anti-rabbit IgG and Coomasie Blue were from Pierce (Rockford, Ill.). Synthetic solvents were of HPLC grade or better from Fisher Scientific (Fairlawn, N.J.). Solvents used for extractions and mass spectrometric analyses were from Burdick and Jackson (Muskegon, Mich.). [$^{13}$C]Oleic acid and [$^{13}$C]linoleic acid were purchased from Cambridge Isotope Laboratories, Inc. (Andover, Mass.). Anti-PPARγ and anti-j-actin antibodies were from Santa Cruz (Santa Cruz, Calif.); anti-aP2 antibody was from Chemicon International Inc. (Temecula, Calif.).

Synthesis of OA-NO$_2$. Oleic acid and [$^{13}$C]oleic acid were nitrated as described (9,12), with modifications. Briefly, oleic acid, HgCl$_2$, phenylselenium bromide and NaNO$_2$ (1:1.3:1:1, mol/mol) were combined in THF/acetonitrile (1:1, v/v) with a final concentration of 0.15 M oleic acid. The reaction mixture was stirred (4 h, 25° C.), followed by centrifugation to sediment the precipitate. The supernatant was recovered, the solvent evaporated in vacuo, the product mixture redissolved in THF (original volume) and the temperature reduced to 0° C. A ten-fold molar excess of H$_2$O$_2$ was slowly added with stirring to the mixture, which was allowed to react in an ice bath for 20 min followed by a gradual warming to room temp (45 min). The product mixture was extracted with hexane, the organic phase collected, the solvent removed in vacuo and lipid products solvated in CH$_3$OH. OA-NO$_2$ was isolated by preparative TLC using silica gel HF plates developed twice in a solvent system consisting of hexane/ether/acetic acid (70:30:1, v/v). The region of silica containing OA-NO$_2$ was scraped and extracted (21). Based on this synthetic rationale, two regioisomers are generated: 9- and 10-nitro-9-cis-octadecenoic acids (generically termed OA-NO$_2$). Thin layer chromatography does not resolve the two isomers. [$^{13}$C]OA-NO$_2$ was synthesized using [$^{13}$C]oleic acid as a reactant. Stock concentrations of OA-NO$_2$ isomers were quantitated by chemiluminescent nitrogen analysis (Antek Instruments, Houston, Tex.), using caffeine as a standard. All standards were diluted in methanol, aliquoted and stored under argon gas at −80° C. Under these conditions, OA-NO$_2$ isomers remain stable for >3 months.

OA-NO$_2$ spectrophotometric characterization. OA-NO$_2$ stock solution concentrations were initially determined by chemiluminescent nitrogen analysis. These data were utilized to determine dilution concentrations for subsequent spectral analysis. An absorbance spectrum of OA-NO$_2$ from 200-450 nm was generated using 23 μM OA-NO$_2$ in phosphate buffer (100 mM, pH 7.4) containing 100 μM DTPA. The extinction coefficients (E) for OA-NO$_2$ and the isotopic derivative [$^{13}$C]OA-NO$_2$ were measured ($\lambda_{270}$) using a UV-VIS spectrophotometer (Shimadzu, Japan). Absorbance values for increasing concentrations of OA-NO$_2$ and [$^{13}$C]OA-NO$_2$ were plotted against concentration to calculate ε.

NMR spectrometric analysis of OA-NO$_2$-$^1$H and $^{13}$C NMR spectra were measured using a Varian INOVA 300 and 500 MHz NMR and recorded in CDCl$_3$. Chemical shifts are in δ units (ppm) and referenced to residual proton (7.26 ppm) or carbon (77.28 ppm) signals in deuterated chloroform. Coupling constants (J) are reported in Hertz (Hz).

Gas chromatography mass spectrometric characterization of OA-NO$_2$. Methyl esters of purified synthetic OA-NO$_2$ regioisomers were analyzed by electron impact ionization gas chromatography mass spectrometry (EI GC-MS). Fatty acid methyl esters of OA-NO$_2$ were synthesized, extracted with hexane, washed twice with saturated saline, redissolved in undecane and analyzed by GC-MS using a Saturn 2000 Tandem Mass Spectrometer coupled to a Varian 3800 Gas Chromatograph. Samples were ionized by electron impact at +70 eV. The methyl ester-derivatized OA-NO$_2$ regioisomers were resolved using a 30 m capillary column (5% phenyl 95% dimethylpolysiloxane; CP-Sil 8CB-MS, Varian) with the following temperature gradient: 80° C. (2 min); 80 to 170° C. at 20° C./min; 170 to 240° C. at 2° C./min and 240 to 280° C. at 5° C./min. Helium was used as a carrier gas.

Structural characterization of OA-NO$_2$ by electrospray ionization triple quadrupole mass spectrometry (ESI MS/MS). Qualitative analysis of OA-NO$_2$ by ESI MS/MS was performed using a hybrid triple quadrupole-linear ion trap mass spectrometer (4000 Q trap, Applied Biosystems/MDS Sciex). To characterize synthetic and endogenous OA-NO$_2$, a reverse-phase HPLC separation was developed using a 150×2 mm C18 Phenomenex Luna column (3 μm particle size). Lipids were eluted from the column using a gradient solvent system consisting of A (H$_2$O containing 0.1% NH$_4$OH) and B (CNCH$_3$ containing 0.1% NH$_4$OH) under the following conditions: 20 to 65% B (10 min); 65 to 95% B (1 min; hold for 3 min) and 95 to 20% B (1 min; hold for 3 min). Using these gradient conditions, OA-NO$_2$ elutes after LNO$_2$ positional isomers. OA-NO$_2$ was detected using a multiple reaction monitoring (MRM) scan mode by reporting molecules that undergo a m/z 326/279 mass transition, which is consistent with the loss of the nitro group ([M-(HNO$_2$)]$^-$). Concurrent with MRM determination, enhanced product ion analysis (EPI) was performed to generate characteristic and identifying fragmentation patterns of eluting species with a precursor mass of m/z 326. EPI analysis utilizes the trap functionality of the triple quadrupole to "concentrate" fragment ions to enhance sensitivity. Zero grade air was used as source gas, and nitrogen was used in the collision chamber.

Red blood cell isolation and lipid extraction. Peripheral blood from fasting healthy human volunteers was collected by venipuncture into heparinized tubes (UAB Institutional Review Board-approved protocol #X040311001). Blood was centrifuged (1200×g; 10 min), the buffy coat removed and erythrocytes were isolated. Lipid extracts were prepared from red cells and plasma (21) and directly analyzed by mass spectrometry. Care was taken to avoid acidification during extraction to prevent artifactual lipid nitration due to the presence of endogenous nitrite (9). In experiments using urine as the biological specimen (UAB Institutional Review Board-approved protocol #X040311003), extraction conditions were identical.

Detection and quantitation of OA-NO$_2$ in human blood and urine. Quantitation of OA-NO$_2$ in biological samples was performed as described (9), with modifications. Matched blood and urine samples were obtained after >8 hr fasting; urine was collected from the first void of the day. During the monophase stage of the lipid extraction (21), [$^{13}$C]OA-NO$_2$ was added as internal standard to correct for losses due to extraction. Nitrated fatty acids were then analyzed by HPLC ESI MS/MS. Lipids were eluted from the HPLC column using an isocratic solvent system consisting of $CH_3CN:H_2O:NH_4OH$ (85:15:0.1, v/v), resulting in the co-elution of the two $OA-NO_2$ regioisomers. During quantitative analyses, two MRM transitions were monitored: m/z 326/279 ($OA-NO_2$) and m/z 344/297 ($[^{13}C]OA-NO_2$), transitions consistent with the loss of the nitro group from the respective precursor ions. The areas under each peak were integrated, the ratio of analyte to internal standard areas was determined and levels of $OA-NO_2$ were quantitated using Analyst 1.4 quantitation software (Applied Biosystems/MDS Sciex) by fitting the data to an internal standard curve. Data are expressed as mean±std dev (n=10; 5 female and 5 male).

Qualitative analysis of nitro- and nitrohydroxy-adducts of fatty acids. Using HPLC ESI-MS/MS, blood and urine samples were evaluated for the presence of allylic nitro derivatives other than $LNO_2$ and $OA-NO_2$. HPLC separations were performed similarly to those used to characterize $OA-NO_2$, with some modifications. Alternative MRM transitions were used to detect other potential nitroalkene derivatives. Based on what appears to be a common fragmentation product of nitrated fatty acids (i.e., loss of the nitro group; $[M-HNO_2]^-$), theoretical MRM transitions were determined for nitrated linolenic (18:3-$NO_2$), arachidonic (20:4-$NO_2$) and docosahexaenoic acids (22:6-$NO_2$). MRM transitions for nitrohydroxy adducts were also monitored: 18:1 (OH)—$NO_2$; 18:2(OH)—$NO_2$; 18:3(OH)—$NO_2$; 20:4(OH)—$NO_2$ and 22:6(OH)—$NO_2$.

$LNO_2$ and $OA-NO_2$ decay. The relative rates of $LNO_2$ and $OA-NO_2$ decay in aqueous solution were determined by incubating 3 µM $LNO_2$ and $OA-NO_2$ in phosphate buffer (100 mM, pH 7.4, 37° C.). During the two hour incubation, aliquots were removed and analyzed for $LNO_2$ and $OA-NO_2$ content. The aliquots were extracted as described (21) and 1 µM $[^{13}C]LNO_2$ was added during the monophase stage of the extraction procedure as an internal standard. Non-decayed $LNO_2$ and $OA-NO_2$ were quantitated via HPLC ESI-MS/MS as described above.

PPAR transient transfection assay. CV-1 cells from the ATCC (Manassas, Va.) were grown to ~85% confluence in DMEM/F12 supplemented with 10% FBS, 1% penicillin-streptomycin. Twelve hours before transfection, the media was removed and antibiotic-free media was applied. Cells were transiently co-transfected with a plasmid containing the luciferase gene under the control of three tandem PPAR response elements (PPRE) (PPREx3 TK-Luciferase) and PPARγ, PPARα or PPARδ expression plasmids, respectively. In all cases, fluorescence protein (GFP) expression plasmid was co-transfected as the control for transfection efficiency. Twenty-four hours after transfection, cells the returned to OptiMEM (Invitrogen, Carlsbad, Calif.) for 24 hr and then treated as indicated for another 24 hr. Reporter luciferase assay kits from Promega (Madison, Wis.) were used to measure the luciferase activity according to the manufacturer's instructions with a luminometer (Victor II, Perkin-Elmer). Luciferase activity was normalized by GFP units. Each condition was performed in triplicate in each experiment (n>3).

3T3-L1 differentiation and oil red O staining. 3T3-L1 preadipocytes were propagated and maintained in DMEM containing 10% FBS. To induce differentiation, 2-day post-confluent preadipocytes (designated day 0) were cultured in DMEM containing 10% FBS plus 1 and 3 µM $OA-NO_2$ for 14 days. The medium was changed every two days. Rosiglitazone (3 µM) and oleic acid (3 µM) were used as positive and negative controls, respectively. Differentiated adipocytes were stained with oil red O as previously (22).

$[^3H]$-2-Deoxy-D-glucose uptake assay in differentiated 3T3-L1 adipocytes. $[^3H]$-2-deoxy-D-glucose uptake was analyzed as previously (23). 3T3-L1 preadipocytes were grown in 24-well tissue culture plates, 2-day post-confluent monolayers were treated with 10 µg/ml insulin, 1 µM dexamethasone, and 0.5 mM 3-isobutyl-1-methylxanthine in DMEM containing 10% FBS for two days, then cells were maintained in 10 µg/ml insulin in DMEM containing 10% FBS for 6 days (medium was changed every three days). Eight days after induction of adipogenesis, test compounds in DMEM containing 10% FBS were added for an additional 2 days (medium was changed every day). The PPARγ-specific antagonist GW9662 was added 1 hr before other additions. After two rinses with serum-free DMEM, cells were incubated for 3 hr in serum-free DMEM and rinsed at room temperature three times with freshly prepared KRPH buffer (5 mM phosphate buffer, 20 mM HEPES, 1 mM $MgSO_4$, 1 mM $CaCl_2$, 136 mM NaCl, 4.7 mM KCl, pH 7.4). The buffer was replaced with 1 µCi/ml of $[^3H]$-2-deoxy-D-glucose in KRPH buffer for 10 min at room temperature. Cells were then rinsed three times with cold PBS, lysed overnight in 0.8 N NaOH (0.4 ml/well), neutralized with 26.6 µl of 12 N HCl and 360 µl of lysate was added into 4 ml Scinti-Safe Plus™ 50% for radioactivity determination by liquid scintillation counting.

Results

Figure 11:
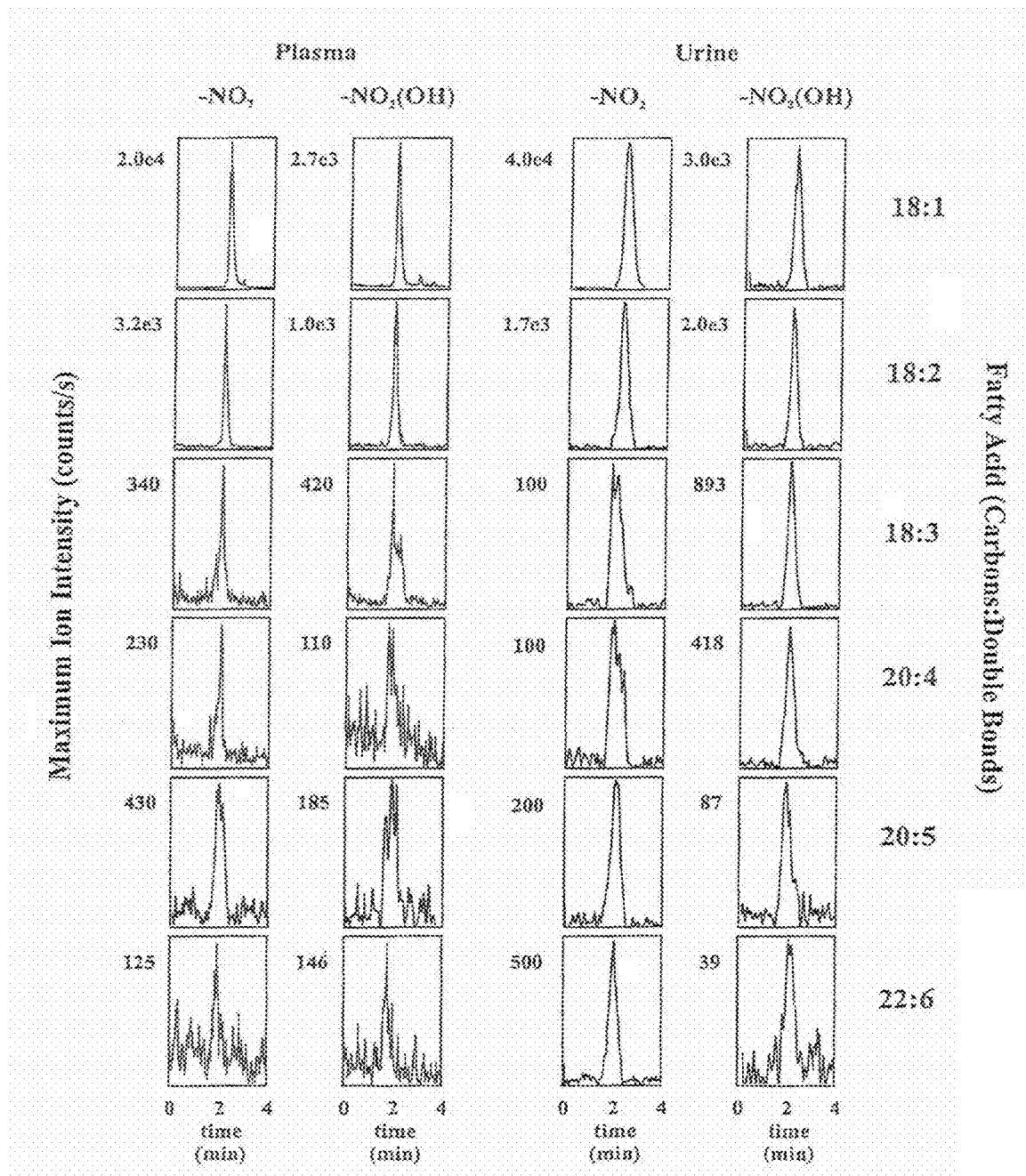
FIG. 11 shows nitrated fatty acid species in plasma and urine. Potential nitroalkene products were evaluated in plasma and urine. Fatty acids were extracted from clinical samples and analyzed by ESI-MS/MS as described in Methods. Nitrated fatty acid adducts (—$NO_2$) and their nitrohydroxy counterparts (L(OH)—$NO_2$) were detected using the multiple reaction monitoring (MRM) scan mode (Table 3) and are presented as base to peak HPLC elution profiles with maximum ion intensity given on the left axis. Six fatty acids were monitored: oleic acid (18:1), linoleic acid (18:2), linolenic acid (18:3), arachidonic acid (20:4) eicosapentaenoic acid (20:5) and docosahexaenoic acid (22:6). In plasma and urine, all of the nitrated fatty acids and their Michael addition products with $H_2O$ (nitrohydroxy adducts) appear in the HPLC elution profiles.

Detection and identification of nitrated PUFA. The discovery that $LNO_2$ is present in vivo motivated a search for additional endogenous nitrated fatty acids that may also act as lipid signaling molecules. To survey plasma and urine for other nitrated fatty acids, lipid extracts from healthy human blood donors were analyzed by HPLC ESI MS/MS in the multiple reaction monitoring (MRM) scan mode. MRM transitions were calculated for the nitro- and nitrohydroxy-adducts of six fatty acids, as shown in Table 2, and were used to detect nitro- and nitrohydroxy-adducts present in plasma and urine lipid extracts using an isocratic HPLC elution methodology (FIG. 11). Gradient elution methods using MRM and EPI scan modes were used for structural confirmation (not shown). Due to the lack of appropriate stable isotope internal standards for all derivatives, data are presented as base-peak spectra and are qualitative evidence that these species exist in vivo. Mass spectrometric analysis revealed that nitrated adducts of all monitored unsaturated fatty acids are present in blood and urine, which include the Michael-like addition products of these species with $H_2O$ detected as nitrohydroxy adducts. Owing to its predominant abundance and structural simplicity, oleic acid was synthesized as a standard to specifically quantitate endogenous $OA-NO_2$ content and signaling activity.

TABLE 2

Multiple reaction monitoring (MRM) transitions
for fatty acid nitroalkene derivatives
MRM values for nitroalkene and nitrohydroxy-adducts
of fatty acids were based on the common loss of the
nitro group that occurs during collision-induced
dissociation of nitrated fatty acids.

| Fatty Acid | Carbons:double bonds | Nitro adduct (—$NO_2$) | Nitrohydroxy adduct (L(OH)—$NO_2$) |
|---|---|---|---|
| Oleic | 18:1 | 326/279 | 344/297 |
| Linoleic | 18:2 | 324/277 | 342/295 |
| Linolenic | 18:3 | 322/275 | 340/293 |
| Arachidonic | 20:4 | 348/301 | 366/319 |

TABLE 2-continued

Multiple reaction monitoring (MRM) transitions
for fatty acid nitroalkene derivatives
MRM values for nitroalkene and nitrohydroxy-adducts
of fatty acids were based on the common loss of the
nitro group that occurs during collision-induced
dissociation of nitrated fatty acids.

| Fatty Acid | Carbons:double bonds | Nitro adduct ($-NO_2$) | Nitrohydroxy adduct (L(OH)—$NO_2$) |
|---|---|---|---|
| Eicosapentaenoic | 20:5 | 346/299 | 364/317 |
| Docosahexaenoic | 22:6 | 372/325 | 390/343 |

Synthesis and purification of OA-$NO_2$. Nitration of oleic acid by nitrosenylation will yield two potential regioisomers of OA-$NO_2$ (FIG. 10). Upon purification, analytical TLC, GC and LC-mass spectrometry of synthetic OA-$NO_2$ indicated no contamination by oleic acid nor oxidized products (not shown).

NMR analysis of OA-$NO_2$. The structure of synthetic OA-$NO_2$ (a 1:1 mixture of C9- and C10 regioisomers) was analyzed by $^1$H and $^{13}$C NMR. NMR splitting patterns are designated as s, singlet; d, doublet; t, triplet; q, quartet; m, multiplet and br, broad. $^1$H-NMR ($CDCl_3$): δ 11.1 (br s, 1H); 7.06 (dd, 1H, J=7.8 Hz); 3.75 (t, 2H, J=6.7 Hz); 2.55 (t, 2H, J=7.6 Hz); 2.36 (q, 2H, J=7.6 Hz); 2.33 (m, 2H); 2.20 (q, 2H, J=7.3 Hz); 1.85 (m, 2H); 1.61 (m, 4H); 1.47 (m, 4H); 1.32-1.25 (m, 8H); 0.87 (dt, 3H, J=7.0 Hz). The $^1$H spectrum and proposed assignments of diagnostic peaks are presented in FIG. 12A: 11.1 (COOH); 7.06 (C9 or C10, alkene proton, each a triplet from coupling to neighboring methylene —$CH_2$, with regioisomers superimposed on each other, appearing on one NMR spectrometer as a doublet of triplets and on the other as a quartet, which is really a superimposed pair of triplets); 3.75 (C8 or C11, allylic methylene neighboring nitro group; nitroalkene more electron-withdrawing than carbonyl); 2.55 (C2 methylene neighboring carbonyl); 2.20 (C8 or C11, allylic methylene); 1.85 (C7 or C12, methylene next to nitro-allyl position); 1.61 (C3 methylene); 0.87 (C18 terminal methyl, superimposed regioisomers resulting in doublet of triplets). There is no indication of oleic acid or synthetic intermediates and no trans-isomers of OA-$NO_2$ in the proton spectrum. The local environment of each proton in the 9- and 10-nitrated cis-isomers is not distinguishable, so each signal is indicative of relative positions in the alkene region, and absolute positions in the extreme portions of the molecule (i.e., the terminal methyl and acid groups). The aliphatic regions are too similar for exact assignments.

Further structural characterization was performed by $^{13}$C NMR. From the spectrum, 30 total peaks were observed: δ180.1, 180.0; 152.2, 152.0; 136.8, 136.4; 68.1; 34.2; 32.0; 29.6; 29.5; 29.5; 29.5; 29.4; 29.4; 29.3; 29.2; 29.1; 28.8; 28.7; 28.3; 28.2; 28.1; 28.1; 26.6; 26.6; 25.8; 24.8; 22.9; 14.3. The proposed assignment of diagnostic peaks is presented in FIG. 12B: 180.1, 180.0 (C1 carbonyl); 152.2, 152.0 (C9 or C10, alkene attached to $NO_2$); 136.7, 136.4 (C9 or C10, alkene); 68.2 (C8 or C11, $CH_2$ allylic to $NO_2$); 34.2 (C2, $CH_2$ neighboring carbonyl); 32.1 (C8 or C11, allylic distal to $NO_2$); 14.3 (C18, terminal $CH_3$). The total integrated signal is less than the total number of carbons for the two isomers (i.e., 30 vs. 36); thus, some peaks are identifiable doublets from isomers (e.g., carbonyl peaks), whereas others are indistinguishable and appear as a singlet (e.g., the methyl peak).

Figure 13:
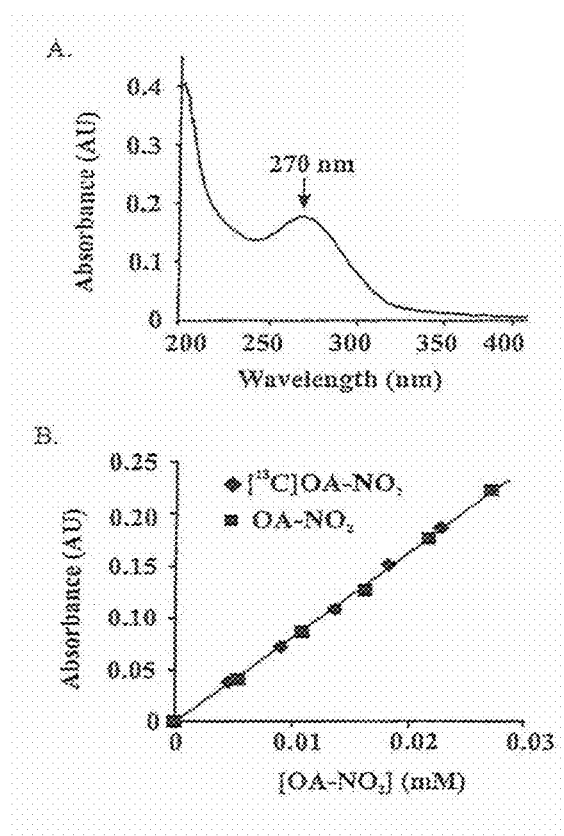
FIG. 13 shows the spectrophotometric analysis of OA-NO$_2$. (A) An absorbance spectrum of OA-NO$_2$ from 200-450 nm was generated using 23 μM OA-NO$_2$ in phosphate buffer (100 mM, pH 7.4) containing 100 μM DTPA. An absorbance maximum at 270 nm was identified. (B) Extinction coefficients for OA-NO$_2$ and [$^{13}$C]OA-NO$_2$ were determined by plotting absorbance ($\lambda_{270}$) vs. concentration, resulting in calculated values of ε=8.22 and 8.23 cm$^{-1}$ mM$^{-1}$, respectively.

Spectral characterization of OA-$NO_2$. The spectrum of OA-$NO_2$ was acquired in phosphate buffer in the presence of the iron chelator DTPA (FIG. 13A). An absorbance maximum at 270 nm was identified that is ascribed to electron absorption by the $NO_2$ group. Extinction coefficients for OA-$NO_2$ and [$^{13}$C]OA-$NO_2$ were determined by plotting absorbance ($\lambda_{270}$) vs. concentration, giving m=AU-$cm^1$ $mM^1$ and a calculated E=8.22 and 8.23 $cm^{-1}$ $mM^{-1}$, for OA-$NO_2$ and [$^{13}$C]OA-$NO_2$, respectively (FIG. 13B).

Figure 14:
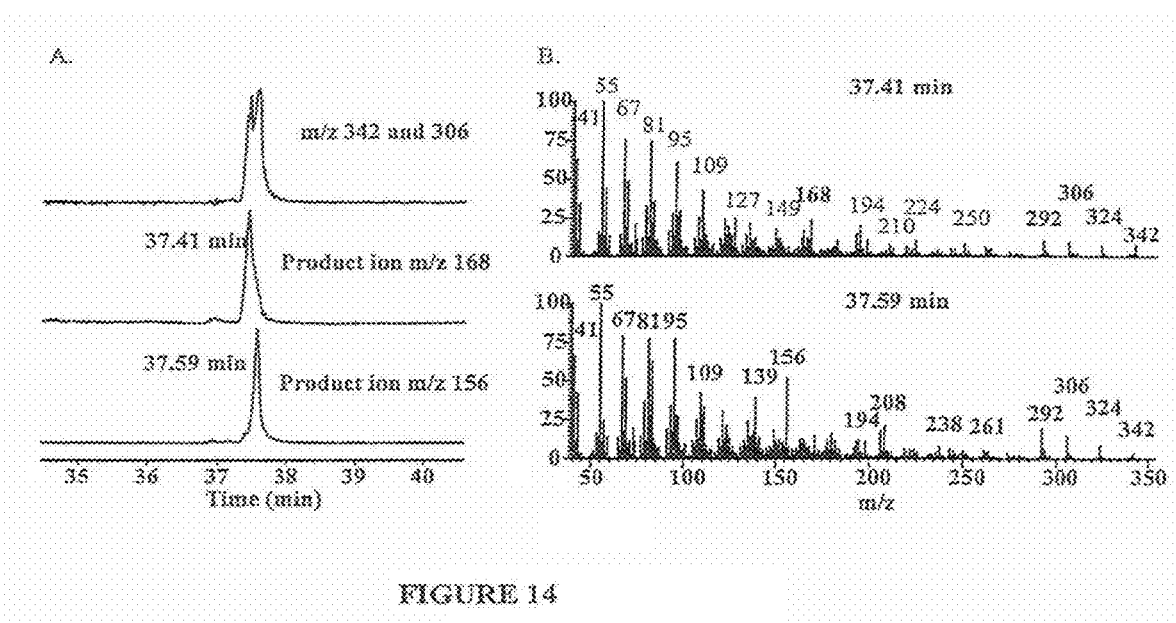
FIG. 14 shows the GC-MS analysis of synthetic OA-NO$_2$. (A) Methyl esters of the two synthetic OA-NO$_2$ regioisomers were generated as described in Methods and analyzed by EI GC MS/MS. The mixture was resolved using a 30 m fused silica column and detected by total ion monitoring. The upper chromatogram shows partial resolution of the two regioisomers. Product ion analysis of each peak (B) revealed that the first and second eluting peaks (37.41 and 37.59 min, respectively) each has a unique identifying ion: m/z 168 (peak 1) and m/z 156 (peak 2).

Characterization of OA-$NO_2$ by GC-MS/MS. Capillary columns used for gas chromatography have high resolving capacity and can separate regio- and diasteroisomers. Thus, initial mass spectrometric characterization of OA-$NO_2$ regioisomer methyl esters was performed by GC-MS (FIG. 14). Filtering total ion count (TIC) data to show ions with m/z 342 ([M+H]$^+$) and 306 (source fragment of m/z 342; [M−2$H_2O$]$^+$) reveals two peaks appearing at 37.4-37.7 min (FIG. 14A, upper panel). Product ion analysis of these peaks generated an identifying spectrum for each species (FIG. 14B). Ions with m/z 324 and 306 represent the loss of one and two $H_2O$ from the parent compound. The unique product ions m/z 168 and 156 for the first and second eluting peaks, respectively, were chosen as identifiers of each regioisomer. Filtering the MS/MS TIC for these product ions generated chromatograms that show the individual regioisomers of OA-$NO_2$ (FIG. 14A, middle and lower panels).

Figure 15:
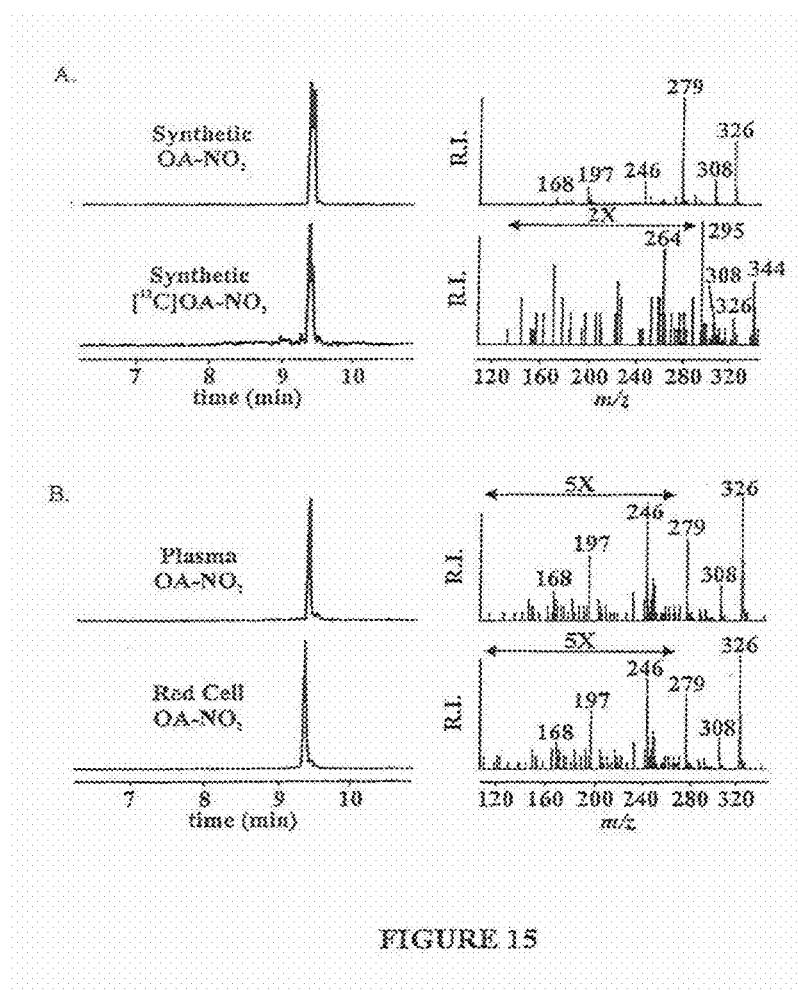
FIG. 15 shows the identification and characterization of synthetic and blood OA-NO$_2$ by HPLC ESI MS/MS. (A, left panels) OA-NO$_2$ and [$^{13}$C]OA-NO$_2$ were characterized by HPLC-ESI MS/MS. Nitrated oleic acid species were separated by HPLC and detected by acquiring MRM transitions consistent with the loss of the alkenyl nitro group [M–HNO$_2$]$^-$, m/z 326/279 and m/z 344/297 for OA-NO$_2$ and [$^{13}$C]OA-NO$_2$, respectively. (A, right panels) Concurrent to MRM detection, product ion analysis was performed to generate identifying fragmentation patterns also used to characterize in vivo OA-NO$_2$. The predominant product ions generated by collision-induced dissociation are identified in Table 3. (B) Total lipid extracts were prepared from packed red cell and plasma fractions of venous blood and directly analyzed by mass spectrometry.

Characterization and quantitation of OA-$NO_2$ by ESI-MS/MS. Using the gradient HPLC protocol described in Methods, synthetic OA-$NO_2$ regioisomers eluted from the reverse phase column as two overlapping peaks (FIG. 15). The HPLC elution profiles for synthetic OA-$NO_2$ and [$^{13}$C]OA-$NO_2$ were virtually identical (FIG. 15A, left panels). Concurrent product ion analysis of the overlapping peaks showed spectra consistent with OA-$NO_2$-derived species (FIG. 15A, right panels), with major fragments identified in Table 3. Using these same parameters and machine settings, lipid extracts of packed red cells and plasma were analyzed (FIG. 15B). The product ion spectra for OA-$NO_2$ of red cells and plasma are identical to those obtained from synthetic OA-$NO_2$, revealing that OA-$NO_2$ is endogenously present in blood. Interestingly, the HPLC elution profiles for plasma- and blood-derived OA-$NO_2$ show single peaks rather than overlapping species, suggesting only one regio-isomer is present in vivo.

TABLE 3

Collision-induced dissociation fragments of nitroalkene
fatty acid derivatives
Nitroalkene derivatives of fatty acids were analyzed by electrospray-
ionization tandem mass spectrometry. Product ion spectra from
synthetic standards were obtained in the negative ion mode as described
in Experimental Procedures. Major fragments generated for each standard
are listed below.

| Mass/charge (m/z) | OA-$NO_2$ | [$^{13}$C]OA-$NO_2$ | $LNO_2$ |
|---|---|---|---|
| 344 | — | [M-H] | — |
| 326 | [M-H] | [M-$H_2O$] | — |
| 324 | — | — | [M-$H_2O$] |
| 308 | [M-$H_2O$] | [M-2$H_2O$] | — |
| 306 | — | — | [M-$H_2O$] |
| 295 | — | [M-$HNO_2$] | — |
| 293 | — | — | [M-HNO] |
| 279 | [M-$HNO_2$] | — | — |
| 277 | — | — | [M-$HNO_2$] |
| 264 | — | [M-(2$H_2O$ + $CO_2$)] | — |
| 246 | [M-(2$H_2O$ + $CO_2$)] | — | — |
| 244 | — | — | [M-2$H_2O$ + $CO_2$)] |

To quantitate OA-NO$_2$ content in red cells and plasma, lipid extracts were separated using an isocratic HPLC elution protocol wherein analytes co-elute at 2 min; MRM transitions for OA-NO$_2$ and [$^{13}$C]OA-NO$_2$ were monitored (not shown). The concentration of OA-NO$_2$ in biological samples was determined from the ratio of analyte to internal standard peak areas using an internal standard curve that is linear over four orders of magnitude. The limit of quantitation (LOQ; determined as ten times the standard deviation of the noise) was calculated to be ~1.2 fmol on column (not shown). Blood samples obtained from ten healthy human volunteers (5 female, 5 male, ages ranging from 24 to 51) revealed free OA-NO$_2$ in red cells (i.e., OA-NO$_2$ not esterified to glycerophospholipids or neutral lipids) to be 59±11 pmol/ml packed cells (Table 4). Total free and esterified OA-NO$_2$, the amount present in saponified samples, was 214±76 pmol/ml packed cells. Thus, ~75% of OA-NO$_2$ in red cells exists as esterified fatty acids (9). In plasma, the free and esterified OA-NO$_2$ concentrations were 619±52 and 302±369 nM, respectively, and were observed to be more abundant than linoleic acid nitration products (9).

TABLE 4

Nitrated Oleic Acid in human blood a comparison with nitrated linoleic acid
Venous blood was obtained from healthy human volunteers and centrifuged, and plasma and red cells were extracted and prepared for mass spectrometric analysis as described in Experimental Procedures. During sample preparation, [$^{13}$C]OA-NO$_2$ was added as an internal standard to correct for losses. OA-NO$_2$ was quantitated by fitting analyte to internal standard area ratios obtained by MS to an internal standard curve. Concentration values for LNO$_2$ in the vascular compartment were obtained from ref. 9. Data are expressed as mean ± std dev (n-10;5 female and 5 male).

| Compartment | Fraction | [OA-NO$_2$] (nM) | [LNO$_2$] (nM) |
|---|---|---|---|
| Plasma | Free | 619 ± 52 | 79 ± 35 |
| | Esterified | 302 ± 369 | 550 ± 275 |
| | Total | 921 ± 421 | 630 ± 240 |
| Packed red cells | Free | 59 ± 11 | 50 ± 17 |
| | Esterified | 155 ± 65 | 199 ± 121 |
| | Total | 214 ± 76 | 249 ± 104 |
| Whole Blood* | Total | 639 ± 366* | 477 ± 128* |

*Assuming a 40% hematocrit

Figure 16:
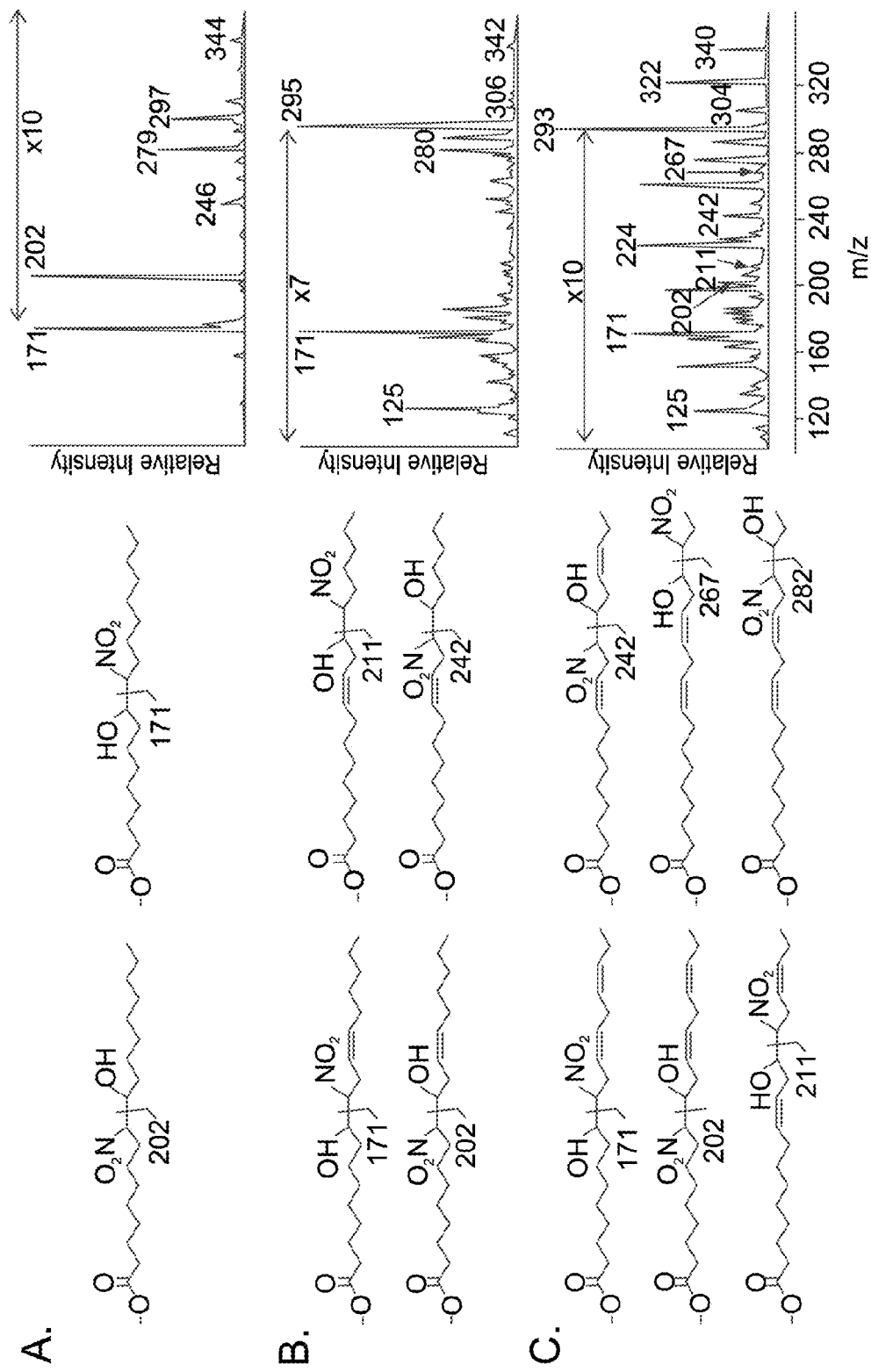
FIG. 16 shows the product ion analysis of fatty acid nitrohydroxy-adducts in urine. The presence of nitrohydroxy fatty acids in urine was confirmed by product ion analysis run concomitant to MRM detection. Structures of possible adducts are presented along with their diagnostic fragments and product ion spectra for (A) 18:1(OH)—NO$_2$, (B) 18:2 (OH)—NO$_2$ and (C) 18:3(OH)—NO$_2$. The 10-nitro regioisomer of 18:1(OH)—NO$_2$ is present in urine, as evidenced by the intense peak corresponding to m/z 171; also present are fragments consistent with the 9-nitro regioisomer (m/z 202), loss of a nitro group (m/z 297) and water (m/z 326). 18:2(OH)—NO$_2$ also shows a predominant m/z 171 fragment, again consistent with an oxidation product of LNO$_2$ nitrated at the 10-carbon (B). Diagnostic fragments for the three other potential regioisomers were not apparent. Finally, multiple regioisomers of 18:3(OH)—NO$_2$ are present (C).

Characterization of nitrohydroxy allylic derivatives. The initial survey to detect nitrated fatty acids indicated that nitrohydroxy allylic derivatives are also present in plasma and urine (FIG. 11). Their presence was confirmed by product ion analysis run concomitantly with MRM detection (FIG. 16). Structures of possible adducts are presented with diagnostic fragments and product ion spectra for 18:1 (OH)—NO$_2$, 18:2(OH)—NO$_2$ and 18:3(OH)—NO$_2$. Both the 9- and 10-nitro regioisomers of 18:1(OH)—NO$_2$ are present in urine (A) and plasma (not shown), as evidenced by the intense peaks corresponding to m/z 171 and 202 (A). Also present are fragments consistent with the loss of a nitro group and water (m/z 297 and 326, respectively). The product ion spectrum obtained from 18:2(OH)—NO$_2$ shows a predominant fragment (m/z 171), consistent with an oxidation product of LNO$_2$ nitrated at the 10-carbon (B). Diagnostic fragments for the three other potential regioisomers were not apparent. Finally, multiple regioisomers of 18:3(OH)—NO$_2$ are present (C). For all three Δ-9 fatty acids monitored, the predominant fragment generated during collision-induced dissociation (CID) is m/z 171.

Activation of PPARs by OA-NO$_2$. Recently, LNO$_2$ has been identified as an endogenous PPAR ligand (17). Considering the high levels of OA-NO$_2$ detected in vivo, OA-NO$_2$ was evaluated and compared with LNO$_2$ as a potential ligand for PPARα, PPARγ and PPARδ. CV-1 cells were transiently co-transfected with a plasmid containing the luciferase gene under regulation by three PPAR response elements (PPRE) in concert with PPARγ, PPARα or PPARδ expression plasmids. Dose-dependent activation by OA-NO$_2$ was observed for all PPARs, (FIG. 17A), with PPARγ showing the greatest response (significant activation at 100 nM); PPARα and PPARδ showed significant activation at ~300 nM OA-NO$_2$. Nitrated oleic acid was consistently more potent than LNO$_2$ in the activation of PPARγ, with 1 μM OA-NO$_2$ typically inducing the same degree of reporter gene expression as 3 μM LNO$_2$ or 1 μM Rosiglitazone; these increases were partially inhibited by the PPAR antagonist GW9662 (FIG. 17B). Native fatty acids did not activate PPARs at these concentrations (not shown). The greater potency of OA-NO$_2$ as a PPARγ agonist compared to LNO$_2$ motivated evaluation of the relative stability of these molecules, because LNO$_2$ decays in aqueous milieu to generate products that do not activate PPARs (17,24). Compared with LNO$_2$, OA-NO$_2$ is relatively stable, with only minimal decay occurring after 2 hr; a time when ~80% LNO$_2$ decay was noted (FIG. 17C).

The signaling actions of OA-NO$_2$ as a PPARγ ligand was assessed by evaluating its impact on adipocyte differentiation, as PPARγ-dependent gene expression plays an essential role in the development of adipose tissue (25,26). 3T3-L1 preadipocytes were treated with OA-NO$_2$ (1 μM), LNO$_2$ (3 μM) and negative controls for two weeks (FIG. 18A). Previously, LNO$_2$ was shown to induce pre-adipocyte differentiation to the same extent as Rosiglitazone (17). Adipocyte differentiation was assessed both morphologically and via oil red O staining, which revealed the accumulation of intracellular lipids. Vehicle, oleic acid and linoleic acid did not induce adipogenesis. In contrast, OA-NO$_2$ and LNO$_2$ induced >30% of 3T3-L1 preadiopcyte differentiation. Rosiglitazone, a synthetic PPARγ ligand, also induced PPARγ-dependent preadiopcyte differentiation. OA-NO$_2$- and Rosiglitazone-induced pre-adipocyte differentiation resulted in expression of specific adipocyte markers (PPARγ2 and aP2); oleic acid had no effect on these gene products (FIG. 18B). PPARγ ligands also play a central role in glucose uptake and metabolism, with agonists widely used as insulin-sensitizing drugs. Consistent with its potent PPARγ ligand activity, OA-NO$_2$ induced an increase in differentiated adipocyte glucose uptake (FIG. 19A). This effect of OA-NO$_2$ was paralleled by higher concentrations of LNO$_2$ (3 μM). The increased adipocyte glucose uptake, induced by nitrated fatty acids and the positive control Rosiglitazone, was partially inhibited by GW9662 (FIG. 19B). In aggregate, these observations reveal that OA-NO$_2$ manifests well-characterized PPARγ-dependent signaling actions.

Discussion

The nitration of hydrocarbons has long been recognized (27). Following the more recent discovery of vascular cell signaling actions of oxides of nitrogen (1,28), it is now also appreciated that •NO-derived species mediate oxidation, nitrosation, nitrosylation and nitration reactions of protein, DNA and unsaturated fatty acids (29). These reactions frequently yield stable products that influence target molecule structure and function to either a) translate the signaling actions of •NO or b) mediate pathogenic responses when occurring in "excess".

The reactions of •NO and its redox-derived products with lipids is multifaceted. Model studies of photochemical air pollutant-induced lipid oxidation revealed that exceedingly high concentrations of nitrogen dioxide (•$NO_2$) could induce nitration of fatty acids in phosphatidylcholine liposomes and fatty acid methyl ester preparations (30-32). Subsequently, reaction systems designed to model the interactions of endogenous •NO and •NO-derived species [e.g., peroxynitrite ($ONOO^-$) and nitrous acid ($HNO_2$)] with fatty acids showed that a) •NO mediates potent inhibition of autocatalytic radical chain propagation reactions of lipid peroxidation (33,34) and b) •NO-derived species produce both nitrated and oxidized derivatives of unsaturated fatty acids (3,35). One product of these reaction pathways, $LNO_2$, is present at ~500 nM concentration in healthy human red cells and plasma and serves as a ligand for the PPAR nuclear lipid receptor family (9,17). This insight, coupled with the fact that oleic acid is the most abundant unsaturated fatty acid in mammals and plants, motivated the present search for other potential endogenous nitrated fatty acid derivatives that might translate tissue redox signaling reactions.

Figure 12:
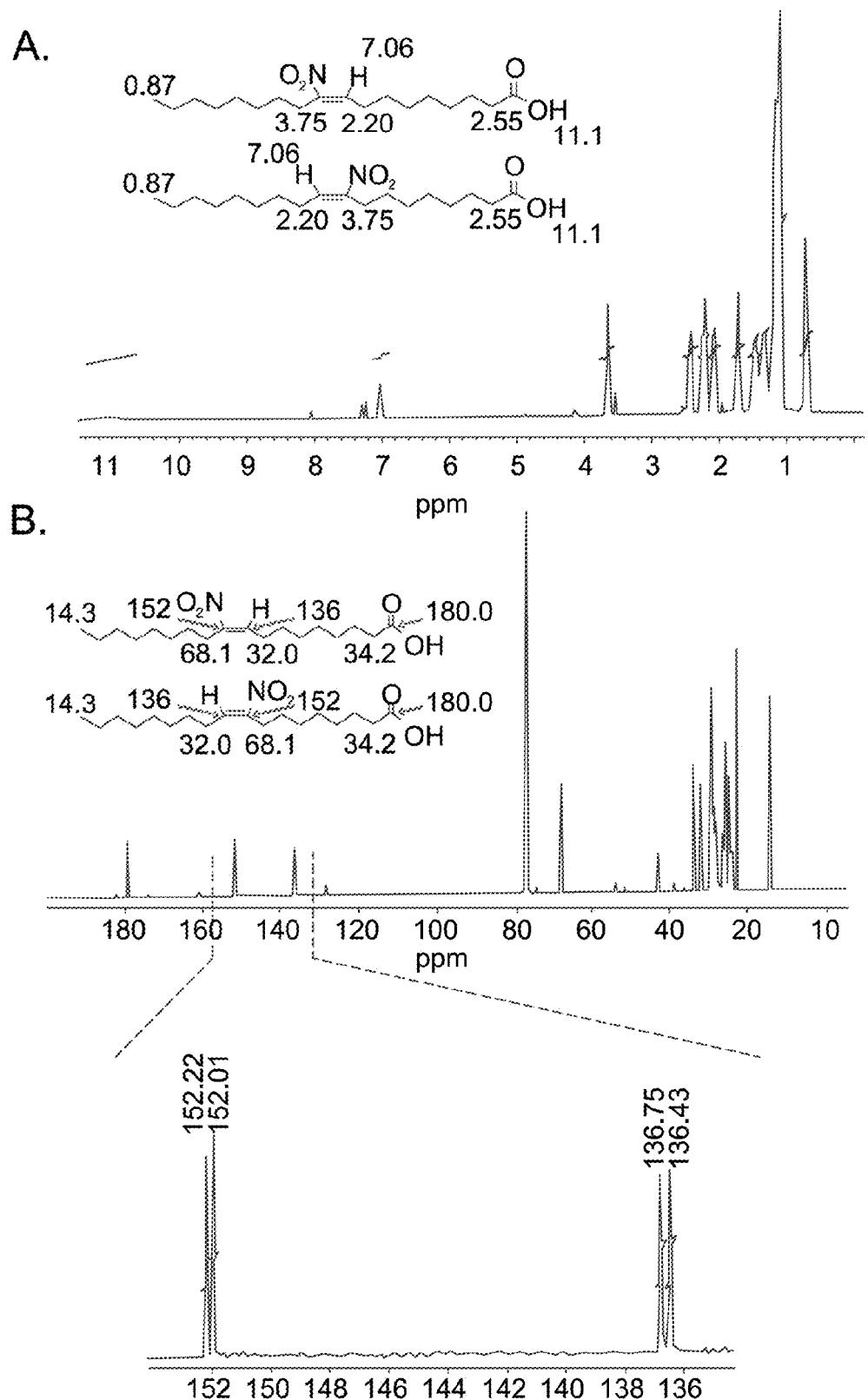
FIG. 12 shows $^1$H and $^{13}$C NMR spectrometry of synthetic nitro-oleate (OA-$NO_2$). Proton (A) and $^{13}$C (B) NMR spectroscopy confirmed the structure of synthetic OA-$NO_2$. Identified protons and carbons are indicated for each regioisomer; downfield shifts are presented in ppm. $^{13}$C NMR spectrometry indicates that synthetic OA-NO$_2$ is a mixture of two regioisomers, with most carbon peaks appearing as doublets. The equal height of the doublets suggests an equal molar ratio of the regioisomers. The peaks appearing at 152 ppm and 136 ppm are the carbons α and β to the alkenyl nitro group, respectively.

The structure of OA-$NO_2$ (FIG. 10) was defined on the basis of the synthetic rationale and NMR analysis (FIG. 12). Proton and $^{13}C$ NMR spectra indicate that the synthetic OA-$NO_2$ is comprised of two regioisomers, 9- and 10-nitro-9-cis-octadecenoic acids, with no trans-isomers apparent. Peaks characteristic of the nitro-allylic and allylic carbons in the $^{13}C$ spectrum both appear as doublets that are equal in intensity, indicating an equivalent distribution between regioisomers. EI GC MS confirmed the presence of 9- and 10-nitro-9-cis-octadecenoic acids by mass and differential retention times (FIG. 14). HPLC ESI MS/MS was used to further characterize synthetic OA-$NO_2$. The combined fragmentation pattern of OA-$NO_2$ regioisomers was obtained by CID, which provided a "molecular fingerprint" that was used to identify OA-$NO_2$ in biological samples (FIG. 15). ESI MS/MS analysis of lipid extracts derived from plasma and red cells yielded spectra with identical HPLC retention times and major product ions, confirming that OA-$NO_2$ exists endogenously; however, it is not possible from MS analysis to determine the cis/trans conformation of regioisomers. Quantitative analysis of plasma and red cells revealed that OA-$NO_2$ is present in the vasculature at net concentrations ~50% greater than $LNO_2$ (Table 4). Combined, esterified and free OA-$NO_2$ and $LNO_2$ are well above 1 µM, a concentration range capable of eliciting cell signaling responses.

The nitro functional groups of OA-$NO_2$ and $LNO_2$ are located on olefinic carbons. This configuration imparts a unique chemical reactivity that enables the release of •NO during aqueous decay of these nitroalkene derivatives via a modified Nef reaction (24). Furthermore, the α-carbon proximal to the alkenyl nitro group is strongly electrophilic, which readily reacts with $H_2O$ via a Michael addition mechanism to generate nitrohydroxy adducts (FIGS. 11 and 16). Nitrohydroxy-arachidonic acid species have previously been detected in bovine cardiac muscle (36), and nitrohydroxy-linoleic acid has been identified in lipid extracts obtained from hypercholesterolemic and post-prandial human plasma, suggesting that this is a ubiquitous derivative (37). The present identification of a wide spectrum of nitrated fatty acids and corresponding nitrohydroxy-fatty acid derivatives in human plasma and urine reveals that nitration reactions occur with all unsaturated fatty acids (FIGS. 11, and 16). The hydroxyl moiety of nitrohydroxy-fatty acids destabilizes the adjacent carbon-carbon bond, resulting in heterolytic scission reactions that a) generate predictable fragments during CID (FIG. 16) and b) render potentially unique cell signaling actions to fatty acid nitrohydroxy derivatives. Present data indicates, however, that nitrohydroxy adducts of $LNO_2$ and OA-$NO_2$ are not avid ligands for PPARγ (FIG. 17C).

Multiple mechanisms can support the basal and inflammatory nitration of fatty acids by •NO-derived species, including •$NO_2$-initiated auto-oxidation of polyunsaturated fatty acids via hydrogen abstraction from the bis-allylic carbon and nitration by acidified $NO_2^-$ (31,38-42). Of relevance to both basal and inflammatory cell signaling, •$NO_2$ can be derived from multiple reactions. This includes the homolytic scission of both peroxynitrous acid (ONOOH) and nitrosoperoxocarbonate ($ONOOCO_2^-$), as well as the oxidation of $NO_2^-$ by heme peroxidases (43,44). Present data supports that all of these alkenyl nitration mechanisms can yield nitrated fatty acids that are structurally similar or identical to the OA-$NO_2$ and $LNO_2$ detected clinically. Nitration by a free radical mechanism might suggest that all olefinic carbons within a fatty acid would be susceptible nitration targets; with the additional likelihood of double bond rearrangement and conjugation. The discovery of OA-$NO_2$ lends critical perspective to this issue, because monounsaturated fatty acids are less susceptible to free radical-mediated hydrogen abstraction reactions. In view of the data presented herein, alternative fatty acid nitration mechanisms may thus also be viable. For example, nitration by an ionic addition reaction (e.g., nitronium ion, $NO_2^+$) can generate singly nitrated fatty acids with no double bond-rearrangement. Since $NO_2^+$ readily reacts with $H_2O$, this species may require stabilization in the hydrophobic milieu of the membrane bilayer or localized catalysis (e.g., reaction of ONOO— with transition metals) to serve as a biologically-relevant nitrating species. Finally, radical addition reactions may also occur with mono- and polyunsaturated fatty acids to yield non-conjugated nitroalkene derivatives of polyunsaturated fatty acids, as revealed by studies of acidified $NO_2^-$ and •$NO_2$-mediated fatty acid methyl ester oxidation and nitration profiles (32,41).

Of important relevance to mechanisms underlying fatty acid nitration in vivo, the nitrohydroxy adducts of Δ9 unsaturated fatty acids examined in the present study (18:1, 18:2 and 18:3) all have a predominant fragment of m/z 171 (FIG. 16). This mass is consistent with 9-oxo-nonanoic acid, a fragment generated with authentic standards when the nitro group is located at the 10-carbon and the hydroxy moiety at the 9-carbon (data not shown). This suggests either strict steric control or enzymatic mechanisms regulating the stereospecificity of biological fatty acid nitration. The nitration of Δ9 unsaturated fatty acids to C10 nitroalkene derivatives, with retention of double bond arrangement, supports that stereospecific enzymatic reactions may mediate fatty acid nitration. It is also possible that nitrated fatty acids are made bioavailable from dietary sources that give rise to specific fatty acid nitroalkene derivatives.

Figure 17:
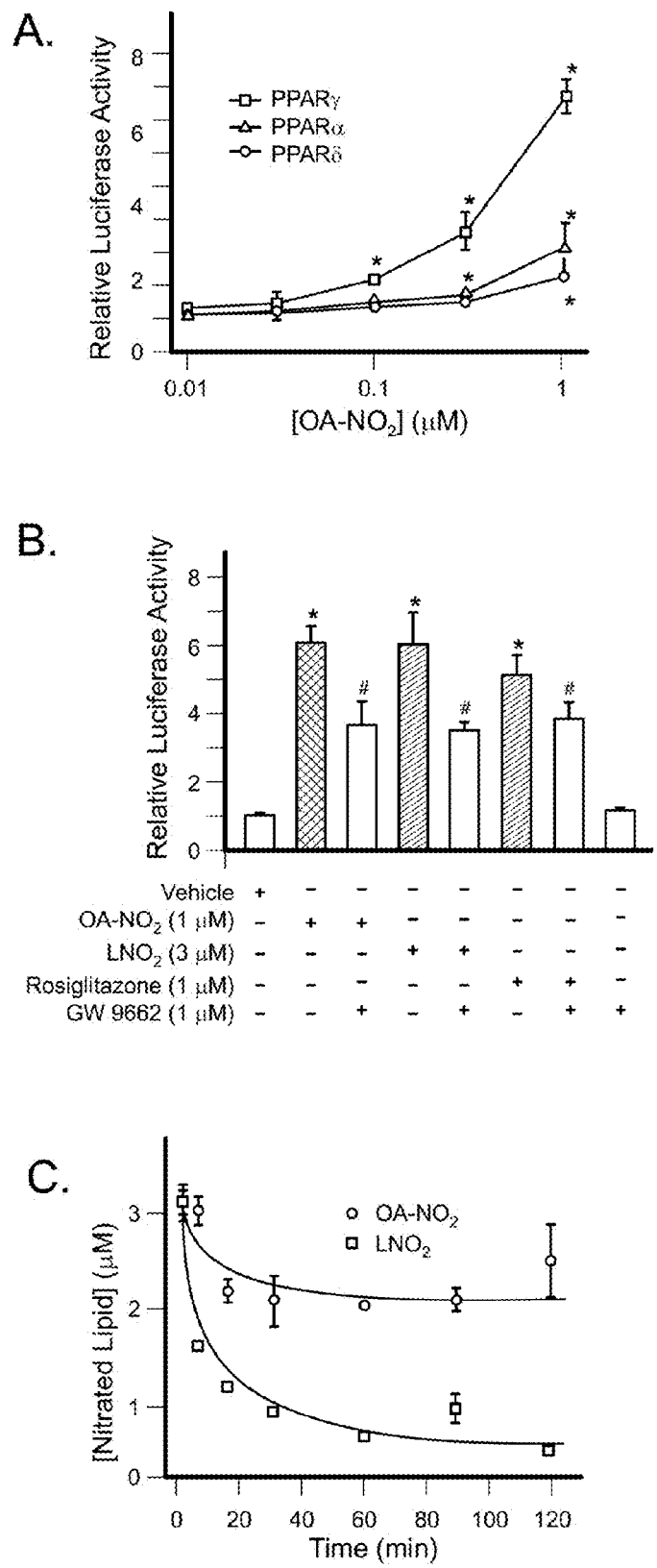
FIG. 17 shows that OA-NO$_2$ is a PPARγ agonist. (A) CV-1 cells transiently co-transfected with a plasmid containing the luciferase gene under the control of three tandem PPRE (PPRE×3 TK-Luciferase) and hPPARγ, hPPARα or hPPARβ expression plasmids showed all three PPARs were activated by OA-NO$_2$, with the relative activation of PPARγ>PPARδ>PPARα. All values are expressed as mean±SD (n=3). PPARγ activation was significantly different from vehicle at 100 nM OA-NO$_2$, whereas PPARα and PPARδ activation were significantly different from vehicle at 300 nM and 1 μM OA-NO$_2$, respectively (P≤0.05; Student's t test). (B) Nitrated oleic acid appears to be more potent than LNO$_2$ in the activation of PPARγ, with 1 μM OA-NO$_2$ inducing similar activity as 3 μM LNO$_2$ versus control (P<0.05; Student's t test). Activation of PPARγ was partially yet significantly blocked using the PPARγ antagonist GW9662 (P≤0.05; Student's t test). (C) Equimolar concentrations of OA-NO$_2$ and LNO$_2$ (3 μM) were incubated in 100 mM phosphate buffer. After 2 hr, only 25% of the initial OA-NO$_2$ had degraded; ~80% of LNO$_2$ degrades in the same time period, indicating a great aqueous stability of OA-NO$_2$. All values are expressed as mean±SD (n>3).
Figure 18:
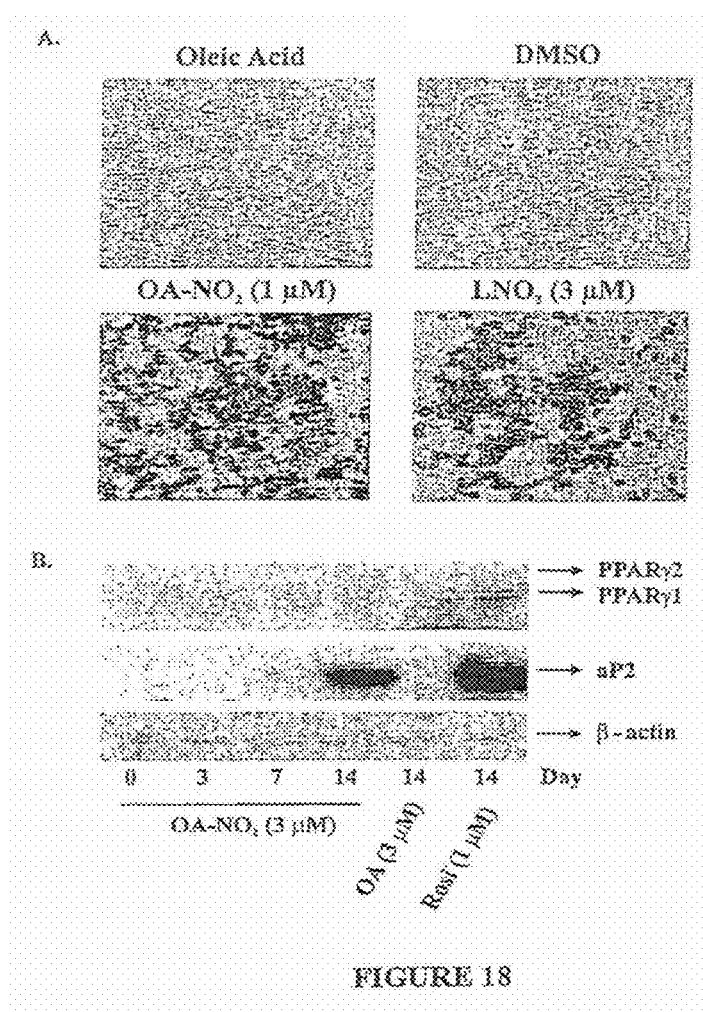
FIG. 18 shows that OA-NO$_2$ induces adipogenesis in 3T3 L1 preadipocytes. PPARγ plays an essential role in the differentiation of adipocytes. 3T3-L1 preadipocytes were treated with OA-NO$_2$, LNO$_2$, Rosiglitazone and controls (oleic acid, linoleic acid and DMSO) for two weeks. (A) Adipocyte differentiation was assessed both morphologically and via oil red O staining, which reveals the accumulation of intracellular lipids. Vehicle, oleic acid and linoleic acid did not induce adipogenesis, while OA-NO$_2$ induced ~60% of 3T3-L1 preadiopcyte differentiation; LNO$_2$ induced ~30%, reflecting the greater potency of OA-NO$_2$. As the positive control, Rosiglitazone also induced PPARγ-dependent adipogenesis. (B) OA-NO$_2$ and Rosiglitazone-induced preadipocyte differentiation resulted in the expression of adipocyte-specific markers (PPARγ2 and aP2), an event not detected for oleic acid.
Figure 19:
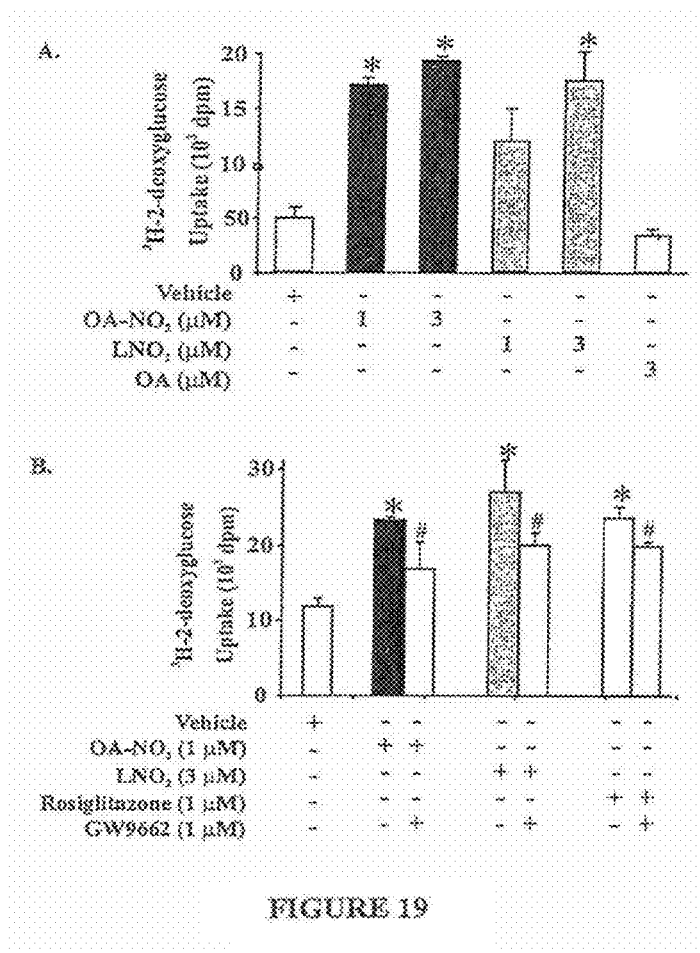
FIG. 19 shows that OA-NO$_2$ induces [$^3$H]-2-deoxy-D-glucose uptake in differentiated 3T3 L1 adipocytes. (A) PPARγ ligands induce glucose uptake in adipose tissue. To further define the functional significance of OA-NO$_2$ as a PPARγ ligand, 3T3-L1 preadipocytes were differentiated to adipocytes and treated with OA-NO$_2$ or LNO$_2$ for two days prior to addition of [$^3$H]-2-deoxy-D-glucose. OA-NO$_2$ induced significant increases in glucose uptake; these effects were paralleled by LNO$_2$ (P≤0.05; Student's t test). (B) The increases in glucose uptake induced by nitrated lipids and the positive control Rosiglitazone were significantly inhibited by the PPARγ-specific antagonist GW9662 (P<0.05; Student's t test). All values are expressed as mean±SD (n=3).

Designation of nitroalkene derivatives as a class of signaling molecules is contingent upon ascribing specific bioactivities to multiple members within the class at clinically-relevant concentrations. Nitrolinoleate has been observed to inhibit neutrophil and platelet function via cGMP-independent, cAMP-mediated mechanisms (10-12). Also, aqueous decay of $LNO_2$ yields •NO, a reaction that is facilitated by translocation of $LNO_2$ from a hydrophilic to hydrophobic microenvironment, which in turn induces cGMP-dependent vessel relaxation (12,24). Recently, $LNO_2$ has also been reported to serve as a robust ligand for PPAR (17), a nuclear hormone receptor that binds lipophilic ligands to induce DNA binding of the transcription factor complex at DR1-type motifs in the promoter sites of target genes. Downstream effects of PPARγ activation include modulation of metabolic and cellular differentiation genes and regulation of inflammatory responses, adipogenesis and glucose homeostasis (45,46). In the vasculature, PPARγ is expressed in monocytes, macrophages, smooth muscle cells and endothelium (47) and plays a central role in regulating the expression of genes related to lipid trafficking, cell proliferation and inflammatory signaling. Herein we show that $OA-NO_2$ also serves as a PPARγ, α and δ ligand that rivals or exceeds the potency of $LNO_2$ and synthetic PPAR ligands such as fibrates and thiazolidinediones (FIGS. 17-19). The increased potency of $OA-NO_2$ as a PPARγ ligand is either due to increased aqueous stability relative to $LNO_2$ (FIG. 17C) or increased receptor affinity. The combined blood concentrations of $OA-NO_2$ and $LNO_2$ in healthy humans exceeds 1 μM (Table 4), concentrations well-within the range needed to activate PPAR receptors and exceeding those of previously-proposed endogenous PPARγ ligands. These observations have broad implications for the •NO and redox signaling reactions that play a crucial role in dysregulated cell growth and differentiation, metabolic syndrome, atherosclerosis and diabetes-all clinical pathologies that also include a significant contribution from PPAR-regulated cell signaling mechanisms (48).

The regulation of inflammation by inhibiting eicosanoid synthesis is a well-established and prevalent target of anti-inflammatory drug strategies. Much less well-understood are the concerted cell signaling mechanisms by which inflammation is favorably resolved in vivo. While the integrated in vivo tissue signaling activities of nitrated fatty acids remain to be defined, studies to date indicate that these pluripotent signaling mediators generally manifest salutary metabolic and anti-inflammatory actions (10-12,17). The capability of redox-derived lipid signaling molecules to mediate the resolution of inflammation is a relatively new concept, with lipoxins representing one new class of lipid mediators that may also act in this manner (49). Endogenous concentrations of $OA-NO_2$ and $LNO_2$ are abundant and are increased by oxidative inflammatory reactions. Thus, nitrated fatty acids are expected to play both receptor-dependent (via PPAR ligand activity) and cyclic nucleotide-mediated roles in transducing the redox signaling actions of oxygen and •NO, thereby regulating organ function, cell differentiation, cell metabolism and systemic inflammatory responses.

Throughout Example 3, several publications have been referenced. These publications are listed in the Reference List for Example 3. The disclosures of these publications in their entireties are hereby incorporated by reference into this application in order to more fully describe the compounds, compositions and methods described herein.

REFERENCE LIST FOR EXAMPLE 3

Reference List

1. Smith, W. L. (1992) *Am. J Physiol* 263, F181-F191
2. Montuschi, P., Barnes, P. J., and Roberts, L. J. (2004) *FASEB J* 18, 1791-1800
3. Rubbo, H., Radi, R., Trujillo, M., Telleri, R., Kalyanaraman, B., Barnes, S., Kirk, M., and Freeman, B. A. (1994) *J. Biol. Chem.* 269, 26066-26075
4. Schopfer, F. J., Baker, P. R., and Freeman, B. A. (2003) *Trends Biochem. Sci.* 28, 646-654
5. Marshall, H. E., Merchant, K., and Stamler, J. S. (2000) *FASEB J* 14, 1889-1900
6. Vidwans, A. S., Uliasz, T. F., Hewett, J. A., and Hewett, S. J. (2001) *Biochemistry* 40, 11533-11542
7. Larfars, G., Lantoine, F., Devynck, M. A., Palmblad, J., and Gyllenhammar, H. (1999) *Blood* 93, 1399-405
8. Rubbo, H., Radi, R., Anselmi, D., Kirk, M., Barnes, S., Butler, J., Eiserich, J. P., and Freeman, B. A. (2000) *J.Biol.Chem.* 275, 10812-10818
9. Baker, P. R., Schopfer, F. J., Sweeney, S., and Freeman, B. A. (2004) *Proc•Natl.Acad.Sci. U.S.A* 101, 11577-11582
10. Coles, B., Bloodsworth, A., Eiserich, J. P., Coffey, M. J., McLoughlin, R. M., Giddings, J. C., Lewis, M. J., Haslam, R. J., Freeman, B. A., and O'Donnell, V. B. (2002) *J.Biol.Chem.* 277, 5832-5840
11. Coles, B., Bloodsworth, A., Clark, S. R., Lewis, M. J., Cross, A. R., Freeman, B. A., and O'Donnell, V. B. (2002) *Circ.Res.* 91, 375-381
12. Lim, D. G., Sweeney, S., Bloodsworth, A., White, C. R., Chumley, P. H., Krishna, N. R., Schopfer, F., O'Donnell, V. B., Eiserich, J. P., and Freeman, B. A. (2002) *Proc•Natl.Acad.Sci. U.S.A* 99, 15941-15946
13. Gladwin, M. T., Shelhamer, J. H., Schechter, A. N., Pease-Fye, M. E., Waclawiw, M. A., Panza, J. A., Ognibene, F. P., and Cannon, R. O., III (2000) *Proc•Natl.Acad.Sci. U.S.A* 97, 11482-11487
14. Rassaf, T., Bryan, N. S., Kelm, M., and Feelisch, M. (2002) *Free Radic.Biol.Med.* 33, 1590-1596
15. Rassaf, T., Bryan, N. S., Maloney, R. E., Specian, V., Kelm, M., Kalyanaraman, B., Rodriguez, J., and Feelisch, M. (2003) *Nat.Med.* 9, 481-482
16. Cosby, K., Partovi, K. S., Crawford, J. H., Patel, R. P., Reiter, C. D., Martyr, S., Yang, B. K., Waclawiw, M. A., Zalos, G., Xu, X., Huang, K. T., Shields, H., Kim-Shapiro, D. B., Schechter, A. N., Cannon, R. O., III, and Gladwin, M. T. (2003) *Nat.Med.* 9, 1498-1505
17. Schopfer, F. J., Lin, Y., Baker, P. R., Cui, T., Garcia-Barrio, M., Zhang, J., Chen, K., Chen, Y. E., and Freeman, B. A. (2005) *Proc NatlAcadSci USA* 102, 2340-2345
18. Lee, C. H. and Evans, R. M. (2002) *Trends Endocrinol..Metab* 13, 331-335
19. Marx, N., Duez, H., Fruchart, J. C., and Staels, B. (2004) *Circ.Res.* 94, 1168-1178
20. Dodge, J. T. and Phillips, G. B. (1967) *JLipidRes.* 8, 667-675
21. Bligh, E. G. and Dyer, W. L. (1959) *Can.J.Biochem.Physiol.* 37, 911-917
22. Zhang, J., Fu, M., Cui, T., Xiong, C., Xu, K., Zhong, W., Xiao, Y., Floyd, D., Liang, J., Li, E., Song, Q., and Chen, Y. E. (2004) *Proc•Natl.Acad.Sci. U.S.A* 101, 10703-10708
23. Mukherjee, R., Hoener, P. A., Jow, L., Bilakovics, J., Klausing, K., Mais, D. E., Faulkner, A., Croston, G. E., and Paterniti, J. R., Jr. (2000) *Mol.Endocrinol.* 14, 1425-1433
24. Schopfer, F. J., Baker, P. R., Giles, G., Chumley, P., Batthyany, C., Crawford, J., Patel, R. P., Hogg, N., Branchaud, B. P., Lancaster, J. R., Jr., and Freeman, B. A. (2005) *J Biol Chem*
25. Evans, R. M., Barish, G. D., and Wang, Y. X. (2004) *Nat.Med.* 10, 355-361
26. Zhang, J., Fu, M., Cui, T., Xiong, C., Xu, K., Zhong, W., Xiao, Y., Floyd, D., Liang, J., Li, E., Song, Q., and Chen, Y. E. (2004)*Proc Natl Acad Sci USA* 101, 10703-10708

27. Zelinsky, N. D. and Rosanoff, M. A. (1912) *Z.Physikal Chem.* 78, 629-633
28. Ignarro, L. J., Byrns, R. E., Buga, G. M., Wood, K. S., and Chaudhuri, G. (1988) *J Pharmacol.Exp.Ther.* 244, 181-189
29. Miranda, K. M., Espey, M. G., Jourd'heuil, D., Grisham, M. B., Fukoto, J. M., Feelisch, M., and Wink, D. A. (2000) The Chemical Biology of Nitric Oxide. In Ignarro, L. J., editor. *Nitric Oxide: Biology and Pathobiology*, Academic Press, San Diego
30. Finlayson-Pitts, B. J., Sweetman, L. L., and Weissbart, B. (1987) *Toxicol.Appl.Pharmacol.* 89, 438-448
31. Gallon, A. A. and Pryor, W. A. (1993) *Lipids* 28, 125-133
32. d'Ischia, M., Rega, N., and Barone, V. (1999) *Tetrahedron* 55, 9297-9308
33. O'Donnell, V. B., Chumley, P. H., Hogg, N., Bloodsworth, A., Darley-Usmar, V. M., and Freeman, B. A. (1997) *Biochemistry* 36, 15216-15223
34. Hogg, N., Kalyanaraman, B., Joseph, J., Struck, A., and Parthasarathy, S. (1993) *FEBS Lett.* 334, 170-174
35. Rubbo, H., Parthasarathy, S., Barnes, S., Kirk, M., Kalyanaraman, B., and Freeman, B. A. (1995) *Arch.Biochem.Biophys.* 324, 15-25
36. Balazy, M., Iesaki, T., Park, J. L., Jiang, H., Kaminski, P. M., and Wolin, M. S. (2001) *J.Pharmacol.Exp.Ther.* 299, 611-619
37. Lima, E. S., Di Mascio, P., Rubbo, H., and Abdalla, D. S. (2002) *Biochemistry* 41, 10717-10722
38. Baldus, S., Castro, L., Eiserich, J. P., and Freeman, B. A. (2001) *Am.J.Respir.Crit Care Med.* 163, 308-310
39. Gallon, A. A. and Pryor, W. A. (1994) *Lipids* 29, 171-176
40. Napolitano, A., Camera, E., Picardo, M., and d'Ischia, M. (2000) *J.Org.Chem.* 65, 4853-4860
41. Napolitano, A., Crescenzi, O., Camera, E., Giudicianni, I., Picardo, M., and d'Ischia, M. (2004) *Tetrahedron* 58, 5061-5067
42. O'Donnell, V. B., Eiserich, J. P., Chumley, P. H., Jablonsky, M. J., Krishna, N. R., Kirk, M., Barnes, S., Darley-Usmar, V. M., and Freeman, B. A. (1999) *Chem.Res.Toxicol.* 12, 83-92
43. Beckman, J. S., Beckman, T. W., Chen, J., Marshall, P. A., and Freeman, B. A. (1990) *Proc•Natl.Acad.Sci. U.S.A* 87, 1620-1624
44. Castro, L., Eiserich, J. P., Sweeney, S., Radi, R., and Freeman, B. A. (2004) *Arch.Biochem.Biophys.* 421, 99-107
45. Lee, C. H. and Evans, R. M. (2002) *Trends Endocrinol.Metab* 13, 331-335
46. Marx, N., Duez, H., Fruchart, J. C., and Staels, B. (2004) *Circ.Res.* 94, 1168-1178
47. Wang, N., Verna, L., Chen, N. G., Chen, J., Li, H., Forman, B. M., and Stemerman, M. B. (2002) *J.Biol.Chem.* 277, 34176-34181
48. Li, A. C., Binder, C. J., Gutierrez, A., Brown, K. K., Plotkin, C. R., Pattison, J. W., Valledor, A. F., Davis, R. A., Willson, T. M., Witztum, J. L., Palinski, W., and Glass, C. K. (2004) *J Clin.Invest* 114, 1564-1576
49. Levy, B. D., Clish, C. B., Schmidt, B., Gronert, K., and Serhan, C. N. (2001) *Nat.Immunol.* 2, 612-619

Example 4

The aqueous decay and concomitant release of nitric oxide (•NO) by nitrolinoleic acid (10-nitro-9,12-octadecadienoic acid and 12-nitro-9,12-octadecadienoic acid; $LNO_2$) is reported. Mass spectrometric analysis of reaction products support the Nef reaction as the mechanism accounting for the generation of •NO by the aqueous reactions of fatty acid nitroalkene derivatives. Nitrolinoleic acid is stabilized by aprotic milieu, with $LNO_2$ decay and •NO release strongly inhibited by phosphatidylcholine-cholesterol liposome membranes and detergents when present at levels above their critical micellar concentrations. The release of •NO from $LNO_2$ was induced by the UV photolysis and $I_3^-$-based ozone chemiluminescence reactions currently being used to quantify putative protein nitrosothiol (RSNO) and N-nitrosamine derivatives. This reactivity of $LNO_2$ complicates the qualitative and quantitative analysis of biological oxides of nitrogen when applying UV photolysis and triiodide ($I_3^-$)-based analytical systems in biological preparations typically abundant in nitrated fatty acids. These results reveal that nitroalkene derivatives of linoleic acid are pluripotent signaling mediators that act via not only receptor-dependent mechanisms, but also by transducing the signaling actions of •NO via pathways subject to regulation by the relative distribution of $LNO_2$ to hydrophobic versus aqueous microenvironments.

Nitrolinoleic acid (10-nitro-9,12-octadecadienoic acid and 12-nitro-9,12-octadecadienoic acid; abbreviated as $LNO_2$) is present in plasma lipoproteins and red blood cell membranes at concentrations of ~500 nM, rendering this species the most quantitatively abundant biologically-active oxide of nitrogen in the human vascular compartment (1). Nitrolinoleic acid is a product of nitric oxide (•NO)-dependent linoleic acid nitration reactions that predominantly occur at the C10 and C12 alkene carbons. The positional isomer distribution of the $LNO_2$ alkenyl nitro group indicates that in vivo fatty acid nitration is a consequence of nucleophilic (nitronium group, $NO_2^+$) and/or radical (nitrogen dioxide, •$NO_2$) addition reactions with olefinic carbons.

Recent observations reveal that $LNO_2$ is a pluripotent signaling mediator that acts via both receptor-dependent and -independent pathways. Nitrated fatty acids are specific and high affinity endogenous ligands for peroxisome proliferator-activated receptors (2), and serve to activate receptor-dependent gene expression at physiological concentrations. $LNO_2$ also activates cAMP-dependent protein kinase signaling pathways in neutrophils and platelets, serving to down-regulate the activation of these inflammatory cells (3,4). Finally, $LNO_2$ induces vessel relaxation in an endothelial-independent manner (5). This $LNO_2$-mediated relaxation of phenylephrine-preconstricted aortic rings was 1) a consequence of $LNO_2$-induced stimulation of smooth muscle cell and aortic segment cGMP content, 2) inhibitable by the •NO scavenger oxyhemoglobin and 3) ODQ-inhibitable (e.g., guanylate cyclase-dependent). Although these vessel responses to $LNO_2$ suggest •NO as the mediator of guanylate cyclase activation, the identity of the proximal $LNO_2$-derived, cGMP-dependent signaling molecule was not directly identified (5).

Nitric oxide, synthesized by three different nitric oxide synthase isoforms, was first shown to mediate endothelial-dependent relaxation via reaction with the heme iron of guanylate cyclase and subsequent activation of cGMP-dependent protein kinases (6). Subsequent to this discovery, there has been a growing appreciation that the cell signaling actions of •NO are also transduced by secondary products derived from redox reactions of •NO. These redox reactions yield a variety of oxides of nitrogen displaying both unique and overlapping reactivities that can regulate differentiated cell function via both cGMP- and non-cGMP-dependent mechanisms. These products include nitrite ($NO_2^-$), •$NO_2$, peroxynitrite ($ONOO^-$), nitrosothiols (RSNO) and dinitrogen trioxide ($N_2O_3$). These reactive species serve to transduce the cell signaling actions of •NO by inducing changes in target molecule structure and function via oxidation, nitration or nitrosation reactions (7,8).

The lipophilicity and intrinsic chemical reactivities of •NO facilitate multiple interactions with lipids that impact both cellular redox and •NO signaling reactions. For example, •NO concentrates in membranes and lipoproteins, where it more readily reacts with oxygen to yield oxidizing, nitrosating and nitrating species such as $N_2O_3$ and $N_2O_4$ (9-11). In these lipophilic compartments, •NO can react with lipid peroxyl radicals (LOO.) at diffusion-limited rates, readily out-competing tocopherols and ascorbate for the scavenging of intermediates that would otherwise propagate lipid oxidation. In this regard, •NO displays an oxidant-protective, anti-inflammatory role (12,13). Of relevance to inflammatory signaling, heme and non-heme-containing peroxidases and oxygenases that catalyze physiologic and pathologic fatty acid oxygenation reactions also catalytically consume •NO during enzyme turnover [e.g., lipoxygenases (14,15), cyclooxygenase (16) and myeloperoxidase (17)]. The reaction of •NO with these enzymatic catalysts and free radical intermediates of fatty acid oxygenation in turn inhibits rates of fatty acid oxygenation product formation. The convergence of •NO and fatty acid oxygenation reactions thus can influence the steady state concentration of both •NO and eicosanoids in a concerted fashion.

Redox reactions of •NO frequently induce the chemical modification of target molecules, including the nitrosylation (addition of •NO) of heme proteins (18), the nitrosation (addition of the nitroso group NO) of thiol substituents (7) and the nitration (addition of the nitro group $NO_2$) of protein tyrosine residues and DNA bases (8). Herein, the present invention shows that $LNO_2$, a product of •NO-dependent unsaturated fatty acid nitration reactions that is abundant in red cells and plasma, decays in aqueous milieu to release •NO. This generation of •NO by $LNO_2$ is inhibited by aprotic environments, a milieu that concomitantly stabilizes $LNO_2$. Moreover, it is shown that UV photolysis and $I_3^-$-based chemiluminescence approaches currently used to quantify •NO derived from protein heme-nitrosyl, RSNO and N-nitrosamine (RNNO) derivatives, also facilitate •NO release from $LNO_2$. This complicates the interpretation of quantitative and qualitative results from the application of these analytical systems in biological preparations. In aggregate, these results reveal that nitroalkene derivatives of fatty acids serve to transduce the signaling actions of •NO via pathways subject to regulation by the relative distribution of $LNO_2$ to hydrophobic versus aqueous microenvironments.

Materials—Horse heart myoglobin, octyl-P3-glucopyranoside (OG) and octyl-thio-β-glucopyranoside (OTG), carboxy 2-phenyl-4,4,5,5-tetramethylimidazoline-1-oxyl-3-oxide (cPTIO), diethylenetriarninepentaacetate (DTPA), $Na_2HPO_4$ and sodium dithionite were from Sigma (St Louis, Mo.). $LNO_2$ and $[^{13}C]LNO_2$ were synthesized and purified as previously described (1). Metmyoglobin was reduced using sodium dithionite, desalted by exclusion chromatography on a Sephadex PD-10 column and further oxygenated by equilibration with 100% oxygen.

Electron paramagnetic resonance—EPR measurements were performed at room temperature using a Bruker Elexsys E-500 spectrometer equipped with an ER049X microwave bridge and an AquaX liquid sample cell. The following instrument setting were used: modulation frequency, 100 kHz; modulation amplitude, 0.05 G; receiver gain, 60 dB; time constant, 1.28 ms; sweep time, 5.24 s; center field, 3510 G; sweep width, 100 G; power, 20 mW; scan parameter, 16 scans.

Spectrophotometry—The UV spectrum of $LNO_2$ and repetitive scans of $LNO_2$ decay kinetics were collected using a Hitachi UV 2401 PC spectrophotometer. Apparent •NO formation was calculated from extents of oxymyoglobin oxidation in the visible wavelength range (spectrum) and at 580 nm (kinetic mode). Initial oxymyoglobin oxidation was calculated using a UV probe Version 1.10 ($\epsilon_{580}$ 14.4 $mM^{-1}$ $cm^{-1}$). Decomposition of the $NO_2$ group was followed at 268 nm and the appearance of oxidized products at 320 nm.

Liposome preparation—Reverse phase evaporation liposomes were formed from dipalmitoylphosphatidylcholine (DPPC), cholesterol and stearylamine (4:2:1 mole ratio) following an established procedure (19). Briefly DPPC, cholesterol and stearylamine were dissolved in $CHCl_3$ and sonicated with 10 mM KPi buffer ($CHCl_3$/KPi, 2:1, v/v). The organic solvent was then removed by evaporation under reduced pressure at 45° C. The liposomes were allowed to anneal for 12 h at room temperature then centrifuged and the pellet resuspended in the experimental buffer.

Chemiluminescence and UV photolysis analyses—For direct detection of •NO release, $LNO_2$ (75 μM) was incubated directly or with different additions (sulfanilamide, 1.5% w/v in 2 M HCl, 5 min, 25° C., with or without $HgCl_2$, 50 mM) under aerobic conditions in a capped vial for 3 min. The gas phase was then injected into a chemiluminescence detector (ANTEK Instruments, Houston, Tex.). Additionally, known concentrations of DEA-NONOate (in 10 mM NaOH) were added to a capped vial containing 0.5 M HCl. NOx concentration profiles of plasma samples were performed by •NO chemiluminescence analysis. Measurement of putative $NO_2^-$, RSNO, and other •NO derivatives present in plasma was performed by using an $I_3^-$-based reducing system as previously (20,21). Rats were treated by intraperitoneal injection of 50 mg/kg E. coli LPS and 5 hr later blood was collected in EDTA anticoagulation tubes following cardiac puncture. Following removal of red cells by centrifugation (500 g×10 min), plasma samples were pretreated with either sulfanilamide (final concentration 1.5% w/v in 2 M HCl, 5 min, 25° C.) with or without $HgCl_2$ (50 mM) prior to injecting into the chemiluminescence detector to measure $NO_2^-$ and $HgCl_2$-resistant $NO_x$ derivatives, respectively. For UV photolysis studies, a water-cooled reaction chamber was filled with 1 ml of phosphate buffer (50 mM, pH 7.4 containing 10 μM DTPA) and continuously bubbled with argon. The chamber was illuminated using an ILC PS300-1A xenon arc source (ILC Technology, Sunnyvale, Calif.). Samples were injected into the reaction chamber through an air-tight septum and released •NO was passed to the reaction chamber of a Sievers NOA 280 NO analyzer and detected by chemiluminescence after reaction with ozone ($O_3$).

Mass spectrometric analysis—$LNO_2$ was extracted using the method of Bligh and Dyer (22). During extraction, $[^{13}C]LNO_2$ was added as internal standard and the $LNO_2$ content of samples quantified using LC/MS/MS (1). Qualitative and quantitative analysis of $LNO_2$ by ESI MS/MS was performed using a hybrid triple quadrupole-linear ion trap mass spectrometer (4000 Q trap, Applied Biosystems/MDS Sciex) as described (1). For the detection and characterization of $L(OH)NO_2$, the hydration product of $LNO_2$ generated by a Michael-like addition between $H_2O$ and the nitroalkene, $LNO_2$ (3 μM) was incubated at 25° C. for 60 min in 100 mM phosphate buffer containing 100 μM DTPA pH 7.4 and extracted (Bligh and Dyer). $L(OH)NO_2$ was detected using a multiple reaction monitoring (MRM) scan mode by reporting molecules that undergo an m/z 342/295 mass transition. This method selects (m/z 342) in the first quadrupole, consistent with the precursor ion, and following collision-induced dissociation (CID) yields in Q3 a species (m/z 295) consistent with loss of the nitro group ([M-(HNO$_2$)]$^-$). Presence of the nitrohydroxy-adduct was confirmed by product ion analysis of m/z 342. The degradation of LNO$_2$ to secondary products was followed in negative ion mode after chloroform extraction and direct injection into an ion trap mass spectrometer with electrospray ionization (LCQ Deca, ThermoFinnigan).

Figure 20:
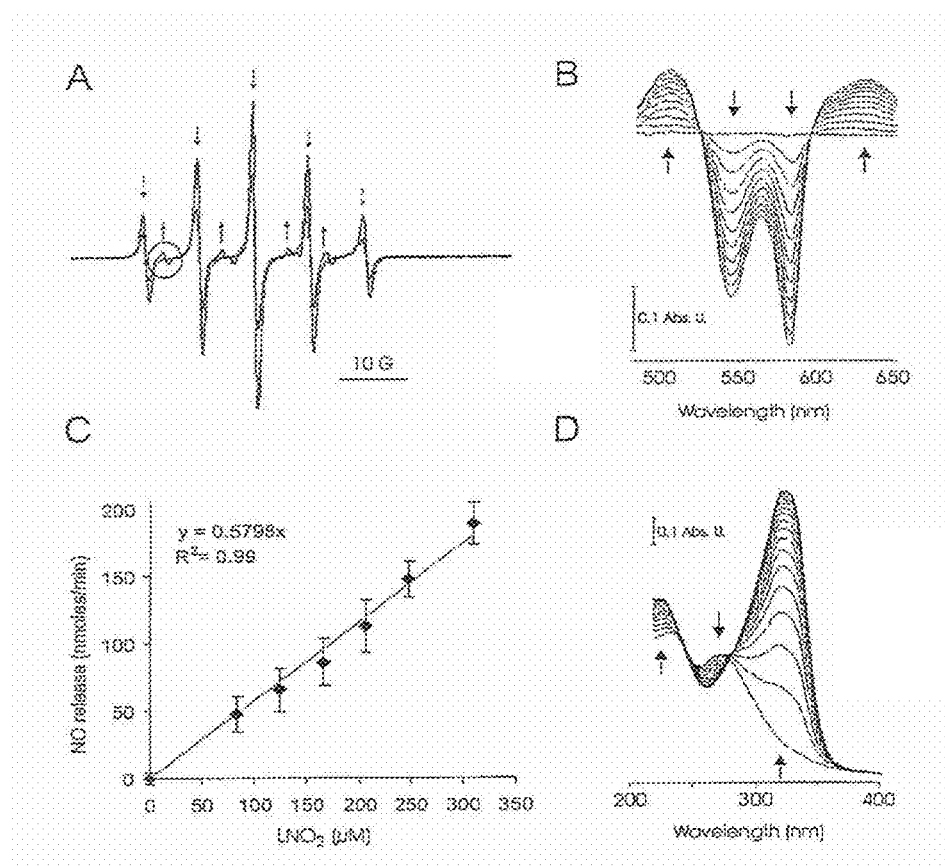
FIG. 20 shows EPR and UV/visible spectroscopic detection of •NO release by LNO$_2$. (A) EPR spectral analysis of cPTIO (200 μM, red line) reduction to cPTI (black line) by LNO$_2$ (300 μM) decay during a 60 min decay period. (B) Differential spectra of oxymyoglobin (20 μM) oxidation by LNO$_2$ (200 μM). Spectra were repetitively recorded at 5 min intervals and show the decrease in the 580 nm and 543 nm maxima (characteristic of the α and β visible band absorbance of the oxymyoglobin) and the increase in 630 and 503 nm maxima characteristic of metmyoglobin. (C) •NO release rate detected by oxymyoglobin (20 μM) oxidation in the presence of different concentrations of LNO$_2$. Values expressed as mean±SD of 2 independent experiments repeated four times. (D) UV spectra of LNO$_2$ taken every 10 min, revealing loss of the characteristic absorbance of the NO$_2$ group at 268 nm and the formation of a new chromophore at 320 nm. (A, B and D) Spectra are representative of 3 independent experiments.

Characterization of •NO release from LNO$_2$—cPTIO is a selective spin trap for •NO (k=10$^4$ M$^{-1}$s$^{-1}$, (23)), with the product of this reaction, cPTI, displaying a characteristic EPR spectrum. In order to determine if •NO is derived from LNO$_2$, it was incubated at 25° C. for different times in 100 mM phosphate buffer containing 100 μM DTPA, pH 7.4 in the presence of cPTIO. This resulted in a time-dependent decrease of the characteristic five peak cPTIO signal and the appearance of a new signal ascribed to cPTI (FIG. 20A). This release of •NO by LNO$_2$ was concentration-dependent and followed first order decay kinetics for LNO$_2$. Due to limitations of the •NO-cPTIO reaction for quantitating yields of NO, oxymyoglobin was utilized to measure •NO release rates (24).

LNO$_2$ was incubated with oxymyoglobin in 100 mM phosphate buffer containing 100 μM DTPA, pH 7.4 and •NO-dependent oxymyoglobin oxidation was followed spectrophotometrically. LNO$_2$ oxidized oxymyoglobin in a dose- and time-dependent fashion, yielding metmyoglobin as indicated by the spectral changes depicted in FIG. 20B. The apparent rate constant for •NO release by LNO$_2$, calculated from the oxidation of oxymyoglobin to metmyoglobin, was k=9.67×10$^{-6}$ s$^{-1}$ (FIG. 20C). To monitor the concomitant decomposition of the parent LNO$_2$ molecule, its UV spectrum was first analyzed. LNO$_2$ displays a characteristic absorbance spectrum with a peak at 268 nm, ascribed to the π electrons of the NO$_2$ group. During aqueous LNO$_2$ decay, this maximum decreases and a new maximum appears at 320 nm, corresponding to a mixture of oxygen and conjugated diene-containing products not yet fully characterized by mass spectroscopy (FIG. 20D). The decrease in absorbance at 268 nm paralleled •NO release, as detected by both EPR and oxymyoglobin oxidation.

Figure 21:
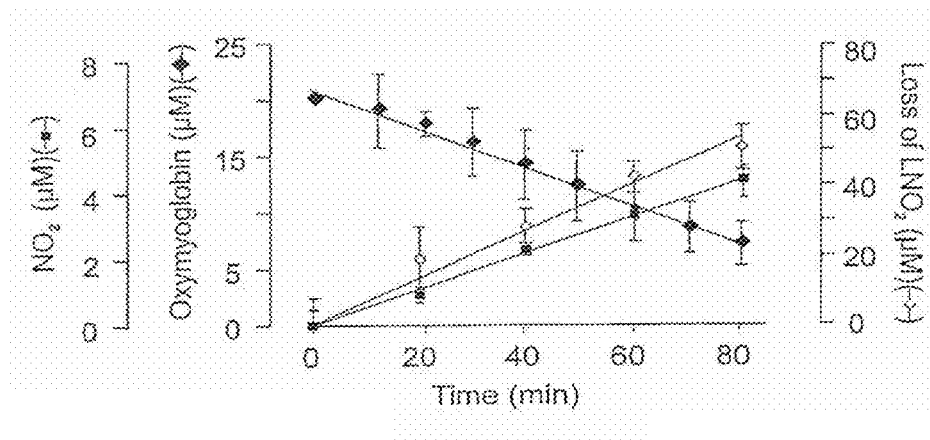
FIG. 21 shows nitrite formation during LNO$_2$ decay. The time-dependent formation of NO$_2^-$ during LNO$_2$ (initial concentration 200 μM) decomposition was measured in parallel with oxymyoglobin (20 μM) oxidation. Nitrite formation was measured in the absence of oxymyoglobin. Values expressed as mean±SD of 3 independent experiments repeated three times.

Nitrite formation during LNO$_2$ decomposition—During LNO$_2$-dependent •NO formation, measured via oxymyoglobin oxidation and MS analysis of LNO$_2$ parent molecule loss in aqueous buffers, the stable •NO oxidation product NO$_2$ accumulates with time (FIG. 21). The release of •NO from LNO$_2$ was maximal at pH 7.4 (22), suggesting a role for protonation and deprotonation reactions in •NO formation from LNO$_2$.

Figure 23:
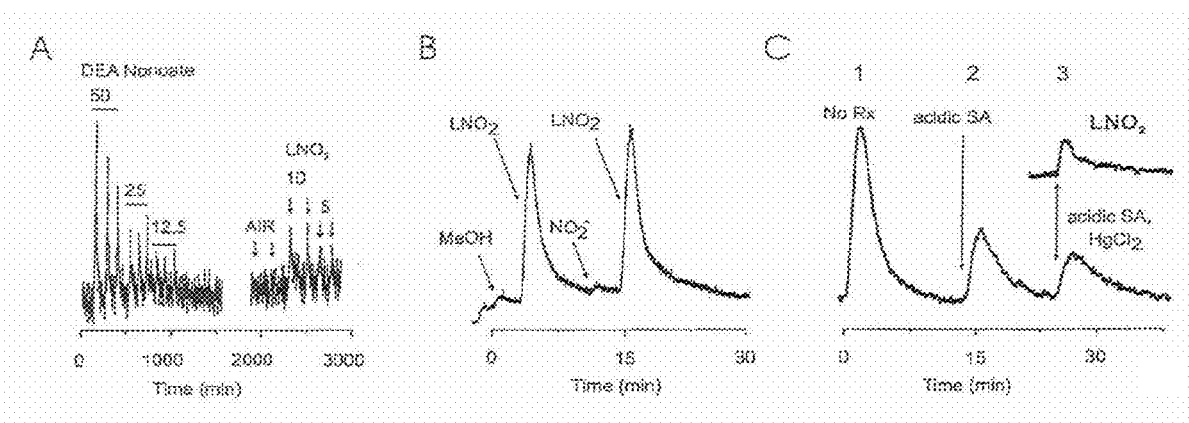
FIG. 23 shows chemiluminescent detection of •NO release by $LNO_2$. A) $LNO_2$ (5 and 10 mM) was incubated in a capped vial under aerobic conditions for 3 min and the gas phase injected into an $O_3$ chemiluminescence detector. Additionally, known concentrations of DEA-NONOate (nM) (in 10 mM NaOH) were added to a capped vial containing 0.5 M HCl and the gas phase was injected into the chemiluminescence detector. B) Phosphate buffer (50 mM phosphate pH 7.4 containing 10 μM DTPA) was illuminated with a xenon arc lamp. •NO formation was examined by $O_3$-based chemiluminescence after the injection of MeOH (20 μl), $LNO_2$ (4 nmol in 20 μl MeOH, two additions made before and after sodium nitrite addition) and sodium nitrite (4 nmol in 20 μl phosphate buffer). C) Blood was obtained by cardiac puncture of LPS-treated rats, red cells removed by centrifugation and plasma samples treated as noted in Experimental Procedures. The following conditions were studied in panel C: (1) $I_3^-$ alone; (2) $I_3^-$ plus sulfanilamide; (3) $I_3^-$ plus sulfanilamide and $HgCl_2$, with 3.5 nmol $LNO_2$ treated with $I_3^-$ plus sulfanilamide and $HgCl_2$, as for the corresponding plasma sample. Derived •NO was measured by •NO chemiluminescence analysis. Traces are representative from three different experiments.

Chemiluminescence analysis of LNO$_2$-derived •NO— Gas phase O$_3$-mediated chemiluminescence detection of NO is a highly sensitive and specific method for detecting •NO. LNO$_2$ was incubated in capped vials in 100 mM phosphate buffer, 100 μM DTPA, pH 7.4 in air and the gas phase directly injected into the detector. The •NO-dependent chemiluminescence yield was a function of concentration of DEA-NONOate and LNO$_2$ concentrations, studied separately (FIG. 23A). Chemiluminescence was also time-dependent, increasing with time of LNO$_2$ decay prior to gas sampling from vials.

UV photolysis has been used to quantitate RSNO derivatives of proteins and other NO-containing biomolecules (25,26). When LNO$_2$ (4 nmol) was subjected to UV photolysis in concert with •NO chemiluminescence detection, UV light exposure stimulated •NO release from LNO$_2$ (FIG. 23B). The •NO chemiluminescence response to NO$_2$ (4 nmol) added to samples being subjected to UV photolysis and repetitive LNO$_2$ addition was also examined to address the possibility that LNO$_2$-derived NO$_2^-$ formed during decay reactions might have accounted for some fraction of net chemiluminescent yield; it did not.

Appreciating that nitroalkene derivatives of red cell membrane and plasma fatty acids are present in human blood, whether LNO$_2$-derived •NO has the potential to interfere with the chemiluminescent detection of NO$_2^-$, RSNO, RNNO or NO-heme compounds in plasma, when also analyzed via a triiodide (I$_3^-$)-based reaction system (21) was examined. Plasma from LPS-treated rats was used to exemplify this reaction system, since LPS treatment of rodents induces a robust elevation in plasma biomolecule NO-adduct levels (27). First, plasma was directly injected into the detector chamber and I$_3^-$ reagent added, yielding a signal indicative of net plasma NO$_2^-$, RSNO, RNNO and NO-heme compounds (FIG. 23C, peak 1). Then, plasma treated with acidic sulfanilamide (which removes NO$_2^-$) was injected, giving a peak of lower intensity after I$_3^-$ reagent addition, indicative of RSNO and putative RNNO derivatives (20,28). Finally, a plasma sample treated with acidic sulfanilamide and HgCl$_2$ was injected, which resulted in an even smaller peak following I$_3^-$ reagent addition (FIG. 23C, peak 3). This latter peak has been referred to as Hg-resistant RNNO derivatives (20,28). Using this strategy and combination of reagents, LNO$_2$ pretreated with acidic sulfanilamide and HgCl$_2$ also generated •NO chemiluminescence for extended periods of time following I$_3^-$ addition (FIG. 23C, LNO$_2$ inset).

Figure 24:
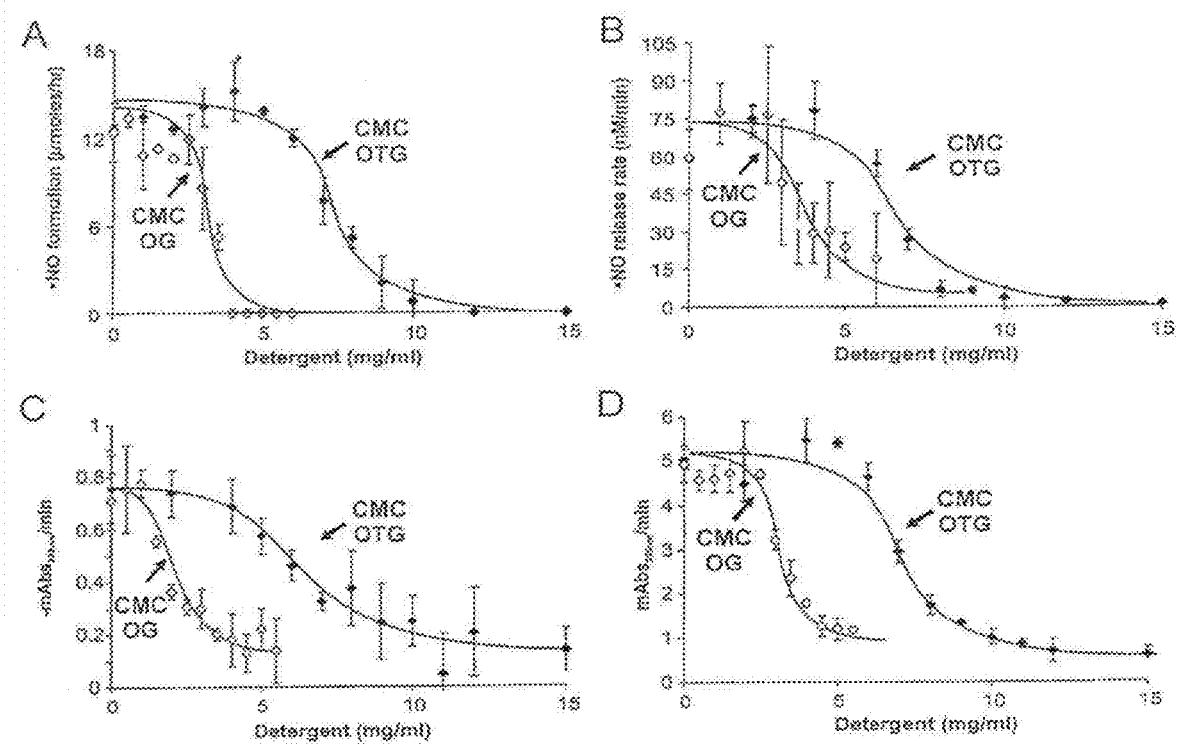
FIG. 24 shows spectroscopic (EPR, UV and visible) analysis of micellar inhibition of $LNO_2$ decomposition and •NO release. In panels A-D, closed diamonds represent conditions containing OTG and open diamonds represent OG. A) •NO release from $LNO_2$ (80 μM) in the presence of different OTG and OG concentrations after 60 min, as measured by EPR detection of cPTIO (80 μM) conversion to cPTI. The extent of cPTIO (80 μM) conversion to cPTI by known concentrations of proli-NONOate was utilized to calculate yields of •NO. B) •NO release rate from $LNO_2$ (130 μM) in the presence of different concentrations of OG and OTG, as measured by oxidation of oxymyoglobin (20 μM) to metmyoglobin. An extinction coefficient of 14.4 $mM^{-1} cm^{-1}$ was used to calculate yields of •NO. C) Initial decomposition rates of $LNO_2$ (37 μM), measured at 268 nm, in the presence of different concentrations of OTG and OG. D) Same as C, but rates of $LNO_2$ decomposition product formation at 320 nm were measured. Values are expressed as mean±SD of at least 3 independent experiments repeated three or four times.
Figure 25:
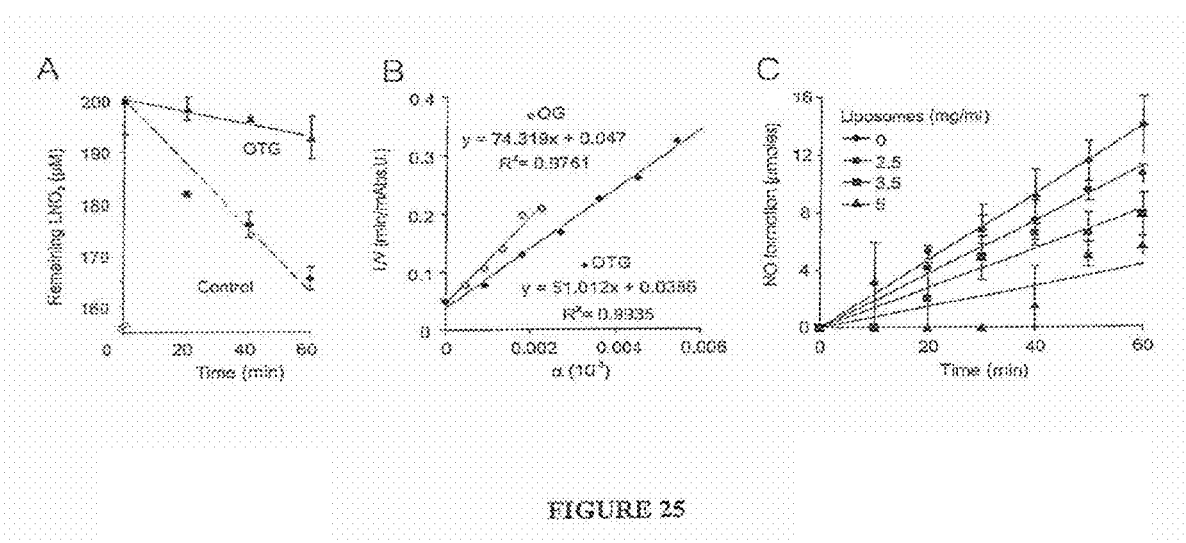
FIG. 25 shows micellar and phosphatidylcholine-cholesterol liposome inhibition of $LNO_2$ decomposition and •NO release. A) $LNO_2$ (200 μM) decomposition was measured in the absence and presence of 15 mg/ml OTG by mass spectrometry. B) Calculation of partition coefficient of $LNO_2$ into OTG and OG micelles from data shown in FIG. 25D). C) $LNO_2$ (80 μM)-dependent •NO formation was measured by cPTIO (200 μM) reduction to cPTI at different times in the presence of increasing liposome concentration (0-5 mg/ml).

Hydrophobic stabilization of LNO$_2$—The observation that LNO$_2$ is stable in organic solvents such as n-octanol, undergoing decay only after solvation in aqueous solutions, led us to analyze rates of •NO formation from LNO$_2$ in the presence of non-ionic detergents. The formation of •NO was followed by EPR (measuring cPTI formation) in the presence of different concentrations of octyl-β-glucopyranoside (OG) and octyl-thio-β-glucopyranoside (OTG). The rate of •NO release was constant and not influenced by these detergents until the critical micellar concentration (CMC) for each was achieved, after which •NO formation was inhibited as the volume of the hydrophobic environment increased (FIG. 24A). Similar results were obtained when measuring •NO formation via conversion of oxymyoglobin to metmyoglobin. Apparent •NO release rates remained constant until OG concentration reached ~2.8 mg/ml (CMC=2.77 mg/ml (11)). For OTG, inhibition of LNO$_2$-dependent •NO release occurred at ~7 mg/ml (CMC=7.8 mg/ml (11)) (FIG. 24B). To further confirm that LNO$_2$ was protected in lipophilic environments, LNO$_2$ decomposition was followed by UV absorbance at 268 nm and 320 nm (FIGS. 24 C-D). The inhibition of the NO$_2$ group loss at 268 nm was paralleled by inhibition of the formation of oxidation products at 320 nm, similarly paralleling the detergent-induced inhibition of •NO release observed by EPR and oxymyoglobin-based detection. The micellar stabilization of LNO$_2$ was also documented in OTG-containing buffers by MS-based quantification of LNO$_2$ after Bligh and Dyer extraction (FIG. 25A). Assuming rapid partitioning of LNO$_2$ between the aqueous and hydrophobic compartments, and that LNO$_2$ decay occurs only in the aqueous compartment, it can be shown that the rate of reaction v is given by the relationship:

$$v = \frac{k[\text{LNO}_2]}{1 + \alpha(K - 1)}$$

where k is the rate constant for aqueous breakdown, α is the fraction of total volume that is the hydrophobic volume, and K (hydrophobic/aqueous concentration ratio) is the partition constant for $LNO_2$. Thus, a plot of 1/v vs. α will yield a linear plot with slope divided by y-axis intercept equal to K−1. FIG. 25B shows this plot for OG and OTG, yielding values for K of 1580 and 1320 respectively.

For evaluating the stability of $LNO_2$ in bilayers rather than micelles, phosphatidylcholine-cholesterol liposomes prepared by reverse phase evaporation were utilized (3:1). This alternative hydrophobic bilayer environment also resulted in a dose-dependent inhibition of the release of •NO from $LNO_2$, as detected by EPR analysis of cPTI formation from cPTIO (FIG. 25C).

Figure 26:
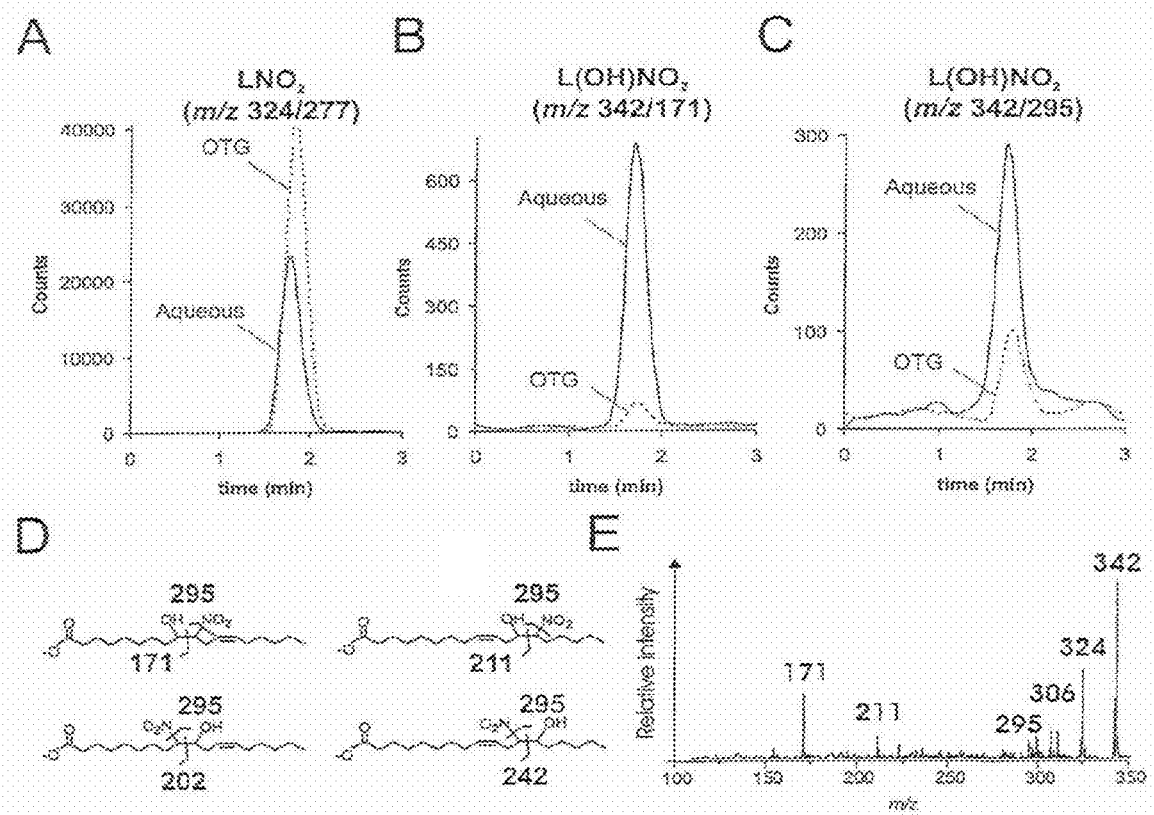
FIG. 26 shows formation of $L(OH)NO_2$ from $LNO_2$. A) $LNO_2$ was incubated in the presence (dotted line) or absence (solid line) of 15 mg/ml OTG, lipids were extracted and analyzed by ESI MS/MS. The presence of OTG inhibited $LNO_2$ decay as indicated by the MRM transition m/z 324/277 (A) and the formation of species with transitions m/z 342/171 and 342/295, which correspond to 9-hydroxy-10-nitro-12-octadecaenoic acid specifically (B), and all L(OH)$NO_2$ regioisomers (C), respectively. In the absence of OTG, increased $L(OH)NO_2$ yields were formed. D) Structures of possible nitrohydroxy adducts are presented along with their diagnostic fragments. E) Product ion spectra of $L(OH)NO_2$ showed two predominant ions consistent with expected fragments shown in (D), m/z 171 (9-hydroxy-10-nitro-12-octadecaenoic acid) and m/z 211 (12-hydroxy-13-nitro-9-octadecaenoic acid

The decay of $LNO_2$ in aqueous solutions results in the formation of multiple secondary fatty acid-derived products, as well as •NO. One pathway that may be involved in aqueous $LNO_2$ decay is the Michael-like addition reaction with $H_2O$ at the α carbon of the nitroalkene moiety. To test this possibility, and the influence of micellar stabilization of $LNO_2$, the formation of nitrohydroxylinoleic acid (L(OH)$NO_2$, m/z 342) was analyzed by MS. $LNO_2$-derived L(OH)$NO_2$ was evident after 60 min incubation in aqueous buffer at pH 7.4, with a concomitant decrease in $LNO_2$ levels (m/z 324). Addition of OTG at a concentration above the CMC significantly decreased extents of L(OH)$NO_2$ formation (FIG. 26A-C). Product ion analysis of L(OH)$NO_2$ generated a pattern of CID product ions that indicate the presence of two predominant regioisomers consistent with the heterolytic scission products of L(OH)$NO_2$, 9-hydroxy-10-nitro-12-octadecaenoic acid (m/z 171) and 12-hydroxy-13-nitro-9-octadecaenoic acid (m/z 211, FIG. 26 D-E).

Figure 27:
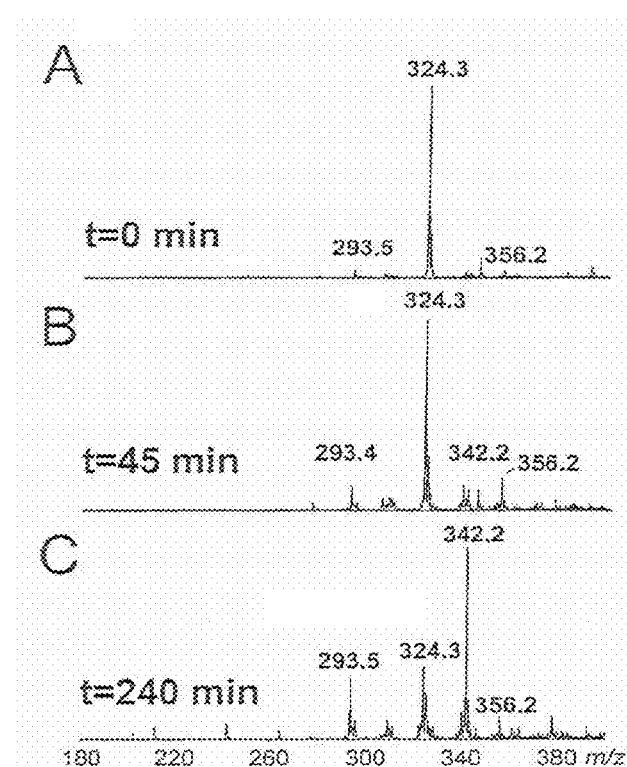
FIG. 27 shows mass spectrometric detection of $LNO_2$ decay products. $LNO_2$ (500 μM) was incubated in aqueous buffer phosphate buffer (100 mM phosphate pH 7.4 containing 100 μM DTPA) for 0, 45 and 240 min (A-C, respectively). Decay products were $CHCl_3$-extracted and analyzed by direct ESI MS/MS. Products were detected in the negative ion mode. The 293 m/z ion corresponds to an expected Nef reaction product, a conjugated ketone; m/z 342 is consistent with the mass of vicinal nitrohydroxy linoleic acid; and m/z 340 and 356 represent the hydroxy and peroxy derivatives of $LNO_2$, respectively.

The release of •NO by $LNO_2$ via a modified Nef reaction mechanism was further supported by detecting an aqueous degradation product with m/z 293 (FIG. 27). This mass to charge ratio is consistent with the formation of a conjugated ketone (Scheme 2 (FIG. 29), Stage 2). Also present in the mass spectrum is a peak for the vicinal nitrohydroxy adduct (m/z 342) and minor peaks corresponding to the hydroxy and peroxy derivatives of $LNO_2$ (m/z 340 and 356, respectively).

Nitrolinoleic acid is a pluripotent signaling molecule that exerts its bioactivity by acting as a high affinity ligand for PPARγ (2), activating protein kinase signaling cascades and, as shown herein, by serving as a hydrophobically-stabilized reserve for •NO. The activation of PPARγ-dependent gene expression by $LNO_2$ requires this ligand to be stabilized and transported as the intact nitroalkene to the nuclear receptor (2). The mechanism(s) involved in protein kinase activation by $LNO_2$ remain unclear, but can include direct ligation of receptors at the plasma membrane and/or covalent modification and activation of signaling mediators via Michael addition reactions. Current data reveals that the signaling actions of $LNO_2$ are multifaceted, with the activation of protein kinases and/or PPAR receptor activation not fully explaining observed cellular responses, such as the stimulation of cGMP-dependent vessel relaxation (5). The observation herein that $LNO_2$ decay yields •NO and that $LNO_2$ is subject to hydrophobic stabilization thus lends additional perspective to our understanding of how compartmentalization will influence the nature of cell signaling reactions mediated by fatty acid nitroalkene derivatives.

A central challenge in detecting •NO generation by relatively slow-releasing compounds (e.g., RSNO and organo-nitrate derivatives) is the risk of lack of specificity and sensitivity. This is especially the case when concurrent oxygen, heme, lipid, protein and probe-related redox reactions are possible. Quantitative rigor is also always a concern. To circumvent these problems, multiple approaches for the qualitative and quantitative detection of •NO generation by $LNO_2$ were employed herein. The release of •NO by $LNO_2$ was assessed quantitatively by spectrophotometric analysis of oxymyoglobin oxidation. Additional qualitative proof of $LNO_2$-derived •NO release came from EPR analysis of •NO-dependent cPTI formation, •NO-dependent chemiluminescence following reaction with $O_3$ and mass spectroscopic detection of anticipated decay products of $LNO_2$. Also, in aqueous solutions and in the absence of alternative reaction pathways, 4 mol •NO react with 1 mol $O_2$ to ultimately yield 4 mol $NO_2^-$. Thus, formation of $NO_2^-$ was used as additional evidence for •NO formation. The yield of $NO_2^-$ during $LNO_2$ decay was 3.5 fold lower than predicted from more direct •NO measurements based on oxymyoglobin oxidation. Several explanations can account for this apparent discrepancy. First, in the absence of •NO scavengers, •NO rapidly equilibrates with the gas phase, thus decreasing •NO available for oxidation to $NO_2^-$. Second, •NO reactions with carbonyl, hydroxyl and peroxyl radicals are extremely fast [k>~1×10$^{10}$ M$^{-1}$s$^{-1}$, (29)]. These free radical intermediates are likely formed during $LNO_2$ decomposition, as evidenced by products with mass to charge ratio 340 and 356 (FIG. 27). Thus, products of the reaction of these species with •NO may not contribute to $NO_2^-$ formation. Overall, multiple independent criteria support the capacity of $LNO_2$ to release of •NO.

The gas-phase chemiluminescence reaction of •NO with $O_3$ is a highly sensitive and specific method for detecting •NO and nitroso-derivatives of biomolecules. One widely utilized analytical strategy relies on the reductive cleavage of $NO_2^-$ and nitroso-derivatives by $I_3^-$. Treatment of samples with acidic sulfanilamide and $HgCl_2$ permits additional discrimination between heme-NO, $NO_2^-$, and putative RSNO and RNNO derivatives (20, 21, 25-28). The latter $HgCl_2$-resistant species [proposed as RNNO, (20)] may be best termed XNO$_x$ at this juncture, since $LNO_2$ also yields $O_3$ chemiluminescence following reaction with acidified sulfanilamide and $HgCl_2$ prior to injecting into iodine/triiodide mixtures and the detection chamber. These data reveal that a contribution of fatty acid nitroalkene derivatives to the measurement of various tissue biomolecule NO derivatives must additionally be considered. Of additional interest, the UV photolysis approach for NO$_x$ detection in biological samples directly stimulates decay of $LNO_2$ to yield •NO. This new insight thus raises significant concern about the accuracy of reported concentrations for •NO-derived species using UV photolysis, since nitrated fatty acids are the most prevalent bioactive oxides of nitrogen yet found in vivo (1). Protein fractionation via solvent extraction (e.g., acetone) prior to analysis of •NO derivatives in biological samples does not eliminate the possibility that nitrated fatty acids are a source of "detectable" or RSNO-like •NO formation by UV photolysis, as $LNO_2$ and other nitroalkenes readily partition into the polar phase of many extraction strategies including those employing acetone.

The observation that $LNO_2$ undergoes decay reactions to yield •NO in aqueous solution initially raised concern regarding how a significant and consistent $LNO_2$ content in plasma and red cells of healthy humans could be detected at near-micromolar concentrations (1). Appreciating that synthetic $LNO_2$ is stable in methanol suggested that the ionic microenvironment in which $LNO_2$ was solvated would significantly modulate stability. To first address the possibility that $LNO_2$ is stabilized by hydrophobic environments reminiscent of membranes and lipoproteins, it was observed that

Figure 28:
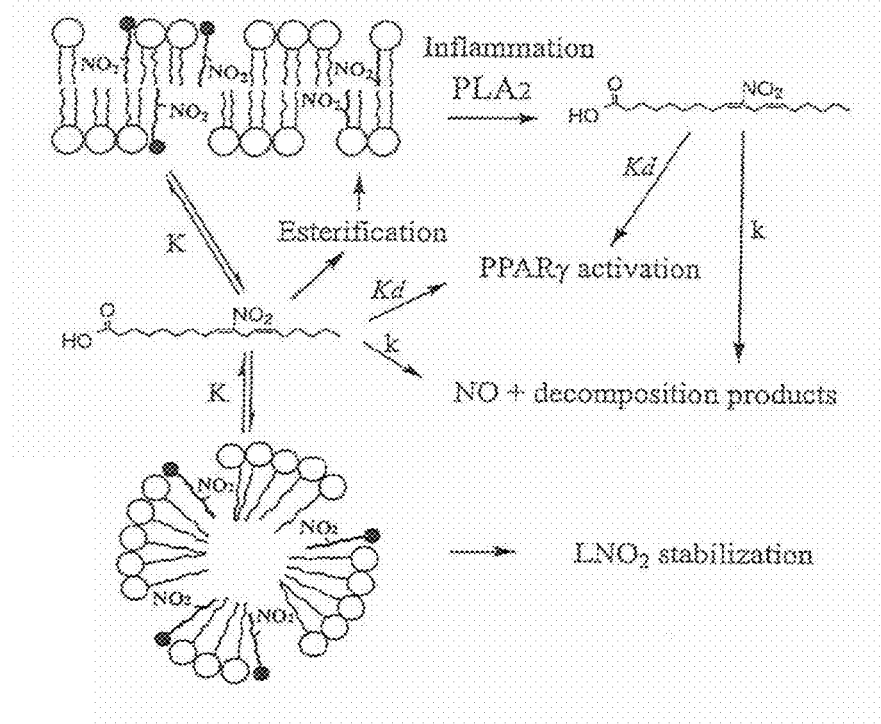
FIG. 28 shows Scheme 1, Hydrophobic regulation of $LNO_2$ decomposition and •NO release in lipid bilayers and micelles. The partitioning of $LNO_2$ into different cell compartments is in part governed by its partition coefficient (K~1500). $LNO_2$ may also be stabilized and placed in "reserve", in terms of attenuating •NO-mediated cell signaling capabilities, by esterification into complex lipids of membranes or lipoproteins. Alternatively, $LNO_2$ derivatives of complex lipids can be formed by direct nitration of esterified unsaturated fatty acids. During inflammatory conditions or in response to other stimuli, $LNO_2$ may be released from complex lipids by $A_2$-type phospholipases or esterases; thus mobilizing "free" $LNO_2$ that can in turn diffuse to exert receptor-dependent signaling actions or undergo decay reactions to release ·NO.

•NO release from LNO$_2$ was inhibited upon LNO$_2$ solvation in n-octanol. Further analysis using non-ionic detergent micelles, wherein the relatively hydrophobic NO$_2$ group of LNO$_2$ is expected to partition into non-polar microenvironments, revealed that LNO$_2$ decomposition and •NO release was inhibited (FIG. 24). Importantly, this occurred at and above the CMC of each detergent and lipid studied. Similar results were obtained using DPPC-phosphatidylcholine-cholesterol (3:1, mol/mol) liposomes, also revealing that LNO$_2$ is readily incorporated into and stabilized by lipid bilayers (FIG. 25C). This stabilizing influence of liposomes, which have a very low CMC, occurred at low hydrophobic phase volumes. These data reveal that LNO$_2$ will be stable in hydrophobic environments and that cell membranes and lipoproteins can serve as an endogenous reserve for LNO$_2$ and its downstream cell signaling capabilities. Indeed, ~80% of LNO$_2$ is esterified to complex lipids in blood, including phospholipids derived from red cell membrane lipid bilayers (1). This further suggests that during inflammatory responses, esterases and A$_2$-type phospholipases may hydrolyze and mobilize membrane-stabilized LNO$_2$ for mediating cell signaling actions. This regulated disposition of LNO$_2$ in lipophilic versus aqueous environments thus represents a "hydrophobic switch" that will control the nature of LNO$_2$ signaling activity (Scheme 1 (FIG. 28)).

The mechanisms accounting for •NO release from organic nitrites and nitrates are controversial, appear to be multifaceted and remain to be incisively defined. For example, the nitrate ester derivative nitroglycerin (NTG) has been used as a vasodilator for more than a century in the treatment of angina pectoris. Nitroglycerin does not directly decay to yield •NO or an •NO-like species that will activate soluble guanylate cyclase (sGC), rather cellular metabolism is required to yield a species capable of •NO-like activation of sGC. While several enzymes are identified as competent to mediate the denitration and "bioactivation" of NTG (e.g., xanthine oxidoreductase, cytochrome P450 oxidase and reductase, old yellow protein and mitochondrial aldehyde dehydrogenase-2), detailed insight is lacking as to unified redox chemistry, enzymatic and cellular mechanisms accounting for a) the 3 e-reduction of nitrate to an •NO-like species and b) the attenuated NTG metabolism that occurs during nitrate tolerance (30).

The present report of non-enzymatic release of •NO from endogenous fatty acid nitroalkene derivatives (e.g., LNO$_2$) lends additional perspective to how nitric oxide synthase-dependent •NO signaling can be transduced. It is shown via 3 different analytical approaches that the product of LNO$_2$ decay is unambiguously •NO. Mass spectrometric analysis and LNO$_2$ decay studies reported herein, in concert with previous understanding of the chemical reactivity of nitroalkenes, reveals a viable mechanism for how nitrated fatty acids can serve to transduce tissue •NO signaling capacity (Schemes 1 and 2).

The release of •NO by a vicinal nitrohydroxy arachidonic acid derivative detected in cardiac lipid extracts has been proposed (31) These derivatives induce vasorelaxation of rat aortic rings via possible •NO-dependent activation of guanylate cyclase. The intermediate formation of an analogous hydroxy derivative of nitrolinoleate, L(OH)NO$_2$, is documented herein to occur during LNO$_2$ decay in aqueous milieu (FIG. 27). Fatty acid nitroalkene derivatives appear to be clinically abundant, since both nitro and nitrohydroxy derivatives of all principal unsaturated fatty acids are present in healthy human blood plasma and urine (32). Present results indicate that hydroxy derivatives of fatty acid nitroalkenes represent the accumulation of Michael addition-like reaction products with H$_2$O that are in equilibrium with the parent nitroalkene and are not a direct precursor to •NO release.

Figure 22:
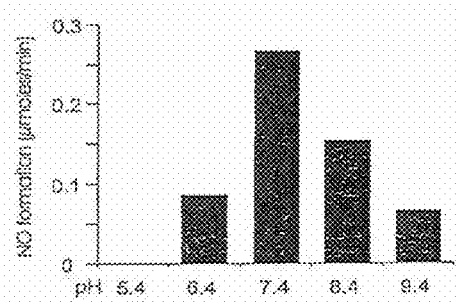
FIG. 22 shows the pH dependency of •NO formation from $LNO_2$. The rate of •NO formation from 80 μM $LNO_2$ (detected using EPR spectroscopic measurement of cPTIO (80 μM) reduction) was determined in buffers with different pHs.

A more viable mechanism accounting for •NO release by nitroalkenes is supported by 1) mass spectroscopic detection of expected decay products and 2) the aqueous and pH dependency of this process (FIG. 22), with LNO$_2$ decay and consequent •NO release involving protonation and deprotonation events. The mechanism accounting for •NO release by nitroalkenes is based on the Nef reaction (33,34), a standard reaction of organic nitro derivatives first described in 1894 (35).

The original Nef reaction entails complete deprotonation of an alkyl nitro compound with base to yield the nitroanion, followed by quenching with aqueous acid to cause hydrolysis to the corresponding carbonyl compound and oxides of nitrogen. Most Nef reactions are now performed using additional oxidants or reductants, rather than the simple acid-base chemistry of the original reaction (36-44). There are a few noteworthy points about this proposed mechanism that relate to how •NO can be ultimately produced. The nitrogen-containing product of the original Nef reaction is N$_2$O, a stable oxide of nitrogen that would not be a precursor to NO under the neutral aqueous conditions used herein to model biologically-relevant LNO$_2$ decay. The initial oxide of nitrogen formed, HNO, is unstable and quickly disproportionates to form N$_2$O as shown in Scheme 2 (FIG. 29) (Stage 2). While HNO (or the NO$^-$ anion) might conceivably yield one electron and be oxidized to •NO, this is not expected under neutral aqueous conditions. Alternatively, a nitroso intermediate formed during LNO$_2$ decay provides a plausible pathway to yield •NO. This nitroso intermediate is expected to have an especially weak C—N bond, easily forming •NO and a radical stabilized by conjugation with the alkene and stabilized by the OH group, a moiety known to stabilize adjacent radicals.

In Scheme 2 (FIG. 29) (Stage 1) the vicinal nitrohydroxy fatty acid derivative is in equilibrium with the nitroalkene. This is possible for two reasons. First, the nitro group in the vicinal nitrohydroxy fatty acid makes the adjacent hydrogen very acid (pK$_a$~7-8), thus facilitating formation of a significant amount of the nitronate anion at physiological pH. The anion can then release hydroxide, which when neutralized with the proton removed in the first step results in the net loss of neutral water. Second, the fatty acid nitroalkene is a strong electrophile and can readily undergo Michael conjugate addition reaction with the small amounts of hydroxide anion that are always present in aqueous solution under physiological pH conditions, explaining the facile equilibrium of vicinal nitrohydroxy fatty acids with their corresponding nitroalkene derivatives. In Scheme 2 (FIG. 29) (Stage 2), the lipid nitroalkene forms •NO as described above.

These proposed mechanisms for •NO formation from LNO$_2$ provided the testable hypothesis for how nitrated fatty acids can serve as a source of •NO using simple acid/base chemistry with no additional oxidants or reductants. Mass spectrometric detection of expected oxidized fatty acid products and direct detection of •NO formation supported this pathway of nitroalkene decay. This acid/base chemistry could also be employed by as-yet-undescribed enzymes that could catalyze physiologically-significant extents of •NO release from the multiple lipid nitroalkene derivatives now being observed (32).

Therapeutic agents that release •NO are a rapidly expanding area of drug design. Dual-acting nitro and nitroso derivatives of existing drugs have been synthesized and are being studied for efficacy in treating diabetes, metabolic syndrome, hypertension and atherosclerosis. These include •NO-releasing statin derivatives and NO-non-steroidal anti-inflammatory derivatives such as NO-acetacylic acid, NO-ibuprofen and NO-piroxicam. These adducts were devised based on the precept that an •NO donor moiety will augment therapeutic breadth and value. This class of pharmaceuticals are of particular relevance when alterations in endogenous •NO signaling contributes to tissue pathogenesis. In this regard, $LNO_2$ shares similarities with these classes of "chimeric" inflammatory-regulating compounds, as $LNO_2$ is a potent endogenous PPARγ agonist that rivals extents of PPARγ activation induced by similar concentrations of thiazolidinediones (2). Herein, the present invention shows that $LNO_2$ also has the capability to release •NO in a regulated manner. Thus, the potential signaling actions of $LNO_2$ are expected to be pluripotent in nature.

In summary, •NO-mediated oxidative reactions with unsaturated fatty acids yield nitroalkene derivatives. Once formed, nitrated fatty acids are hydrophobically stabilized by lipid bilayers and lipoproteins or alternatively, can be redistributed to aqueous environments to release •NO via a Nef-like reaction. In its native form, $LNO_2$ also activates nuclear PPAR receptor-mediated regulation of gene expression. These combined actions are expected to transduce the salutary inflammatory signaling reactions that have been described for both •NO and $LNO_2$. Because $LNO_2$ production is increased by oxidative inflammatory reactions, this species thus represents an adaptive mediator that regulates potentially pathogenic tissue responses to inflammation.

Throughout Example 4, several publications have been referenced. These publications are listed in the Reference List for Example 4. The disclosures of these publications in their entireties are hereby incorporated by reference into this application in order to more fully describe the compounds, compositions and methods described herein.

REFERENCE LIST FOR EXAMPLE 4

1. Baker, P. R., Schopfer, F. J., Sweeney, S., and Freeman, B. A. (2004) *Proc•Natl.Acad.Sci. U.S.A* 101, 11577-11582
2. Schopfer, F. J., Lin, Y., Baker, P. R., Cui, T., Garcia-Barrio, M., Zhang, J., Chen, K., Chen, Y. E., and Freeman, B. A. (2005) *Proc•Natl.Acad.Sci. U.S.A* 102, 2340-2345
3. Coles, B., Bloodsworth, A., Eiserich, J. P., Coffey, M. J., McLoughlin, R. M., Giddings, J. C., Lewis, M. J., Haslam, R. J., Freeman, B. A., and O'Donnell, V. B. (2002) *J.Biol.Chem.* 277, 5832-5840
4. Coles, B., Bloodsworth, A., Clark, S. R., Lewis, M. J., Cross, A. R., Freeman, B. A., and O'Donnell, V. B. (2002) *Circ.Res.* 91, 375-381
5. Lim, D. G., Sweeney, S., Bloodsworth, A., White, C. R., Chumley, P. H., Krishna, N. R., Schopfer, F., O'Donnell, V. B., Eiserich, J. P., and Freeman, B. A. (2002) *Proc•Natl.Acad.Sci. U.S.A* 99, 15941-15946
6. Ignarro, L. J., Byrns, R. E., Buga, G. M., and Wood, K. S. (1987) *Circ.Res.* 61, 866-879
7. Hogg, N. (2002) *Annu.Rev.Pharmacol. Toxicol.* 42, 585-600
8. Schopfer, F. J., Baker, P. R., and Freeman, B. A. (2003) *Trends Biochem.Sci.* 28, 646-654
9. Denicola, A., Souza, J. M., and Radi, R. (1998) *Proc•Natl.Acad.Sci. U.S.A* 95, 3566-3571
10. Denicola, A., Batthyany, C., Lissi, E., Freeman, B. A., Rubbo, H., and Radi, R. (2002) *J.Biol.Chem.* 277, 932-936
11. Liu, X., Miller, M. J., Joshi, M. S., Thomas, D. D., and Lancaster, J. R., Jr. (1998) *Proc•Natl.Acad.Sci. U.S.A* 95, 2175-2179
12. O'Donnell, V. B., Chumley, P. H., Hogg, N., Bloodsworth, A., Darley-Usmar, V. M., and Freeman, B. A. (1997) *Biochemistry* 36, 15216-15223
13. Rubbo, H., Radi, R., Anselmi, D., Kirk, M., Barnes, S., Butler, J., Eiserich, J. P., and Freeman, B. A. (2000) *J.Biol.Chem.* 275, 10812-10818
14. Coffey, M. J., Natarajan, R., Chumley, P. H., Coles, B., Thimmalapura, P. R., Nowell, M., Kuhn, H., Lewis, M. J., Freeman, B. A., and O'Donnell, V. B. (2001) *Proc•Natl.Acad.Sci. U.S.A* 98, 8006-8011
15. O'Donnell, V. B., Taylor, K. B., Parthasarathy, S., Kuhn, H., Koesling, D., Friebe, A., Bloodsworth, A., Darley-Usmar, V. M., and Freeman, B. A. (1999) *J.Biol.Chem.* 274, 20083-20091
16. O'Donnell, V. B., Coles, B., Lewis, M. J., Crews, B. C., Marnett, L. J., and Freeman, B. A. (2000) *J.Biol.Chem.* 275, 38239-38244
17. Eiserich, J. P., Baldus, S., Brennan, M. L., Ma, W., Zhang, C., Tousson, A., Castro, L., Lusis, A. J., Nauseef, W. M., White, C. R., and Freeman, B. A. (2002) *Science* 296, 2391-2394
18. Arnold, W. P., Mittal, C. K., Katsuki, S., and Murad, F. (1977) *Proc•Natl.Acad.Sci. U.S.A* 74, 3203-3207
19. Szoka, F., Jr. and Papahadjopoulos, D. (1980) *Annu.Rev.Biophys.Bioeng.* 9, 467-508
20. Feelisch, M., Rassaf, T., Mnaimneh, S., Singh, N., Bryan, N. S., Jourd'heuil, D., and Kelm, M. (2002) *FASEB J.* 16, 1775-1785
21. Gladwin, M. T., Wang, X., Reiter, C. D., Yang, B. K., Vivas, E. X., Bonaventura, C., and Schechter, A. N. (2002) *J.Biol.Chem.* 277, 27818-27828
22. Bligh, E. G. and Dyer, W. L. (1959) *Can.J.Biochem.Physiol.* 37, 911-917
23. Akaike, T., Yoshida, M., Miyamoto, Y., Sato, K., Kohno, M., Sasamoto, K., Miyazaki, K., Ueda, S., and Maeda, H. (1993) *Biochemistry* 32, 827-832
24. Hogg, N., Singh, R. J., Joseph, J., Neese, F., and Kalyanaraman, B. (1995) *Free Radic.Res.* 22, 47-56
25. McMahon, T. J., Moon, R. E., Luschinger, B. P., Carraway, M. S., Stone, A. E., Stolp, B. W., Gow, A. J., Pawloski, J. R., Watke, P., Singel, D. J., Piantadosi, C. A., and Stamler, J. S. (2002) *Nat.Med.* 8, 711-717
26. Stamler, J. S., Jaraki, O., Osborne, J., Simon, D. I., Keaney, J., Vita, J., Singel, D., Valeri, C. R., and Loscalzo, J. (1992) *Proc•Natl.Acad.Sci. U.S.A* 89, 7674-7677
27. Crawford, J. H., Chacko, B. K., Pruitt, H. M., Piknova, B., Hogg, N., and Patel, R. P. (2004) *Blood* 104, 1375-1382
28. Janero, D. R., Bryan, N. S., Saijo, F., Dhawan, V., Schwalb, D. J., Warren, M. C., and Feelisch, M. (2004) *Proc•Natl.Acad.Sci. U.S.A* 101, 16958-16963
29. Padmaja, S. and Huie, R. E. (1993) *Biochem.Biophys.Res.Commun.* 195, 539-544
30. Thatcher, G. R., Nicolescu, A. C., Bennett, B. M., and Toader, V. (2004) *Free Radic.Biol.Med.* 37, 1122-1143
31. Balazy, M., Iesaki, T., Park, J. L., Jiang, H., Kaminski, P. M., and Wolin, M. S. (2001) *J.Pharmacol.Exp. Ther.* 299, 611-619
32. Baker, P. R. S., Lin, Y., Schopfer, F. J., Woodcock, S. T., Long, M. H., Batthyany, C., Iles, K. E., Baker, L. M. S., Sweeney, S., Braunchaud, B. P., Chen, Y. E., and Freeman, B. A. (2005) *J Biol Chem* Submitted,
33. Pinnick, H. W. (1990) *Organic Reactions* 38, 655-792

34. Ballini, R. and Petrini, M. (2004) *Tetrahedron* 60, 1017-1047
35. Nef, J. U. (1894) *Justis Liebigs Annalan der Chemie* 263-342
36. Van Tamelen, E. E. and Thiede, R. J. (1952) *J.Am.Chem. .Soc.* 74, 2615-2618
37. Leitch, L. C. (1955) *Canadian Journal of Chemistry* 33, 400-404
38. Noland, W. E. (1955) *Chemical Reviews* 55, 137-155
39. Hawthorne, M. F. (1957) *J.Am.Chem.Soc.* 79, 2510-2515
40. Feuer, H. and Nielsen, A. T. (1962) J.Am.Chem.Soc. 84, 688
41. Armand, J. (1965) *Bulletin de la Societe Chimique de France* 3246-3255
42. Kornblum, N. and Brown, R. A. (1965) *J.Am.Chem.Soc.* 87, 1742-1747
43. Cundall, R. B. and Locke, A. W. (1968) *Journal of the Chemical Society [section] B: Physical Organic* 98-103
44. Wilson, H. and Lewis, E. S. (1972) *J.Am.Chem.Soc.* 94, 2283-2285

Example 5

The nitroalkenes of the present invention also display regulatory actions towards the expression of genes related to inflammatory responses, cell growth, cell differentiation, cell signaling, cell death (apoptosis) and metabolism. For example, nitrolinoleate regulates gene expression in human vascular endothelial cells and macrophages. Cells were stimulated with vehicle and linoleic acid (2.5 µM, the latter two treatments as controls) and LNO2O (2.5 mM) for 24 hours. The total RNA was purified with a Qiagen Kit and analyzed with a Whole Human Genome Oligo Array (G4112A, 41K Genes, Agilent). Results showed that nitrolinoleate regulates >5000 genes, with statistically-significant up-regulation of >2300 genes and down-regulation of >3000 genes. In contrast, the native (precursor) fatty acid, linoleic acid, only regulates 14 genes, with an up-regulation of 5 genes and the down-regulation of 9 genes.

Therefore, the present invention also provides for the selective regulation of clinically significant genes by nitrolinoleate. Table 5 lists examples of genes down-regulated by nitrolineate that are associated with cell signaling, growth, differentiation, metabolism, inflammatory responses, migration and apoptosis. Table 5 also includes genes involved in the Jak/STAT signaling pathway, the NF-κB pathway and the P13K/Akt pathway. The genes listed in Table 5 can be involved in one or more processes associated with cell signaling, growth, differentiation, metabolism, inflammatory responses, migration and apoptosis. These genes can also be involved in one or more pathways selected from the group consisting of the Jak/STAT signaling pathway, the NF-κB pathway and the P13K/Akt pathway.

TABLE 5

| Selected genes down-regulated by nitrolineate (>1.5 fold, p < 0.05) | |
|---|---|
| RAC2; ras-related C3 botulinum toxin substrate 2 (rho family, small GTP binding protein Rac2) | 2.47 |
| CDC2; cell division cycle 2, G1 to S and G2 to M | 2.75 |
| CDC42; cell division cycle 42 (GTP binding protein, 25 kDa) | 1.65 |
| CCND3; cyclin D3 | 1.51 |
| CCNE1; cyclin E1 | 1.58 |
| CAMK1; calcium/calmodulin-dependent protein kinase I | 2.24 |
| TCF4; transcription factor 4 | 2.63 |
| PPARGC1B; peroxisome proliferative activated receptor, gamma, coactivator 1, beta | 2.20 |
| RB1; retinoblastoma 1 (including osteosarcoma) | 2.06 |
| TNF; tumor necrosis factor (TNF superfamily, member 2) | 2.01 |
| TYK2; tyrosine kinase 2 | 2.00 |
| STAT1; signal transducer and activator of transcription 1, 91 kDa | 1.74 |
| CAV3; caveolin 3 | 1.76 |
| EDARADD; EDAR-associated death domain | 1.69 |
| DAPK2; death-associated protein kinase 2 | 1.73 |
| CASP8AP2; CASP8 associated protein 2 | 1.52 |
| ITR; intimal thickness-related receptor | 1.68 |

Table 6 lists additional genes that are also down-regulated by nitrolineate and are associated with cell signaling, growth, differentiation, metabolism, inflammatory responses, migration and apoptosis

TABLE 6

| Down-regulated genes (>1.5 fold, p < 0.05). Genes associated with cell signaling, growth, differentiation, metabolism, inflammatory responses, migration and apoptosis | | | | | |
|---|---|---|---|---|---|
| TGFBI; transforming growth factor, beta-induced, 68 kDa | 9.80 | ILK; integrin-linked kinase | 2.94 | MAPKAPK3; mitogen-activated protein kinase-activated protein kinase 3 | 2.18 |
| PLAU; plasminogen activator, urokinase | 7.58 | EGR2; early growth response 2 (Krox-20 homolog, *Drosophila*) | 2.65 | ADRB2; adrenergic, beta-2-, receptor, surface | 2.04 |
| VASP; vasodilator-stimulated phosphoprotein | 4.85 | FDPS; farnesyl diphosphate synthase (farnesyl pyrophosphate synthetase, dimethylallyltranstransferase, geranyltranstransferase) | 2.46 | IL11; interleukin 11 | 2.02 |
| AIF1; allograft inflammatory factor 1 | 3.95 | TGFB1; transforming growth factor, beta 1 (Camurati-Engelmann disease) | 2.46 | PIK3CB; phosphoinositide-3-kinase, catalytic, beta polypeptide | 1.93 |
| PTGS1; prostaglandin-endoperoxide synthase 1 (prostaglandin G/H synthase and cyclooxygenase) | 3.95 | IRS1; insulin receptor substrate 1 | 2.40 | TIMP2; tissue inhibitor of metalloproteinase 2 | 1.92 |

TABLE 6-continued

Down-regulated genes (>1.5 fold, p < 0.05). Genes associated with cell signaling, growth, differentiation, metabolism, inflammatory responses, migration and apoptosis

| Gene | Value | Gene | Value | Gene | Value |
|---|---|---|---|---|---|
| PTGES2; prostaglandin E synthase 2 | 1.59 | PDGFRA; platelet-derived growth factor receptor, alpha polypeptide | 2.36 | TLR2; toll-like receptor 2 | 1.89 |
| E2F2; E2F transcription factor 2 | 3.70 | RACGAP1; Rac GTPase activating protein 1 | 2.35 | LDLR; low density lipoprotein receptor (familial hypercholesterolemia) | 1.77 |
| NCOR2; nuclear receptor co-repressor 2 | 1.59 | NCR1; natural cytotoxicity triggering receptor 1 | 2.30 | CARD9; caspase recruitment domain family, member 9 | 3.33 |
| SRF; serum response factor (c-fos serum response element-binding transcription factor) | 1.56 | PDGFA; platelet-derived growth factor alpha polypeptide | 2.27 | FLJ23091; putative NFkB activating protein 373 | 1.74 |
| BCL2A1; BCL2-related protein A1 | 3.50 | TIMP1; tissue inhibitor of metalloproteinase 1 (erythroid potentiating activity, collagenase inhibitor) | 3.62 | PDGFC; platelet derived growth factor C | 1.72 |
| CARD9; caspase recruitment domain family, member 9 | 3.33 | TIMP3; tissue inhibitor of metalloproteinase 3 (Sorsby fundus dystrophy, pseudoinflammatory) | 2.27 | ARHGEF1; Rho guanine nucleotide exchange factor (GEF) 1 | 1.64 |
| FN1; fibronectin 1 | 3.33 | MMP19; matrix metalloproteinase 19 | 1.58 | JUNB; jun B proto-oncogene | 1.60 |
| PPARD; peroxisome proliferative activated receptor, delta | 3.12 | CAMK1; calcium/calmodulin-dependent protein kinase I | 2.24 | MYLK; myosin, light polypeptide kinase | 3.13 |
| | | MAPKAPK3; mitogen-activated protein kinase-activated protein kinase 3 | 2.18 | ROCK1; Rho-associated, coiled-coil containing protein kinase 1 | 1.59 |
| | | | | IGF1; insulin-like growth factor 1 (somatomedin C) | 1.54 |
| | | | | VEGFB; vascular endothelial growth factor B | 1.51 |
| | | | | ECGF1; endothelial cell growth factor 1 (platelet-derived) | 1.73 |

Table 7 provides gene that are up-regulated by nitrolinoleate. These genes are associated with apoptosis, cell signaling and/or growth.

TABLE 7

Genes up-regulated by nitrolinoleate.

| | |
|---|---|
| IL10RA; interleukin 10 receptor, alpha | 3.173 |
| GADD45G; growth arrest and DNA-damage-inducible, gamma | 3.155 |
| IRS2; insulin receptor substrate 2 | 3.243 |
| HO-1, heme oxygenase-1 | 4.086 |
| GADD45A; growth arrest and DNA-damage-inducible, alpha | 2.823 |
| CASP1; caspase 1, apoptosis-related cysteine protease (interleukin 1, beta, convertase) | 2.572 |
| CASP4; caspase 4, apoptosis-related cysteine protease | 2.57 |
| CCNA1; cyclin A1 | 2.558 |
| JUN; v-jun sarcoma virus 17 oncogene homolog (avian) | 2.454 |
| CASP3; caspase 3, apoptosis-related cysteine protease | 1.689 |
| GADD45B; growth arrest and DNA-damage-inducible, beta | 1.674 |
| AATK; apoptosis-associated tyrosine kinase | 1.503 |
| AMID; apoptosis-inducing factor (AIF)-homologous mitochondrion-associated inducer of death | 8.362 |

Example 6

Figure 30:
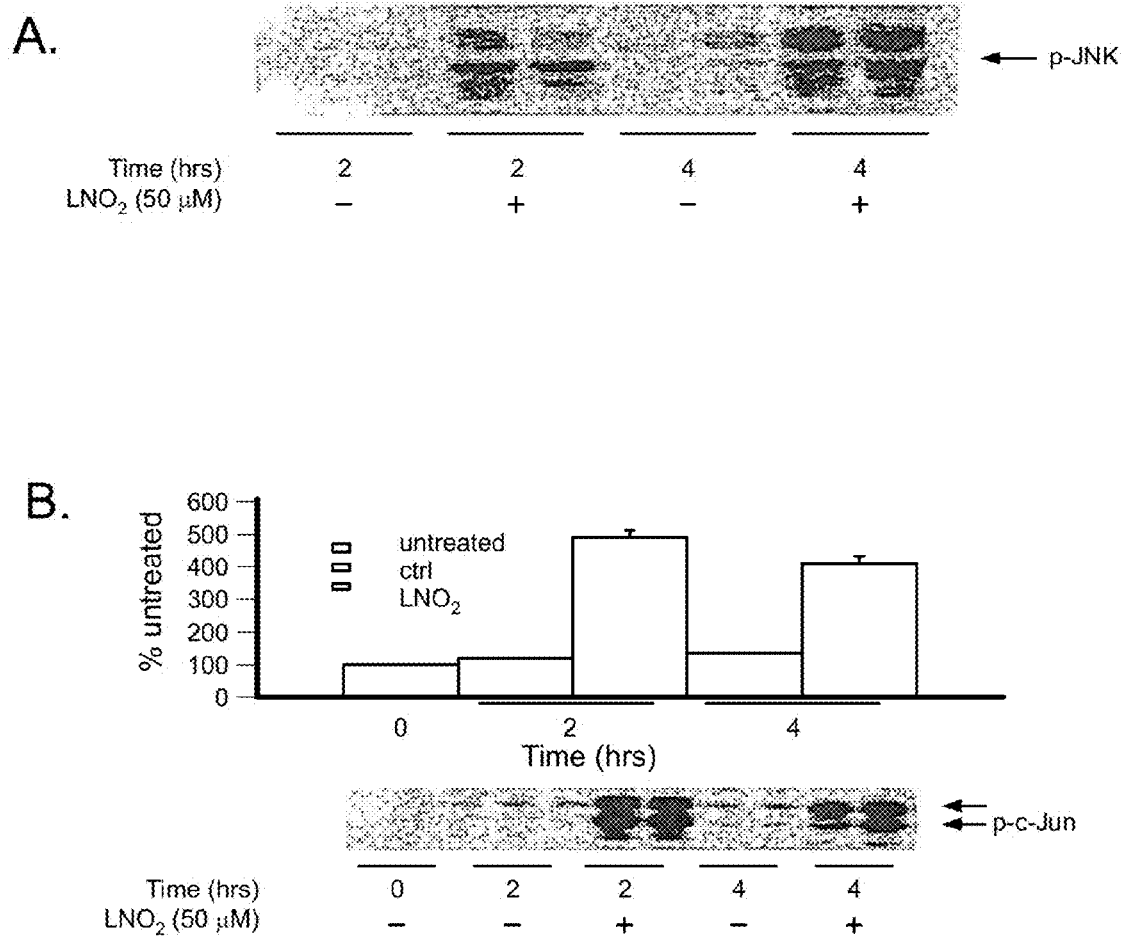
FIG. 30 shows that nitroalkenes potently activate p-JNK and p-c-Jun protein kinases by stimulating their phosphorylation. The activation of these cell signaling mediators will profoundly impact on cell inflammatory responses, proliferation and differentiation. This example shows human lung epithelial cell responses of p-JNK and p-c-Jun.
Figure 32:
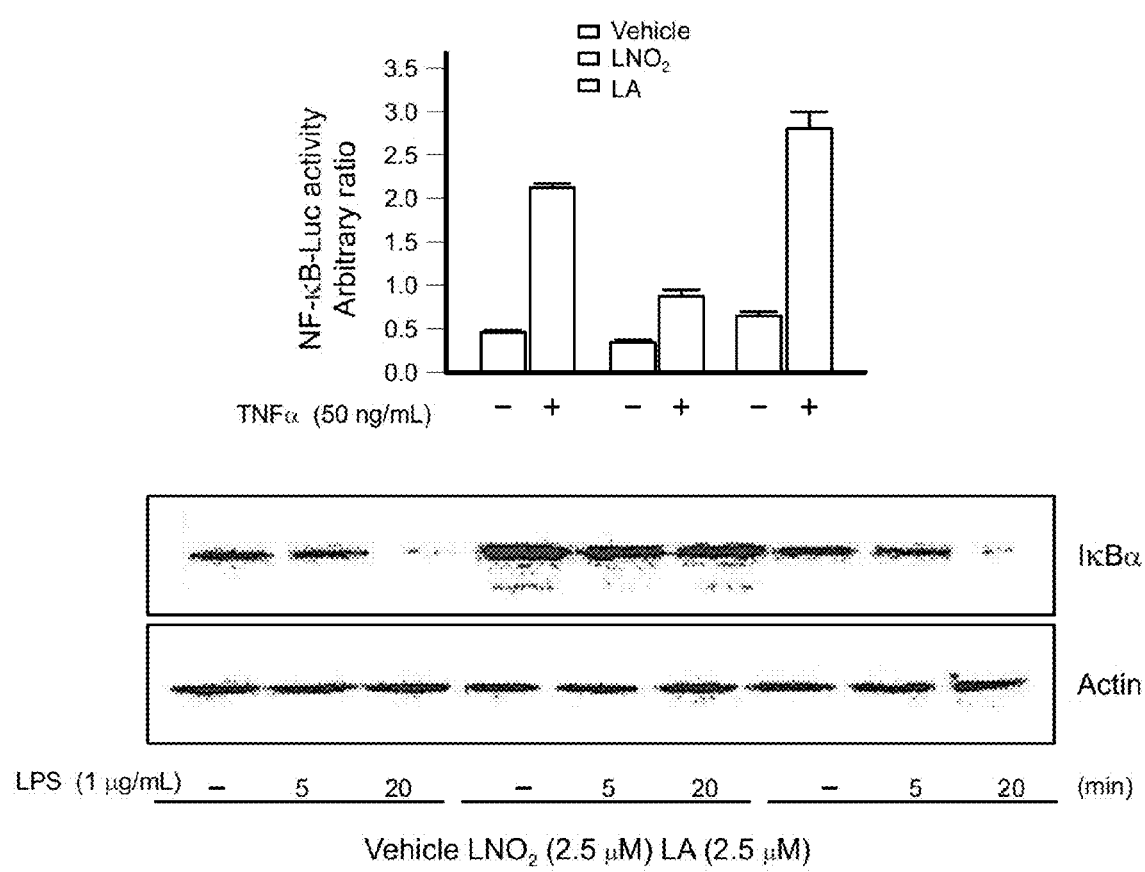
FIG. 32 shows that nitrolinoleate ($LNO_2$), and not the control fatty acid linoleate (LA), inhibits activity of NF-kB pathways as indicated by a) luciferase-linked NFkB-response element reporter assay in response to the inflammatory mediator TNFa and b) direct analysis of the degradation f the NFkB inhibitor protein, IkB in response to the inflammatory mediator *E. coli* LPS.

The present invention also provides the activation of p-JNK and p-c-Jun protein kinases by nitrated lipids, by stimulating the phosphorylation of these kinases. The activation of these cell signaling mediators allow modulation of cell signaling, growth, differentiation, metabolism, inflammatory responses, migration and apoptosis. FIG. 30 shows human lung epithelial cell responses of p-JNK and p-c-JUN upon administration of nitrolineate. The nitroalkenes of the present invention also activate the ERK MAPK pathway in human lung epithelial cells, as shown by a dramatic increase in ERK phosphorylation (e.g. activation) and the phosphorylation of its downstream target signaling protein, pELK, illustrated in FIG. 31. The nitroalkenes of the present invention also inhibit activity of NF-κB pathway as indicated by a) luciferase-linked NFkB-response element reporter assay in response to the inflammatory mediator TNFα and b) direct analysis of the degradation f the NFkB inhibitor protein, IkB in response to the inflammatory mediator *E. coli* LPS (FIG. 32).

Example 7

Figure 33:
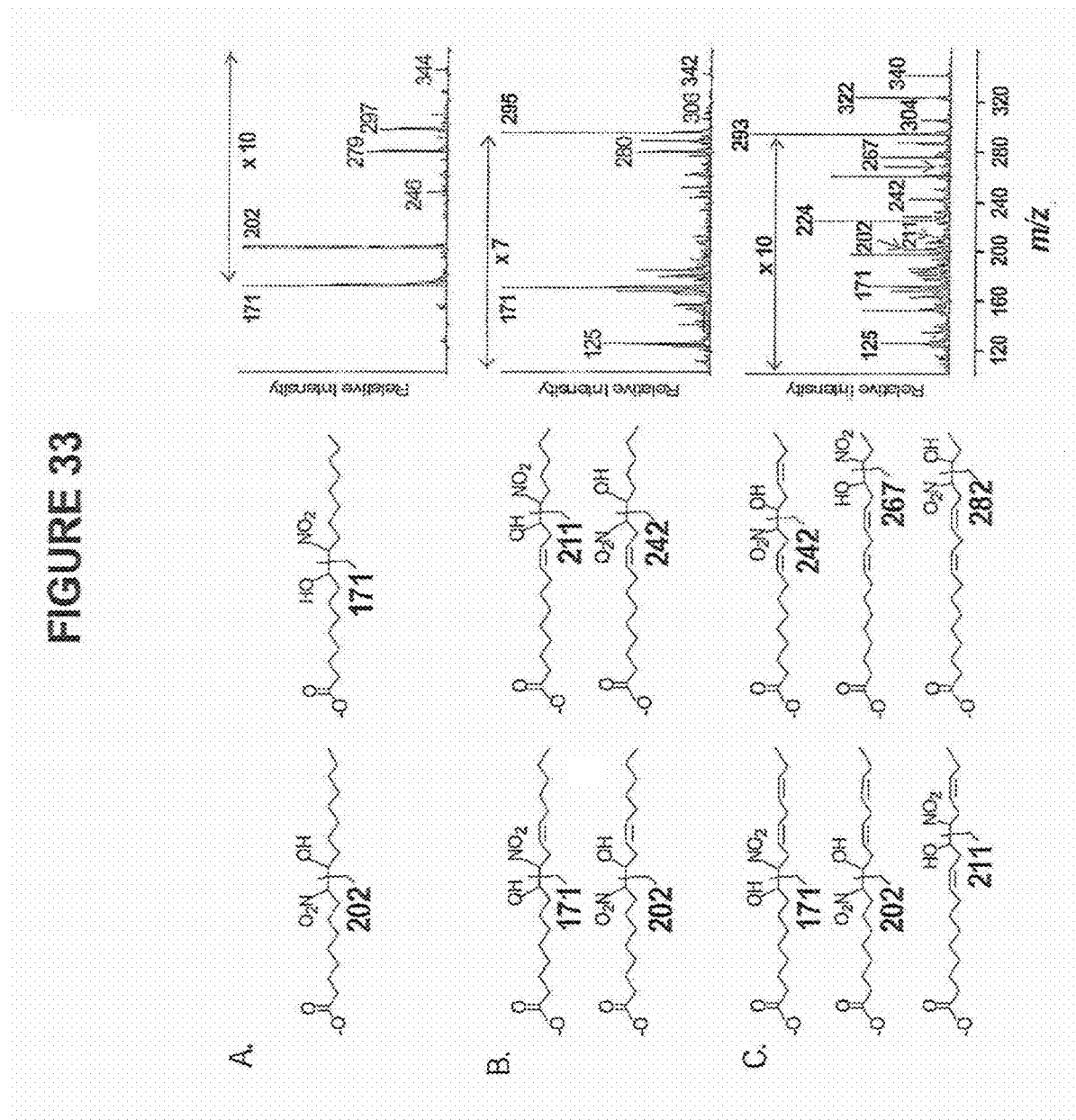
FIG. 33 shows the mass spectra of nitro/hydroxy fatty acid.

Synthesis and characterization of nitro/hydroxy fatty acids. The Michael addition reaction of water to nitroalkenes results in formation of nitro-hydroxy derivative (18:1, 18:2 and 18:3 nitro-hydroxy species shown in FIG. 33). These hydroxylated species are prepared by placing nitroalkenes in basic aqueous conditions, isolation by solvent extraction and purification by HPLC or thin layer chromatography. Fatty acid nitro-hydroxy derivatives can (a) display unique cell signaling activities, (b) represent a more stable "storage form" of the PPAR receptor-avid nitroalkene parent molecule and (c) permit determination of specific positional isomers of nitroalkenes by directing, upon hydroxylation, nucleophilic heterolytic scission between the nitro and hydroxy-bonded fatty acid alkene. Nitro isomer-specific fragments can then be detected by mass spectrometry (FIG. 33).

Example 8

Figure 34:
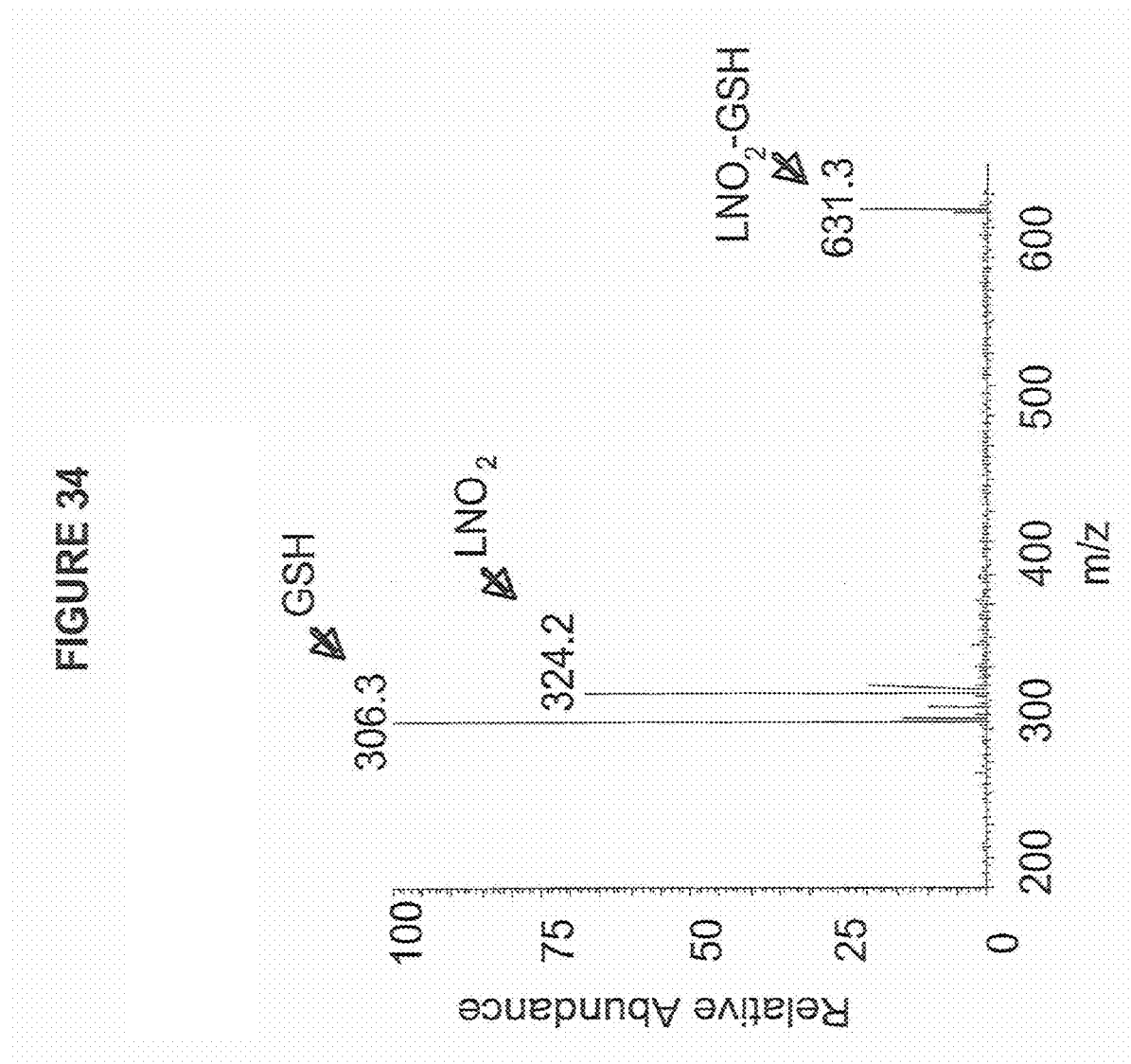
FIG. 34 shows the mass spectrum of the Michael addition product between nitro linoleate and glutathione.

Addition of glutathione to nitraed fatty acids. In a neutral buffered solution, the thiol and nitrated FA (e.g., nitrated oleate or linoleate) can be combined from equimolar to 10:1 ratios of nitroalkene to thiol. Mass spectrometry shows nitrolinoleate forms a covalent Michael addition reaction product with the tripeptide glutathione (m/z 631.3, LNO2-GSH) (FIG. 34). This adduct can be "fingerprinted" by its source fragmentation in the mass spectrometer to the precursors glutathione (m/z 306.3) and nitrolinoleate (m/z 324.2, $LNO_2$).

Throughout this application, various publications are referenced. The disclosures of these publications in their entireties are hereby incorporated by reference into this application in order to more fully describe the compounds, compositions and methods described herein.

Various modifications and variations can be made to the compounds, compositions and methods described herein. Other aspects of the compounds, compositions and methods described herein will be apparent from consideration of the specification and practice of the compounds, compositions and methods disclosed herein. It is intended that the specification and examples be considered as exemplary.

What is claimed:

1. A method for treating vascular disease in a subject in need thereof, comprising administering an effective amount of a lipid having the structure:

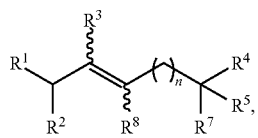

wherein:
$R^1$ is selected from the group consisting of $C_1$-$C_{24}$ alkyl, $C_1$-$C_{24}$ alkenyl, and $C_1$-$C_{24}$ alkynyl;
$R^2$, $R^3$, $R^7$, and $R^8$ are each independently selected from the group consisting of hydrogen, $NO_2$, OH, and OOH, wherein at least one of $R^2$, $R^3$, $R^7$, and $R^8$ is $NO_2$;
$R^4$ is $C_1$-$C_{24}$ alkyl, $C_1$-$C_{24}$ alkenyl, or $C_1$-$C_{24}$ alkynyl, wherein $R^4$ comprises a terminal $COOR^6$ and $R^6$ is hydrogen, $C_1$-$C_{24}$ alkyl, or a pharmaceutically acceptable counterion;
$R^5$ is hydrogen or $R^4$ and $R^5$ collectively form =C($R^9$)($R^{10}$), wherein $R^9$ is $C_1$-$C_{24}$ alkyl, $C_1$-$C_{24}$ alkenyl, or $C_1$-$C_{24}$ alkynyl and $R^{10}$ is hydrogen, $NO_2$, OH, or OOH; and
n is from 1 to 24, and a therapeutic agent.

2. The method of claim 1, wherein the therapeutic agent is selected from a group consisting of antibodies, antivirals, steroidal and non-steroidal anti-inflammatories, conventional immunotherapeutic agents, cytokines, chemokines, and growth factors.

3. The method of claim 1, wherein the lipid comprises a fatty acid.

4. The method of claim 1, wherein the lipid is selected from the group consisting of glycolipids, glycerolipids, phospholipids, and cholesterol.

5. The method of claim 1, wherein the lipid is selected from the group consisting of oleic acid (18:1), 22:6, and docosahexanoic acid.

6. The method of claim 1, wherein the lipid comprises 10-nitro-9-cis,12-cis-octadecadienoic acid.

7. The method of claim 1, wherein the lipid is selected from the group consisting of linoleic acid (18:2), linolenic acid (18:3), and cholesterol linoleate.

8. The method of claim 1, wherein the lipid comprises arachidonic acid (20:4).

9. The method of claim 1, the lipid having the formula:

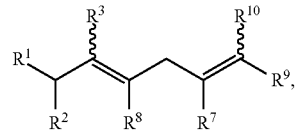

wherein:
$R^9$ is $C_1$-$C_{24}$ alkyl, $C_1$-$C_{24}$ alkenyl, or $C_1$-$C_{24}$ alkynyl and includes a terminal $COOR^6$; and
$R^{10}$ is hydrogen, $NO_2$, OH, or OOH,
wherein at least one of $R^2$, $R^3$, $R^7$, $R^8$, and $R^{10}$ is $NO_2$.

10. The method of claim 1, wherein $R^1$ is $C_4$-$C_{10}$ alkyl; $R^2$, $R^8$, and $R^{10}$ are hydrogen; $R^7$ is $NO_2$; and $R^9$ is $C_6$-$C_{12}$ alkyl.

11. The method of claim 1, wherein $R^3$ and $R^8$ are cis to one another, and $R^7$ and $R^{10}$ are cis to one another.

12. The method of claim 1, wherein $R^1$ is $C_4$-$C_{10}$ alkyl; $R^2$, $R^3$, and $R^7$ are hydrogen; $R^8$ is $NO_2$; and $R^4$ is $C_6$-$C_{12}$ alkyl.

13. The method of claim 1, wherein the lipid comprises 12-nitro-9-cis,12-cis-octadecadienoic acid.

14. The method of claim 1, wherein $R^9$ is $C_6$-$C_{12}$ alkyl.

15. The method of claim 1, wherein the lipid is 10-nitro-9-cis-octadecaenoic acid.

16. The method of claim 1, wherein the lipid and the therapeutic agent are administered from a group consisting of concomitantly, simultaneously, and sequentially.

17. The method of claim 1, wherein the lipid and the therapeutic agent are administered selected from a group consisting of topically, orally, by inhalation, parenterally, intravenously, intraperitoneally, intramuscularly, subcutaneously, intracavity, transdermally, intratracheally, and extracorporeally.

18. The method of claim 1, wherein the vascular disease is selected from a group consisting of cardiomyopathy, hypertension, atherosclerosis, myocardial infarction, peripheral vascular disease, coronary artery disease, heart failure and stroke.

* * * * *

UNITED STATES PATENT AND TRADEMARK OFFICE
CERTIFICATE OF CORRECTION

PATENT NO. : 9,867,795 B2
APPLICATION NO. : 15/357731
DATED : January 16, 2018
INVENTOR(S) : Bruce A. Freeman et al.

It is certified that error appears in the above-identified patent and that said Letters Patent is hereby corrected as shown below:

In the Specification

Column 1, Lines 25-28, Delete:
"This invention was made with government support under Grant Numbers RO1HL58115 and RO1HL64937 awarded by the National Institutes of Health. The government has certain rights in the invention."

And Insert:
--This invention was made with government support under Grant Numbers HL058115 and HL064937 awarded by the National Institutes of Health. The government has certain rights in the invention.--

Signed and Sealed this
Fifteenth Day of September, 2020

Andrei Iancu
*Director of the United States Patent and Trademark Office*